United States Patent
Luk et al.

(10) Patent No.: US 6,313,310 B1
(45) Date of Patent: Nov. 6, 2001

(54) 4-AND 5-ALKYNYLOXINDOLES AND 4-AND 5-ALKENYLOXINDOLES

(75) Inventors: Kin-Chun Luk, North Caldwell; Paige E. Mahaney, Montclair; Steven Gregory Mischke, Florham Park, all of NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/464,238

(22) Filed: Dec. 15, 1999

(51) Int. Cl.$^7$ .................................................. C07D 403/02
(52) U.S. Cl. ....................... 548/312.1; 514/397; 514/415; 548/110; 548/486
(58) Field of Search ................................ 548/486, 312.1, 548/110; 514/418, 397

(56) References Cited

U.S. PATENT DOCUMENTS

| | | | |
|---|---|---|---|
| 4,556,672 | 12/1985 | Kadin .................................. | 514/414 |
| 5,206,261 | 4/1993 | Kawaguchi et al. ................. | 514/418 |
| 5,322,950 | 6/1994 | Sircar et al. .......................... | 548/253 |
| 5,374,652 | 12/1994 | Buzzetti et al. ...................... | 514/418 |
| 5,397,787 | 3/1995 | Buzzetti et al. ...................... | 514/300 |
| 5,409,949 | 4/1995 | Buzzetti et al. ...................... | 514/414 |
| 5,488,057 | 1/1996 | Buzzetti et al. ...................... | 514/312 |
| 5,576,330 | 11/1996 | Buzzetti et al. ...................... | 514/312 |
| 5,792,783 | 8/1998 | Tang et al. ............................ | 514/397 |
| 5,834,504 | 11/1998 | Tang et al. ............................ | 514/418 |
| 5,883,113 | 3/1999 | Tang et al. ............................ | 514/418 |
| 5,883,116 | 3/1999 | Tang et al. ............................ | 514/418 |
| 5,886,200 | 3/1999 | Tang et al. ............................ | 514/420 |

FOREIGN PATENT DOCUMENTS

| | | |
|---|---|---|
| 0436333 A2 | 12/1990 | (EP) . |
| 0580502 A1 | 7/1993 | (EP) . |
| WO 92/07830 | 5/1992 | (WO) . |
| WO 95/01349 | 1/1995 | (WO) . |
| WO 96/00226 | 1/1996 | (WO) . |
| WO 96/16964 | 6/1996 | (WO) . |
| WO 96/22976 | 8/1996 | (WO) . |
| WO 96/32380 | 10/1996 | (WO) . |
| WO 96/40116 | 12/1996 | (WO) . |
| WO 97/11692 | 4/1997 | (WO) . |
| WO 97/16447 | 5/1997 | (WO) . |
| WO 97/45409 | 12/1997 | (WO) . |
| WO 97/46551 | 12/1997 | (WO) . |
| WO 98/07695 | 2/1998 | (WO) . |
| WO 98/24432 | 6/1998 | (WO) . |
| WO 98/50356 | 11/1998 | (WO) . |
| WO 99/10325 | 3/1999 | (WO) . |
| WO 99/15500 | 4/1999 | (WO) . |
| WO 99/48868 | 9/1999 | (WO) . |
| WO 99/61422 | 12/1999 | (WO) . |
| WO 00 08202 | 2/2000 | (WO) . |
| WO 00/12084 | 3/2000 | (WO) . |

OTHER PUBLICATIONS

Abstract Acc. No. 94–028085/199404 (Abstract of EP 0580502) Adam et al.
Sun et al., J. Med. Chem., 41:2588–2603 (1998).
Sun et al., "Synthesis and Biological Evaluation of Novel 3–[(Substituted pyrrol–2–yl)methylidenyl] indolin–2–ones as Potent and Selective Inhibitors of the Flk–1/KDR Receptor Tyrosine Kinase", Abstract presented at at Trip Report: ACS National Meeting, Dallas, Texas, Apr. 1998.
Mohammadi et. al, Science, 276:955–960 (May 9, 1997).

*Primary Examiner*—Floyd D. Higel
(74) *Attorney, Agent, or Firm*—George W. Johnston; Patricia S. Rocha-Tramaloni

(57) ABSTRACT

Disclosed are 4- and 5-alkynyloxindoles as well as 4- and 5-alkenyloxindoles that inhibit or modulate protein kinases, in particular JNK protein kinases. The compounds of the invention and their pharmaceutically acceptable salts, and prodrugs of said compounds, are useful as anti-inflammatory agents, particularly useful in the treatment of rheumatoid arthritis. Also disclosed are pharmaceutical compositions containing the foregoing compounds, methods for the treatment and/or control of inflammation, particularly in the treatment or control of rheumatoid arthritis using these compounds, as well as intermediates useful in the preparation of compounds of the invention.

51 Claims, No Drawings

4-AND 5-ALKYNYLOXINDOLES AND 4-AND 5-ALKENYLOXINDOLES

FIELD OF THE INVENTION

The present invention is directed to novel 4- and 5-alkynyloxindoles as well as 4- and 5-alkenyloxindoles which inhibit or modulate protein kinases, in particular JNK protein kinases. These compounds and their pharmaceutically acceptable salts, and prodrugs of said compounds, are useful as anti-inflammatory agents, particularly useful in the treatment of rheumatoid arthritis. The invention is also directed to pharmaceutical compositions containing such compounds, and to methods for the treatment and/or control of inflammation, particularly in the treatment or control of rheumatoid arthritis. This invention is further directed to intermediates useful in the preparation of the foregoing compounds.

BACKGROUND OF THE INVENTION

Protein kinases are a class of proteins that regulate a variety of cellular functions. This is accomplished by the phosphorylation of specific amino acids on protein substrates resulting in conformational alteration of the substrate protein. The conformational change modulates the activity of the substrate or its ability to interact with other binding partners. The enzyme activity of the protein kinase refers to the rate at which the kinase adds phosphate groups to a substrate. It can be measured, for example, by determining the amount of a substrate that is converted to a product as a function of time. Phosphorylation of a substrate occurs at the active-site of a protein kinase.

The JNK (Jun N-terminal kinase) protein kinases (also know as "stress-activated protein kinases" or "SAPK") are members of the mitogen-activated protein (MAP) kinases. See, e.g., S. Gupta et al., EMBO J., vol. 15 no. 11 (1996) pp. 2760–2770; and Yang et al., *Nature*, vol. 289 (Oct. 23, 1997) pp. 865–870. At least ten JNK isoforms are currently known. See, Gupta, id. As its name indicates, one of the substrates for JNK is c-Jun. JNK phosphorylates the $NH_2$-terminal activation domain of c-Jun on Ser63 and Ser73, causing increased c-Jun transcriptional activity. See Gupta, id. In turn, c-Jun is an AP-1 transcription factor that mediates immediate-early gene expression. See, e.g., A. Minden et al., Biochimica et Biophysica Acta 1333 (1997) F85–F104; and P. Agel et. al., Biochimica et Biophysica Acta, vol. 1072 (1991) pp. 129–157.

The JNK protein kinase is markedly activated in response to treatment of cells with pro-inflammatory cytokines or exposure to environmental stress. JNK thus mediates the effect of extracellular stimuli on c-Jun. See Gupta, supra; and Minden, supra. Accordingly, JNK is a physiological regulator of AP-1 transcriptional activity. Thus, inhibition of JNK activity will inhibit AP-1-dependent transcription of inflammatory and immune mediators which are implicated in pathological proliferative conditions, for example inflammatory diseases and neuro-degenerative diseases, in particular, rheumatoid arthritis. See, eg. Swantek et al., Molecular and Cellular Biology, vol. 17 (1997) pp. 6274–6282; Maroney et al., J. Neuroscience, vol. 18 (Jan. 1, 1998) pp. 104–111; and Minden, supra, at F92.

The rat homologue of JNK is also called SAPK (stress-activated protein kinase). SAPK isoforms share significant (>90%) sequence identity with the corresponding JNK isoforms [compare Kyriakis et al., *Nature*, Vol 369 (May 12, 1994) pp. 156–160 and Gupta et al., supra]. Both JNK and SAPK are capable of phosphorylation of the c-Jun substrate and thus have very similar enzyme activity. JNK and SAPK are part of a protein kinase cascade that is activated by various extracellular stimuli. See e.g. Minden supra; and Kyriakis et al., BioEssays Vol 18 (1996) pp. 567–577. JNK and SAPK each can be activated by phosphorylation on specific threonine and tyrosine residues by dual specificity MAP kinase kinases such as MKK4, SEK-1, or MKK7. See Kyriakis et al., supra; and Tournier et al., Proceedings of the National Academy of Sciences USA Vol. 94 (July 1997), pp. 7337–7342. The dual specificity MAP kinase kinases can be activated by phosphorylation on serine and/or threonine residues by MAP kinase kinase kinases such as MEKK-1. Thus, measurement of JNK or SAPK enzyme activity may be enhanced by activation by the upstream or preceding kinases. Moreover, measurement of SAPK inhibition is closely correlated with JNK inhibition.

Inhibitors of protein kinase catalytic activity are known in the art. See WO 98/24432 (indoline compounds that inhibit FLK protein kinase); WO 97/45409 (substituted tetralylmethylene-oxindole analogues that inhibit tyrosine kinase). In particular, small molecule inhibitors typically block the binding of substrates by tightly interacting with the protein kinase ATP binding site (or "active site"). See WO 98/24432. It is desirable to identify small-molecule compounds that may be readily synthesized and are effective in inhibiting the catalytic activity of protein kinases, in particular of the JNK protein kinases.

Indolinone (also known as oxindole) compounds asserted to be useful in regulating abnormal cell proliferation through tyrosine kinase inhibition are disclosed for example in WO 96/40116, WO 98/07695, WO 95/01349, WO 96/32380, WO 96/22976, WO 96/16964 and WO 98/50356 (2-indolinone derivatives as modulators of protein kinase activity); Mohammadi et. al, *Science*, Vol. 276, May 9, 1997, pp. 955–960. Oxindole derivatives have also been described for various other therapeutic uses: U.S. Pat. No. 5,206,261 (improvement of cerebral function); WO 92/07830 (peptide antagonists); EP 580 502 A1 (antioxidants).

There continues to be a need for easily synthesized, small molecule compounds effective in inhibiting JNK protein kinase and thus useful in the treatment or control of pathological proliferative conditions, for example inflammatory diseases and neuro-degenerative diseases, in particular, rheumatoid arthritis. It is thus an object of this invention to provide such compounds and compositions containing such compounds.

SUMMARY OF THE INVENTION

The present invention relates to 4- and 5-alkynyloxindoles and 4- and 5-alkenyloxindoles capable of inhibiting the activity of one or more JNK protein kinases. Such compounds are useful for the treatment of inflammatory diseases and neuro-degenerative diseases. In particular, the compounds of the present invention are especially useful in the treatment or control of rheumatoid arthritis.

In one embodiment, the present invention is directed to 4-alkynyloxindoles and 4-alkenyloxindoles having the following formula:

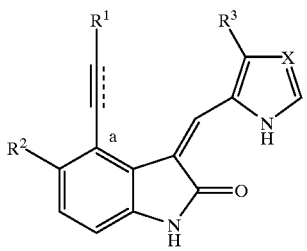

and prodrugs and pharmaceutically active metabolites of compounds of formula I, and the pharmaceutically acceptable salts of all of the foregoing compounds,
wherein:

$R^1$ is selected from the group consisting of
lower alkyl that is substituted by the group consisting of aryl, aryloxy, heteroaryl, heteroaryloxy, substituted aryl, substituted aryloxy, substituted heteroaryl, and substituted heteroaryloxy, and optionally also may be substituted by the group consisting of $R^{13}$, perfluoroalkyl, cycloalkyl which optionally may be substituted by the group consisting of lower alkyl and $R^{13}$, and heterocycle which optionally may be substituted by the group consisting of lower alkyl and $R^{13}$,
and wherein the substitutents on the substituted aryl, substituted aryloxy, substituted heteroaryl, and substituted heteroaryloxy are selected from the group consisting of
$R^{13}$,
lower alkyl which optionally may be substituted by $R^{13}$,
cycloalkyl which optionally may be substituted by $R^{13}$, and
heterocycle which optionally may be substituted by $R^{13}$;
aryl which optionally may be substituted by the group consisting of
$R^{13}$,
perfluoroalkyl,
lower alkyl which optionally may be substituted by $R^{13}$,
cycloalkyl which optionally may be substituted by $R^{13}$, and
heterocycle which optionally may be substituted by $R^{13}$; and
heteroaryl which optionally may be substituted by the group consisting of
$R^{13}$,
perfluoroalkyl,
lower alkyl which optionally may be substituted by $R^{13}$,
cycloalkyl which optionally may be substituted by $R^{13}$, and
heterocycle which optionally may be substituted by $R^{13}$;

$R^2$ is selected from the group consisting of
—H,
—$OR^4$,
—$OCOR^4$,
—$COR^4$,
—$COOR^4$,
—$CONR^6R^7$,
—$NR^6R^7$,
halogen,
—$NO_2$,
—CN,
—$SO_2R^4$,
—$SO_2NR^6R^7$,
—perfluoroalkyl, and
—lower alkyl which optionally may be substituted by —$OR^8$ or —$NR^6R^7$;

$R^3$ is selected from the group consisting of
—H,
—$OR^4$,
—$COR^4$,
—$COOR^4$,
—$CONR^6R^7$,
halogen,
—CN
—$NR^6R^7$,
—perfluoroalkyl, and
lower alkyl which optionally may be substituted by —$OR^8$ or —$NR^6R^7$;

$R^4$ is selected from the group consisting of
—H,
lower alkyl which optionally may be substituted by the group consisting of —$OR^5$, —$COOR^8$, —$COR^8$, —$CONR^8R^9$, —$NR^6R^7$, cycloalkyl, heterocycle, —CN, —$NO_2$, —$SO_2R^8$, and —$SO_2NR^8R^9$,
cycloalkyl which optionally may be substituted by the group consisting of —$OR^5$, —$COOR^8$, —$COR^8$, —$CONR^8R^9$, —$NR^6R^7$, lower alkyl, heterocycle, —CN, —$NO_2$, —$SO_2R^8$, and —$SO_2NR^8R^9$,
heterocycle which optionally may be substituted by the group consisting of —$OR^5$, —$COOR^8$, —$COR^8$, —$CONR^8R^9$, —$NR^6R^7$, lower alkyl, cycloalkyl, —CN, —$NO_2$, —$SO_2R^8$, and —$SO_2NR^8R^9$,
aryl which optionally may be substituted by the group consisting of —$OR^5$, —$COOR^8$, —$COR^8$, —$CONR^8R^9$, —$NR^6R^7$, cycloalkyl, heterocycle, —CN, —$NO_2$, —$SO_2R^8$, —$SO_2NR^8R^9$, and halogen,
heteroaryl which optionally may be substituted by the group consisting of —$OR^5$, —$COOR^8$, —$COR^8$, —$CONR^8R^9$, —$NR^6R^7$, cycloalkyl, heterocycle, —CN, —$NO_2$, —$SO_2R^8$, —$SO_2NR^8R^9$, and halogen;

$R^5$ is selected from the group consisting of
—H,
—$COR^8$,
—$CONR^8R^9$, and
—lower alkyl which optionally may be substituted by the group consisting of —$OR^9$, —$NR^9R^{10}$, —$N(COR^9)R^{10}$, —$COR^9$, —$CONR^9R^{10}$, —$SR^9$ and —$COOR^9$;

$R^6$ and $R^7$ are each independently selected from the group consisting of
—H,
—$COR^8$,
—$COOR^8$,
—$CONR^8R^9$,
—$SO_2R^8$,
—$SO_2NR^8R^9$,
lower alkyl which optionally may be substituted by the group consisting of —$OR^5$, —$NR^8R^9$, —$COOR^8$, —$COR^8$, —$CONR^8R^9$, —CN, —$NO_2$, —$SO_2R^8$, —$SO_2NR^8R^9$,
cycloalkyl which optionally may be substituted by the group consisting of —$OR^5$, —$COOR^8$, —$COR^8$, —$CONR^8R^9$, —$NR^8R^9$, lower alkyl, heterocycle, —CN, —NO₂, —SO₂R⁸, and
—SO₂NR⁸R⁹,
  heterocycle which optionally may be substituted by
    the group consisting of —OR⁵, —COOR⁸,
    —COR⁸, —CONR⁸R⁹, —NR⁸R⁹, lower alkyl,
    cycloalkyl, —CN, —NO², —SO₂R⁸, and
    —SO₂NR⁸R⁹,
  aryl which optionally may be substituted by the
    group consisting of —OR⁵, —COOR⁸, —COR⁸,
    —CONR⁸R⁹, —NR⁸R⁹, lower alkyl, cycloalkyl,
    heterocycle, —CN, —NO₂, —SO₂R⁸, and
    —SO₂NR⁸R⁹, and
  heteroaryl which optionally may be substituted by
    the group consisting of —OR⁵, —COOR⁸,
    —COR⁸, —CONR⁸R⁹, —NR⁸R⁹, lower alkyl,
    cycloalkyl, heterocycle, —CN, —NO₂, —SO₂R⁸,
    and —SO₂NR⁸R⁹;
  cycloalkyl which optionally may be substituted by the
    group consisting of —OR⁵, —COOR⁸, —COR⁸,
    —CONR⁸R⁹, —NR⁸R⁹, lower alkyl, heterocycle,
    —CN, —NO₂, —SO₂R⁸, and —SO₂NR⁸R⁹;
  heterocycle which optionally may be substituted by the
    group consisting of —OR⁵, —COOR⁸, —COR⁸,
    —CONR⁸R⁹, —NR⁸R⁹, lower alkyl, cycloalkyl,
    —CN, —NO₂, —SO₂R⁸, and —SO₂NR⁸R⁹;
  aryl which optionally may be substituted by the group
    consisting of —OR⁵, —COOR⁸, —COR⁸,
    —CONR⁸R⁹, —NR⁸R⁹, lower alkyl, cycloalkyl,
    heterocycle, —CN, —NO₂, —SO₂R⁸, and
    —SO₂NR⁸R⁹; and
  heteroaryl which optionally may be substituted by the
    group consisting of —OR⁵, —COOR⁸, —COR⁸,
    —CONR⁸R⁹, —NR⁸R⁹, lower alkyl, cycloalkyl,
    heterocycle, —CN, —NO₂, —SO₂R⁸, and
    —SO₂NR⁸R⁹; or
  alternatively, —NR⁶R⁷ can optionally form a ring
    having 3 to 7 atoms, said ring optionally including
    one or more additional hetero atoms and being
    optionally substituted by the group consisting of
    lower alkyl, —OR⁵, —COR⁸, —COOR⁸,
    —CONR⁸R⁹, and —NR⁵R⁹;
R⁸ is selected from the group consisting of
—H,
  lower alkyl which optionally may be substituted by the
    group consisting of cycloalkyl, heterocycle, aryl,
    heteroaryl, —OR⁹, NR⁹R¹⁰, and —N(COR⁹)R¹⁰,
  aryl which optionally may be substituted by the group
    consisting of —OR⁹, —COOR⁹, —COR⁹,
    —CONR¹⁰R⁹, —NR¹⁰R⁹, lower alkyl, cycloalkyl,
    heterocycle, —CN, —NO₂, —SO₂R⁹, and
    —SO₂NR¹⁰R⁹, and
  heteroaryl which optionally may be substituted by the
    group consisting of —OR⁹, —COOR⁹, —COR⁹,
    —CONR¹⁰R⁹, —NR¹⁰R⁹, lower alkyl, cycloalkyl,
    heterocycle, —CN, —NO₂, —SO₂R⁹, and
    —SO₂NR¹⁰R⁹;
  cycloalkyl which optionally may be substituted by the
    group consisting of —OR⁹, —COOR⁹, —COR⁹,
    —CONR¹⁰R⁹, —NR¹⁰R⁹, lower alkyl, heterocycle,
    —CN, —NO₂, —SO₂R⁹, and —SO₂NR¹⁰R⁹;
  heterocycle which optionally may be substituted by the
    group consisting of —OR⁹, —COOR⁹, —COR⁹,
    —CONR¹⁰R⁹, —NR¹⁰R⁹, lower alkyl, cycloalkyl,
    —CN, —NO₂, —SO₂R⁹, and —SO₂NR¹⁰R⁹;
R⁹ and R¹⁰ are each independently selected from the
group consisting of
—H and lower alkyl;

R¹³ is selected from the group consisting of
  halogen,
  —OR⁴,
  —OCOR⁴,
  —COR⁴
  —COOR⁴,
  —CONR⁶R⁷,
  —NO₂,
  —NR⁶R⁷,
  —CN,
  —SO₂R⁴, and
  —SO₂NR⁶R⁷;
X is selected from the group consisting of
  —N— and —C—; and
a is an optional bond.
  In another embodiment, the invention is directed to
5-alkynyloxindoles and 5-alkenyloxindoles having the formula:

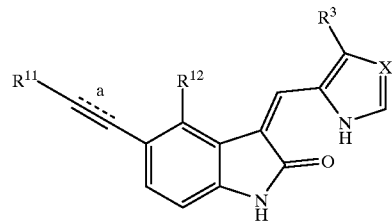

II wherein R³ through R¹⁰, X and "a" are as defined above;
  and
R¹¹ is selected from the group consisting of
  —H,
  —COR⁴,
  —COOR⁴,
  —CONR⁶R⁷,
  lower alkyl which optionally may be substituted by the
    group consisting of —OR⁵, —NR⁶R⁷, halogen,
    —NO₂, —SO₂R⁴, —SO₂NR⁶R⁷, —CN, —COR⁴,
    —COOR⁴, —CONR⁶R⁷, cycloalkyl, heterocycle,
    aryl, and heteroaryl,
  cycloalkyl, which optionally may be substituted by the
    group consisting of —OR⁵, —NR⁶R⁷, halogen,
    —NO₂, —SO₂R⁴, —SO₂NR⁶R⁷, —CN, —COR⁴,
    —COOR⁴, —CONR⁶R⁷, lower alkyl, heterocycle,
    aryl, and heteroaryl,
  heterocycle, which optionally may be substituted by the
    group consisting of —OR⁵, —NR⁶R⁷, halogen,
    —NO₂, —SO₂R⁴, —SO₂NR⁶R⁷, —CN, —COR⁴,
    —COOR⁴, —CONR⁶R⁷, lower alkyl, cycloalkyl,
    aryl, and heteroaryl,
  aryl, which optionally may be substituted by the group
    consisting of —OR⁵, —NR⁶R⁷, halogen, —NO₂,
    —SO₂R⁴, —SO₂NR⁶R⁷, —CN, —COR⁴,
    —COOR⁴, —CONR⁶R⁷, lower alkyl, and
    perfluoroalkyl, and
  heteroaryl, which optionally may be substituted by the
    group consisting of —OR⁵, —NR⁶R⁷, halogen,
    —NO₂, —SO₂R⁴, —SO₂NR⁶R⁷, —CN, —COR⁴,
    —COOR⁴, —CONR⁶R⁷, lower alkyl, and perfluoroalkyl; and
R¹² is selected from the group consisting of
  —H,
  —OR⁴,
  —OCOR⁴,
  —COR⁴

—COOR⁴,
—CONR⁶R⁷,
—NR⁶R⁷,
—halogen,
—NO₂,
—CN,
—SO₂R⁴,
—SO₂NR⁶R⁷,
—perfluoroalkyl,
lower alkyl which optionally may be substituted from the group consisting of —OR⁴, —NR⁶R⁷, cycloalkyl, heterocycle, —COR⁴, —COOR⁴, —CONR⁶R⁷, —CN, —NO₂, —SO₂R⁴, —SO₂NR⁶R⁷ and halogen,
cycloalkyl which optionally may be substituted from the group consisting of —OR⁴, —NR⁶R⁷, lower alkyl, heterocycle, —COR⁴, —COOR⁴, —CONR⁶R⁷, —CN, —NO₂, —SO₂R⁴, —SO₂NR⁶R⁷ and halogen, and
heterocycle which optionally may be substituted from the group consisting of —OR⁴, —NR⁶R⁷, lower alkyl, cycloalkyl, —COR⁴, —COOR⁴, —CONR⁶R⁷, —CN, —NO₂, —SO₂R⁴, —SO₂NR⁶R⁷ and halogen.

The present invention is further directed to pharmaceutical compositions comprising a pharmaceutically effective amount of any one or more of the above-described compounds and a pharmaceutically acceptable carrier or excipient.

The present invention is also directed to a method for treating and/or controlling inflammatory diseases and neurodegenerative diseases, in particular, the treatment or control of rheumatoid arthritis, by administering to a human patient in need of such therapy an effective amount of a compound of formula I or II, prodrugs of such compounds and/or salts thereof.

The present invention is also directed to intermediates useful in the preparation of the above-described 4- and 5-alkynyloxindoles and 4- and 5-alkenyloxindoles.

DETAILED DESCRIPTION OF THE INVENTION

Definitions

As used herein, the following terms shall have the following definitions.

"Aryl" means an aromatic group having 5 to 10 atoms and consisting of 1 or 2 rings.

"Aryloxy" means an aryl radical that includes at least one oxygen and which is attached to rest of molecule via the oxygen atom.

"Cycloalkyl" means a non-aromatic, partially or completely saturated cyclic aliphatic hydrocarbon group containing 3 to 8 atoms. Examples of cycloalkyl groups include cyclopropyl, cyclopentyl and cyclohexyl.

"Effective Amount" means an amount of at least one compound of formula I and/or II, or a pharmaceutically acceptable salt, prodrug or metabolite thereof, that inhibits the development or proliferation of (1) an inflammatory disease or response and/or (2) a neuro-degenerative disease or response, such as for example, and not as a limitation, rheumatoid arthritis.

"Halogen" means fluorine, chlorine, bromine or iodine.

"Heteroaryl" groups are aromatic groups having 5 to 10 atoms, one or 2 rings, and containing one or more hetero atoms. Examples of heteroaryl groups are 2-, 3- or 4-pyridyl, tetrazolyl, oxadiazolyl, pyrazinyl and quinolyl.

"Heteroaryloxy" means a heteroaryl radical that includes at least one oxygen and which is attached to rest of molecule via the oxygen atom.

"Hetero atom" means an atom selected from N, O and S.

"Heterocycle" means a 3- to 10-membered non-aromatic, partially or completely saturated hydrocarbon group, such as tetrahydroquinolyl, which contains one or two rings and at least one hetero atom.

"IC₅₀" refers to the concentration of a particular 4- or 5-alkynyloxindole or 4- or 5-alkenyloxindole required to inhibit 50% of cJun phosphorylation, which is a measure of inhibition of SAPK activity. IC₅₀ can be measured, inter alia, using the assay described herein in Example 102.

"Lower Alkyl" denotes a straight-chain or branched saturated aliphatic hydrocarbon having 1 to 6, preferably 1 to 4, carbon atoms. Typical lower alkyl groups include methyl, ethyl, propyl, isopropyl, butyl, t-butyl, 2-butyl, pentyl, hexyl and the like.

"Pharmaceutically acceptable salt" refers to conventional acid-addition salts or base-addition salts which retain the biological effectiveness and properties of the compounds of formula I or II and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from sodium, potassium, ammonium, and quaternary ammonium hydroxide, such as for example tetramethylammonium hydroxide.

"Pharmaceutically acceptable," such as pharmaceutically acceptable carrier, excipient, prodrug, etc., means pharmacologically acceptable and substantially non-toxic to the subject to which the particular compound is administered.

"Pharmaceutically active metabolite" means a metabolic product of a compound of formula I or II which is pharmaceutically acceptable and effective.

"Prodrug" refers to a compound that may be converted under physiological conditions or by solvolysis to any of the compounds of formula I or II or to a pharmaceutically acceptable salt of a compound of formula I or II. A prodrug may be inactive when administered to a subject but is converted in vivo to an active compound of formula I or II.

"Substituted," as in substituted alkyl means that the substitution can occur at one or more positions, that one or more substituents may be selected, and, unless otherwise indicated, that the substituents are independently selected from the specified options.

The Compounds

In one embodiment, the current invention is directed to compounds having the formula:

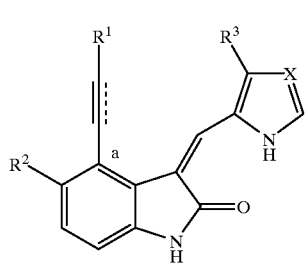

I and prodrugs and pharmaceutically active metabolites of compounds of formula I, and the pharmaceutically acceptable salts of all of the foregoing compounds,
wherein:

$R^1$ is selected from the group consisting of
  lower alkyl that is substituted by the group consisting of aryl, aryloxy, heteroaryl, heteroaryloxy, substituted aryl, substituted aryloxy, substituted heteroaryl, and substituted heteroaryloxy, and optionally also may be substituted by the group consisting of $R^{13}$, perfluoroalkyl, cycloalkyl which optionally may be substituted by the group consisting of lower alkyl and $R^{13}$, and heterocycle which optionally may be substituted by the group consisting of lower alkyl and $R^{13}$,
  and wherein the substitutents on the substituted aryl, substituted aryloxy, substituted heteroaryl, and substituted heteroaryloxy are selected from the group consisting of
    $R^{13}$,
    lower alkyl which optionally may be substituted by $R^{13}$,
    cycloalkyl which optionally may be substituted by $R^{13}$, and
    heterocycle which optionally may be substituted by $R^{13}$;
  aryl which optionally may be substituted by the group consisting of
    $R^{13}$,
    perfluoroalkyl,
    lower alkyl which optionally may be substituted by $R^{13}$,
    cycloalkyl which optionally may be substituted by $R^{13}$, and
    heterocycle which optionally may be substituted by $R^{13}$; and
  heteroaryl which optionally may be substituted by the group consisting of
    $R^{13}$,
    perfluoroalkyl,
    lower alkyl which optionally may be substituted by $R^{13}$,
    cycloalkyl which optionally may be substituted by $R^{13}$, and
    heterocycle which optionally may be substituted by $R^{13}$;
$R^2$ is selected from the group consisting of
  —H,
  —$OR^4$,
  —$OCOR^4$,
  —$COR^4$,
  —$COOR^4$,
  —$CONR^6R^7$,
  —$NR^6R^7$
  halogen,
  —$NO_2$,
  —CN,
  —$SO_2R^4$,
  —$SO_2NR^6R^7$,
  —perfluoroalkyl, and
  —lower alkyl which optionally may be substituted by —$OR^8$ or —$NR^6R^7$;
$R^3$ is selected from the group consisting of
  —H,
  —$OR^4$,
  —$COR^4$,
  —$COOR^4$,
  —$CONR^6R^7$,
  halogen,
  —CN
  —$NR^6R^7$,
  —perfluoroalkyl, and
  lower alkyl which optionally may be substituted by —$OR^8$ or —$NR^6R^7$;
$R^4$ is selected from the group consisting of
  —H,
  lower alkyl which optionally may be substituted by the group consisting of —$OR^5$, —$COOR^8$, —$COR^8$, —$CONR^8R^9$, —$NR^6R^7$, cycloalkyl, heterocycle, —CN, —$NO_2$, —$SO_2R^8$, and —$SO_2NR^8R^9$,
  cycloalkyl which optionally may be substituted by the group consisting of —$OR^5$, —$COOR^8$, —$COR^8$, —$CONR^8R^9$, —$NR^6R^7$, lower alkyl, heterocycle, —CN, —$NO_2$, —$SO_2R^8$, and —$SO_2NR^8R^9$,
  heterocycle which optionally may be substituted by the group consisting of —$OR^5$, —$COOR^8$, —$COR^8$, —$CONR^8R^9$, —$NR^6R^7$, lower alkyl, cycloalkyl, —CN, —$NO_2$, —$SO_2R^8$, and —$SO_2NR^8R^9$,
  aryl which optionally may be substituted by the group consisting of —$OR^5$, —$COOR^8$, —$COR^8$, —$CONR^8R^9$, —$NR^6R^7$, cycloalkyl, heterocycle, —CN, —$NO_2$, —$SO_2R^8$, —$SO_2NR^8R^9$, and halogen,
  heteroaryl which optionally may be substituted by the group consisting of —$OR^5$, —$COOR^8$, —$COR^8$, —$CONR^8R^9$, —$NR^6R^7$, cycloalkyl, heterocycle, —CN, —$NO_2$, —$SO_2R^8$, —$SO_2NR^8R^9$, and halogen;
$R^5$ is selected from the group consisting of
  —H,
  —$COR^8$,
  —$CONR^8R^9$, and
  —lower alkyl which optionally may be substituted by the group consisting of —$OR^9$, —$NR^9R^{10}$, —$N(COR^9)R^{10}$, —$COR^9$, —$CONR^9R^{10}$, —$SR^9$ and —$COOR^9$;
$R^6$ and $R^7$ are each independently selected from the group consisting of
  —H,
  —$COR^8$,
  —$COOR^8$,
  —$CONR^8R^9$,
  —$SO_2R^8$,
  —$SO_2NR^8R^9$,
  lower alkyl which optionally may be substituted by the group consisting of —$OR^5$, —$NR^8R^9$, —$COOR^8$, —$COR^8$, —$CONR^8R^9$, —CN, —$NO_2$, —$SO_2R^8$, —$SO_2NR^8R^9$,
  cycloalkyl which optionally may be substituted by the group consisting of —$OR^5$, —$COOR^8$, —$COR^8$, —$CONR^8R^9$, —$NR^8R^9$, lower alkyl, heterocycle, —CN, —$NO_2$, —$SO_2R^8$, and —$SO_2NR^8R^9$,
  heterocycle which optionally may be substituted by the group consisting of —$OR^5$, —$COOR^8$, —$COR^8$, —$CONR^8R^9$, —$NR^8R^9$, lower alkyl, cycloalkyl, —CN, —$NO_2$, —$SO_2R^8$, and —$SO_2NR^8R^9$,
  aryl which optionally may be substituted by the group consisting of —$OR^5$, —$COOR^8$, —$COR^8$, —$CONR^8R^9$, —$NR^8R^9$, lower alkyl, cycloalkyl, heterocycle, —CN, —$NO_2$, —$SO_2R^8$, —$SO_2NR^8R^9$, and
  heteroaryl which optionally may be substituted by the group consisting of —$OR^5$, —$COOR^8$, —$COR^8$, —$CONR^8R^9$, —$NR^8R^9$, lower alkyl, cycloalkyl, heterocycle, —CN, —$NO_2$, —$SO_2R^8$, and —$SO_2NR^8R^9$;

cycloalkyl which optionally may be substituted by the group consisting of —$OR^5$, —$COOR^8$, —$COR^8$, —$CONR^8R^9$, —$NR^8R^9$, lower alkyl, heterocycle, —CN, —$NO_2$, —$SO_2R^8$, and —$SO_2NR^8R^9$;

heterocycle which optionally may be substituted by the group consisting of —$OR^5$, —$COOR^8$, —$COR^8$, —$CONR^8R^9$, —$NR^8R^9$, lower alkyl, cycloalkyl, —CN, —$NO_2$, —$SO_2R^8$, and —$SO_2NR^8R^9$;

aryl which optionally may be substituted by the group consisting of —$OR^5$, —$COOR^8$, —$COR^8$, —$CONR^8R^9$, —$NR^8R^9$, lower alkyl, cycloalkyl, heterocycle, —CN, —$NO_2$, —$SO_2R^8$, and —$SO_2NR^8R^9$; and heteroaryl which optionally may be substituted by the group consisting of —$OR^5$, —$COOR^8$, —$COR^8$, —$CONR^8R^9$, —$NR^8R^9$, lower alkyl, cycloalkyl, heterocycle, —CN, —$NO_2$, —$SO_2R^8$, and —$SO_2NR^8R^9$; or alternatively, —$NR^6R^7$ can optionally form a ring having 3 to 7 atoms, said ring optionally including one or more additional hetero atoms and being optionally substituted by the group consisting of lower alkyl, —$OR^5$, —$COR^8$, —$COOR^8$, —$CONR^8R^9$, and —$NR^5R^9$;

$R^8$ is selected from the group consisting of
—H,
lower alkyl which optionally may be substituted by the group consisting of cycloalkyl, heterocycle, aryl, heteroaryl, —$OR^9$, —$NR^9R^{10}$, and —$N(COR^9)R^{10}$,
aryl which optionally may be substituted by the group consisting of —$OR^9$, —$COOR^9$, —$COR^9$, —$CONR^{10}R^9$, —$NR^{10}R^9$, lower alkyl, heterocycle, —CN, —$NO_2$, —$SO_2R^9$, and —$SO_2NR^{10}R^9$, and
heteroaryl which optionally may be substituted by the group consisting of —$OR^9$, —$COOR^9$, —$COR^9$, —$CONR^{10}R^9$, —$NR^{10}R^9$, lower alkyl, cycloalkyl, heterocycle, —CN, —$NO_2$, —$SO_2R^9$, and —$SO_2NR^{10}R^9$;
cycloalkyl which optionally may be substituted by the group consisting of —$OR^9$, —$COOR^9$, —$COR^9$, —$CONR^{10}R^9$, —$NR^{10}R^9$, lower alkyl, heterocycle, —CN, —$NO_2$, —$SO_2R^9$, and —$SO_2NR^{10}R^9$;
heterocycle which optionally may be substituted by the group consisting of —$OR^9$, —$COOR^9$, —$COR^9$, —$CONR^{10}R^9$, —$NR^{10}R^9$, lower alkyl, cycloalkyl, —CN, —$NO_2$, —$SO_2R^9$, and —$SO_2NR^{10}R^9$;

$R^9$ and $R^{10}$ are each independently selected from the group consisting of
—H and lower alkyl;

$R^{13}$ is selected from the group consisting of
halogen,
—$OR^4$,
—$OCOR^4$,
—$COR^4$,
—$COOR^4$,
—$CONR^6R^7$,
—$NO_2$,
$NR^6R^7$,
—CN,
—$SO_2R^4$, and
—$SO_2NR^6R^7$;

X is selected from the group consisting of
—N— and —C—; and a is an optional bond.

In a preferred embodiment of the compounds of formula I, $R^1$ is selected from the group consisting of lower alkyl that is substituted by the group consisting of aryl and substituted aryl, and optionally also substituted by the group consisting of halogen, —$OR^4$, —$COR^4$, —$COOR^4$, —$CONR^6R^7$, cycloalkyl, heterocycle, —$NR^6R^7$, cycloalkyl which is substituted by the group consisting of —$OR^4$ and —$NR^6R^7$, —$COOR^4$, —$CONR^6R^7$, and heterocycle which is substituted by the group consisting of —$OR^4$, —$NR^6R^7$, —$COOR^4$, —$CONR^6R^7$; and wherein the substituents on the substituted aryl are selected from the group consisting of halogen, —$OR^4$, —$COR^4$, —$COOR^4$, —$CONR^6R^7$, —$NO_2$, —$NR^6R^7$, —$SO_2R^4$, —$SO_2NR^6R^7$, —CN, perfluoroalkyl, lower alkyl, cycloalkyl, heterocycle, lower alkyl which is substituted by the group consisting of —$OR^4$, —$NR^6R^7$, —$COOR^4$, —$CONR^6R^7$, cycloalkyl which is substituted by the group consisting of —$OR^4$, —$NR^6R^7$, —$COOR^4$, —$CONR^6R^7$, and heterocycle which is substituted by the group consisting of —$OR^4$, —$NR^6R^7$, —$COOR^4$, —$CONR^6R^7$;

lower alkyl that is substituted by the group consisting of heteroaryl and substituted heteroaryl, and optionally also substituted by the group consisting of halogen, —$OR^4$, —$COR^4$, —$COOR^4$, —$CONR^6R^7$, cycloalkyl, heterocycle, cycloalkyl which is substituted by the group consisting of —$OR^4$, —$COOR^4$, —$CONR^6R^7$, and —$NR^6R^7$, and heterocycle which is substituted by the group consisting of —$OR^4$, —$COOR^4$, —$CONR^6R^7$, and —$NR^6R^7$; and wherein the substituents on the substituted heteroaryl are selected from the group consisting of halogen, —$OR^4$, —$COR^4$, —$COOR^4$, —$NR^6R^7$, —$SO_2R^4$, —$SO_2NR^6R^7$, —$NO_2$, —CN, —$CONR^6R^7$, lower alkyl, cycloalkyl, heterocycle, lower alkyl which is substituted by the group consisting of —$OR^4$, —$NR^6R^7$, —$COOR^4$, —$CONR^6R^7$, cycloalkyl which is substituted by the group consisting of —$OR^4$, —$NR^6R^7$, —$COOR^4$, $CONR^6R^7$, and heterocycle which is substituted by the group consisting of —$OR^4$ and —$NR^6R^7$, —$COOR^4$, —$CONR^6R^7$;

aryl which optionally is substituted by the group consisting of halogen, —$OR^4$, —$COR^4$, —$COOR^4$, —$CONR^6R^7$, lower alkyl, cycloalkyl, heterocycle, lower alkyl which is substituted by the group consisting of —$OR^4$, —$NR^6R^7$, —$COOR^4$, —$CONR^6R^7$, cycloalkyl which is substituted by the group consisting of —$OR^4$, —$COOR^4$, —$CONR^6R^7$, and —$NR^6R^7$, and heterocycle which is substituted by the group consisting of —$OR^4$, —$COOR^4$, —$CONR^6R^7$, and —$NR^6R^7$;

heteroaryl which optionally is substituted by the group consisting of halogen, —$OR^4$, —$COR^4$, —$COOR^4$, —$CONR^6R^7$, lower alkyl, cycloalkyl, heterocycle, lower alkyl which is substituted by the group consisting of —$OR^4$, —$COOR^4$, —$CONR^6R^7$, and —$NR^6R^7$, cycloalkyl which is substituted by the group consisting of —$OR^4$, —$COOR^4$, —$CONR^6R^7$, and —$NR^6R^7$, and heterocycle which is substituted by the group consisting of —$OR^4$, —$COOR^4$, —$CONR^6R^7$, and —$NR^6R^7$.

In another preferred embodiment of the compounds of formula I, $R^1$ is

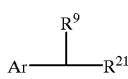

wherein Ar is aryl which optionally may be substituted by one or more substituent independently selected from the group consisting of —H,
—OR$^4$,
—COR$^4$,
—COOR$^4$,
—CONR$^6$R$^7$,
halogen,
—CN
—NR$^6$R$^7$, and
lower alkyl which optionally may be substituted by —OR$^4$, —COOR$^4$, —CONR$^6$R$^7$, or —NR$^6$R$^7$;
R$^9$ is as defined above, and
R$^{21}$ is selected from the group consisting of
—OR$^4$, and
—NR$^6$R$^7$.
In another preferred embodiment of the compounds of formula I, R$^1$ is

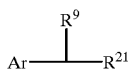

wherein Ar is heteroaryl which optionally may be substituted by one or more substituents independently selected from the group consisting of
—H,
—OR$^4$,
—COR$^4$,
—COOR$^4$,
—CONR$^6$R$^7$,
halogen,
—CN,
—NR$^6$R$^7$, and
lower alkyl which optionally may be substituted by —OR$^4$, —COOR$^4$, —CONR$^6$R$^7$, or —NR$^6$R$^7$.

In another preferred embodiment of the compounds of formula I, R$^1$ is Ar' wherein Ar' is selected from the group consisting of aryl and heteroaryl, each of which optionally may be substituted by the group consisting of
—H,
—OR$^4$,
—COR$^4$,
COOR$^4$,
—CONR$^6$R$^7$,
halogen,
—CN,
—NR$^6$R$^7$, and
lower alkyl which optionally may be substituted by —OR$^4$ or —NR$^6$R$^7$.

In another preferred embodiment of the compounds of formula I, R$^2$ is selected from the group consisting of
—H,
—OR$^4$,
—COOR$^4$,
—CONR$^6$R$^7$,
—NR$^6$R$^7$,
halogen,
—NO$_2$, and
—CN;

In another preferred embodiment of the compounds of formula I, R$^3$ is selected from the group consisting of
—H,
—OR$^4$,
—NR$^6$R$^7$, and
lower alkyl which optionally may be substituted by the group consisting of —OR$^8$ and —NR$^6$R$^7$;

In another preferred embodiment of the compounds of formula I, R$^4$ is selected from the group consisting of
—H,
lower alkyl which optionally may be substituted by one or more —OR$^5$, —COOR$^8$, —COR$^8$ and —CONR$^8$R$^9$,
cycloalkyl which optionally may be substituted by one or more —OR$^5$, —COOR$^8$, —COR$^8$ and —CONR$^8$R$^9$, and
heterocycle which optionally may be substituted by one or more —OR$^5$, —COOR$^8$, —COR$^8$ and —CONR$^8$R$^9$;

In another preferred embodiment of the compounds of formula I, R$^5$ is selected from the group consisting of
—H,
—COR$^8$,
—CONR$^8$R$^9$, and
lower alkyl;

In another preferred embodiment of the compounds of formula I, R$^6$ and R$^7$ are each independently selected from the group consisting of
—H,
—COR$^8$,
—COOR$^8$,
—CONR$^8$R$^9$, and
lower alkyl which optionally may be substituted by the group consisting of —OR$^9$ and —NR$^8$R$^9$, —COOR$^8$, —CONR$^8$R$^9$; or
alternatively, —NR$^6$R$^7$ can optionally form a ring having 3 to 7 atoms, said ring optionally including one or more additional hetero atoms and being optionally substituted by the group consisting of lower alkyl, —OR$^5$, —COR$^8$, —COOR$^8$, —CONR$^8$R$^9$, and —NR$^5$R$^9$;

In another preferred embodiment of the compounds of formula I, R$^8$ is selected from the group consisting of
—H and lower alkyl which optionally may be substituted by the group consisting of aryl, heteroaryl, —OR$^9$, —COOR$^9$, —CONR$^9$R$^{10}$, and —NR$^9$R$^{10}$.

In another preferred embodiment of the compounds of formula I, "a" is a bond.

In another embodiment, the invention is directed to 5-alkynyloxindoles and 5-alkenyloxindoles having the formula:

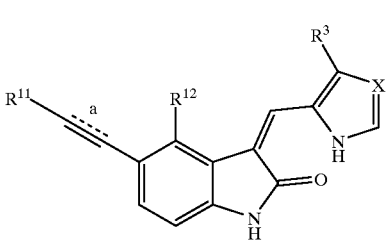

II wherein R$^3$ through R$^{10}$, X and "a" are as defined above; and R$^{11}$ is selected from the group consisting of
—H,
—COR$^4$,
—COOR$^4$,
—CONR$^6$R$^7$,
lower alkyl which optionally may be substituted by the group consisting of —OR$^5$, —NR$^6$R$^7$, halogen, —NO$_2$, —SO$_2$R$^4$, —SO$_2$NR$^6$R$^7$, —CN, —COR$^4$, —COOR$^4$, —CONR$^6$R$^7$, cycloalkyl, heterocycle, aryl, and heteroaryl, cycloalkyl, which optionally may be substituted by the group consisting of —OR$^5$, —NR$^6$R$^7$, halogen, —NO$_2$, —SO$_2$R$^4$, —SO$_2$NR$^6$R$^7$, —CN, —COR$^4$, —COOR$^4$, —CONR$^6$R$^7$, lower alkyl, heterocycle, aryl, and heteroaryl, heterocycle, which optionally may be substituted by the group consisting of —OR$^5$, —NR$^6$R$^7$, halogen, —NO$_2$, —SO$_2$R$^4$, —SO$_2$NR$^6$R$^7$, —CN, —COR$^4$, —COOR$^4$, —CONR$^6$R$^7$, lower alkyl, cycloalkyl, aryl, and heteroaryl, aryl, which optionally may be substituted by the group consisting of —OR$^5$, —NR$^6$R$^7$, halogen, —NO$_2$, —SO$_2$R$^4$, —SO$_2$NR$^6$R$^7$, —CN, —COR$^4$, —COOR$^4$, —CONR$^6$R$^7$, lower alkyl, and perfluoroalkyl, and heteroaryl, which optionally may be substituted by the group consisting of —OR$^5$, —NR$^6$R$^7$, halogen, —NO$_2$, —SO$_2$R$^4$, —SO$_2$NR$^6$R$^7$, —CN, —COR$^4$, —COOR$^4$, —CONR$^6$R$^7$, lower alkyl, and perfluoroalkyl; and R$^{12}$ is selected from the group consisting of
- —H,
- —OR$^4$,
- —OCOR$^4$,
- —COR$^4$,
- —COOR$^4$,
- —CONR$^6$R$^7$,
- —NR$^6$R$^7$,
- —halogen,
- —NO$_2$,
- —CN,
- —SO$_2$R$^4$,
- —SO$_2$NR$^6$R$^7$,
- —perfluoroalkyl,
- lower alkyl which optionally may be substituted from the group consisting of —OR$^4$, —NR$^6$R$^7$, cycloalkyl, heterocycle, —COR$^4$, —COOR$^4$, —CONR$^6$R$^7$, —CN, —NO$_2$, —SO$_2$R$^4$, —SO$_2$NR$^6$R$^7$ and halogen,
- cycloalkyl which optionally may be substituted from the group consisting of —OR$^4$, —NR$^6$R$^7$, lower alkyl, heterocycle, —COR$^4$, —COOR$^4$, —CONR$^6$R$^7$, —CN, —NO$_2$, —SO$_2$R$^4$, —SO$_2$NR$^6$R$^7$ and halogen, and
- heterocycle which optionally may be substituted from the group consisting of —OR$^4$, —NR$^6$R$^7$, lower alkyl, cycloalkyl, —COR$^4$, —COOR$^4$, —CONR$^6$R$^7$, —CN, —NO$_2$, —SO$_2$R$^4$, —SO$_2$NR$^6$R$^7$ and halogen.

The preferred embodiments for groups R$^3$ through R$^{10}$ for compounds of formula I are also preferred embodiment for these groups for compounds of formula II.

In another preferred embodiment of the compounds of formula II, R$^{11}$ is aryl which optionally may be substituted by the group consisting of —OR$^5$ and —NR$^6$R$^7$.

In another preferred embodiment of the compounds of formula II, R$^{11}$ is selected from the group consisting of
- —H,
- —COR$^4$,
- —COOR$^4$,
- —CONR$^6$R$^7$,
- lower alkyl which optionally may be substituted from the group consisting of —OR$^4$, —NR$^6$R$^7$, cycloalkyl, heterocycle, —COR$^4$, —COOR$^4$, —CONR$^6$R$^7$, —CN, —NO$_2$, —SO$_2$R$^4$, —SO$_2$NR$^6$R$^7$ and halogen,
- cycloalkyl which optionally may be substituted from the group consisting of —OR$^4$, —NR$^6$R$^7$, lower alkyl, heterocycle, —COR$^4$, —COOR$^4$, —CONR$^6$R$^7$, —CN, —NO$_2$, —SO$_2$R$^4$, —SO$_2$NR$^6$R$^7$ and halogen, and
- heterocycle which optionally may be substituted from the group consisting of —OR$^4$, —NR$^6$R$^7$, lower alkyl, cycloalkyl, —COR$^4$, —COOR$^4$, —CONR$^6$R$^7$, —CN, —NO$_2$, —SO$_2$R$^4$, —SO$_2$NR$^6$R$^7$ and halogen.

The following are preferred intermediates useful in the preparation of compounds of formula I:

1,3-Dihydro-5-fluoro-4-iodo-2H-indol-2-one, (Z)-1,3-Dihydro-3-[(1H-pyrrol-2-yl)methylene]-5-(trimethylsilyl)ethynyl-2H-indol-2-one, (Z)-5-Bromo-1,3-dihydro-3-[(3-methoxy-1H-pyrrol-2-yl)methylene]-2H-indol-2-one, (Z)-1,3-Dihydro-3-[(3-methoxy-1H-pyrrol-2-yl)methylene]-5-(trimethylsilyl)ethynyl-2H-indol-2-one, (Z)-5-Bromo-1,3-dihydro-3-[(4-methyl-1H-imidazol-5-yl)methylene]-2H-indol-2-one, (Z)-1,3-Dihydro-3-[(4-methyl-1H-imidazol-5-yl)methylene]-5-(trimethylsilyl)ethynyl-2H-indol-2-one.

The following are preferred compounds of formula I:

(Z)-1,3-Dihydro-4-(phenylethynyl)-3-[(3-methoxy-1H-pyrrol-2-yl)methylene]-2H-indol-2-one (D), (Z)-1,3-Dihydro-4-[(4-methoxyphenyl)ethynyl]-3-[(3-methoxy-1H-pyrrol-2-yl)methylene]-2H-indol-2-one (G), rac-(Z)-1,3-Dihydro-4-[3-hydroxy-3-(4-methoxyphenyl)-1-propynyl]-3-[(3-methoxy-1H-pyrrol-2-yl)methylene]-2H-indol-2-one (H), rac-(Z)-1,3-Dihydro-4-[3-hydroxy-3-(3-hydroxyphenyl)-1-propynyl]-3-[(3-methoxy-1H-pyrrol-2-yl)methylene]-2H-indol-2-one (I), rac-(Z)-1,3-Dihydro-4-[3-hydroxy-3-(3-methoxyphenyl)-1-propynyl]-3-[(3-methoxy-1H-pyrrol-2-yl)methylene]-2H-indol-2-one (J), rac-(Z)-4-[3-[2,3-Dihydro-3-[(3-methoxy-1H-pyrrol-2-yl)methylene]-2-oxo-1H-indol-4-yl]-1-hydroxy-2-propynyl]benzoic acid methyl ester (K), rac-(Z)-4-[3-[2,3-Dihydro-3-[(3-methoxy-1H-pyrrol-2-yl)methylene]-2-oxo-1H-indol-4-yl]-1-hydroxy-2-propynyl]benzoic acid (L), rac-(Z)-1,3-Dihydro-4-[3-hydroxy-3-(2-methoxyphenyl)-1-propynyl]-3-[(3-methoxy-1H-pyrrol-2-yl)methylene]-2H-indol-2-one (M), rac-(Z)-4-[3-(1,3-benzodioxol-5-yl)-3-hydroxy-1-propynyl]-1,3-dihydro-3-[(3-methoxy-1H-pyrrol-2-yl)methylene]-2H-indol-2-one (N), rac-(Z)-1,3-Dihydro-4-[3-hydroxy-3-(4-hydroxy-3-methoxyphenyl)-1-propynyl]-3-[(3-methoxy-1H-pyrrol-2-yl)methylene]-2H-indol-2-one (O), rac-(Z)-1,3-Dihydro-4-[3-hydroxy-3-(4-hydroxyphenyl)-1-propynyl]-3-[(3-methoxy-1H-pyrrol-2-yl)methylene]-2H-indol-2-one (Q), rac-(Z)-1,3-Dihydro-4-[3-(4-dimethylaminophenyl)-3-hydroxy-1-propynyl]-3-[(3-methoxy-1H-pyrrol-2-yl)methylene]-2H-indol-2-one (R), rac-(Z)-1,3-Dihydro-4-[3-hydroxy-3-(4-phenoxyphenyl)-1-propynyl]-3-[(3-methoxy-1H-pyrrol-2-yl)methylene]-2H-indol-2-one (S), rac-(Z)-1,3-Dihydro-4-[3-hydroxy-3-phenyl-1-butynyl]-3-[(3-methoxy-1H-pyrrol-2-yl)methylene]-2H-indol-2-one (T), rac-(Z)-1,3-Dihydro-4-[3-[4-(3-dimethylaminopropoxy)-phenyl]-3-hydroxy-1-propynyl]-3-[(3-methoxy-1H-pyrrol-2-yl)methylene]-2H-indol-2-one (V), rac-(Z)-1,3-Dihydro-4-[3-(2,3-dimethoxyphenyl)-3-hydroxy-1-propynyl]-3-[(3-methoxy-1H-pyrrol-2-yl)methylene]-2H-indol-2-one (EE), rac-(Z)-1,3-Dihydro-4-[3-(3,4-dimethoxyphenyl)-3-hydroxy-1-propynyl]-3-[(3-methoxy-1H-pyrrol-2-yl)methylene]-2H-indol-2-one (FF), rac-(Z)-1,3-Dihydro-4-[3-hydroxy-3-(3-hydroxy-4-methoxyphenyl)-1-propynyl]-3-[(3-methoxy-1H-pyrrol-2-yl)methylene]-2H-indol-2-one (HH), rac-(Z)-1,3-Dihydro-4-[3-hydroxy-3-[3-methoxy-4-[2-(4-morpholinyl)-ethoxy]-phenyl]-1-propynyl]-3-[(3-methoxy-1H-pyrrol-2-yl)methylene]-2H-indol-2-one (MM), rac-(Z)-1,3-Dihydro-4-[3-hydroxy-3-[3-methoxy-4-[2-(4-morpholinyl)-ethoxy]-phenyl]-1-propynyl]-3-[(3-methoxy-1H-pyrrol-2-yl)methylene]-2H-indol-2-one hydrochloride salt (NN), rac-(Z)-1,3-Dihydro-4-[3-hydroxy-3-(2,4,5-trimethoxyphenyl)-1-propynyl]-3-[(3-methoxy-1H-pyrrol-2-yl)methylene]-2H-indol-2-one (PP), rac-(Z)-[4-[3-[2,3-Dihydro-3-[(3-methoxy-1H-pyrrol-2-yl)methylene]-2-oxo-1H-indol-4-yl]-1-hydroxy-2-propynyl]-2-methoxyphenoxy]acetic acid methyl ester (QQ), rac-(Z)-[4-[3-[2,3-Dihydro-3-[(3-methoxy-1H-pyrrol-2-yl)methylene]-2-oxo-1H-indol-4-yl]-1-hydroxy-2-propynyl]-2-methoxyphenoxy]acetic acid (RR), rac-(Z)-4-[3-hydroxy-3-(4-methoxy-1,3-benzodioxol-6-yl)-1-propynyl]-1,3-dihydro-3-[(3-methoxy-1H-pyrrol-2-yl)methylene]-2H-indol-2-one (SS), rac-(Z)-1,3-Dihydro-4-[3-hydroxy-3-[4-[2-(4-morpholinyl)-ethoxy]-phenyl]-1-propynyl]-3-[(3-methoxy-1H-pyrrol-2-yl)methylene]-2H-indol-2-one (TT), rac-(Z)-4-[3-(4-Chloro-2-methylsulfanylmethoxy-phenyl)-3-hydroxy-1-propynyl]-1,3-dihydro-3-[(3-methoxy-1H-pyrrol-2-yl)methylene]-2H-indol-2-one (UU), rac-(Z)-4-[3-(3-Chlorophenyl)-3-hydroxy-1-propynyl]-1,3-dihydro-3-[(3-methoxy-1H-pyrrol-2-yl)methylene]-2H-indol-2-one (WW), rac-(Z)-[4-[3-[2,3-dihydro-3-[(3-methoxy-1H-pyrrol-2-yl)methylene]-2-oxo-1H-indol-4-yl]-1-hydroxy-2-propynyl]phenoxy]acetic acid 1,1-dimethylethyl ester (XX), rac-(Z)-[4-[3-[2,3-dihydro-3-[(3-methoxy-1H-pyrrol-2-yl)methylene]-2-oxo-1H-indol-4-yl]-1-hydroxy-2-propynyl]phenoxy]acetic acid (YY), rac-(Z)-1,3-Dihydro-4-[3-hydroxy-3-(3-nitrophenyl)-1-propynyl]-3-[(3-methoxy-1H-pyrrol-2-yl)methylene]-2H-indol-2-one (ZZ), rac-(Z)-4-[3-(3-Aminophenyl)-3-hydroxy-1-propynyl]-1,3-dihydro-3-[(3-methoxy-1H-pyrrol-2-yl)methylene]-2H-indol-2-one (AAA), rac-(Z)-4-[3-(4-Acetamidophenyl)-3-hydroxy-1-propynyl]-1,3-dihydro-3-[(3-methoxy-1H-pyrrol-2-yl)methylene]-2H-indol-2-one (BBB), rac-(Z)-1,3-Dihydro-4-(3-hydroxy-3-phenyl-1-propynyl)-3-[(3-methoxy-1H-pyrrol-2-yl)methylene]-2H-indol-2-one (FFF), rac-(Z)-1,3-Dihydro-4-[3-hydroxy-3-(3-pyridinyl)-1-propynyl]-3-[(3-methoxy-1H-pyrrol-2-yl)methylene]-2H-indol-2-one (X), Synthesis of rac-(Z)-1,3-Dihydro-4-[3-hydroxy-3-(1-methyl-pyrrol-2-yl)-1-propynyl]-3-[(3-methoxy-1H-pyrrol-2-yl)methylene]-2H-indol-2-one (AA), rac-(Z)-1,3-Dihydro-4-[3-hydroxy-3-(thiophen-3-yl)-1-propynyl]-3-[(3-methoxy-1H-pyrrol-2-yl)methylene]-2H-indol-2-one (BB), rac-(Z)-1,3-Dihydro-4-[3-hydroxy-3-(1H-pyrrol-2-yl)-1-propynyl]-3-[(3-methoxy-1H-pyrrol-2-yl)methylene]-2H-indol-2-one (DD), rac-(Z)-1,3-Dihydro-4-[3-hydroxy-3-(2-pyridinyl)-1-propynyl]-3-[(3-methoxy-1H-pyrrol-2-yl)methylene]-2H-indol-2-one (JJ), rac-(Z)-1,3-Dihydro-4-[3-hydroxy-3-(2-thiophenyl)-1-propynyl]-3-[(3-methoxy-1H-pyrrol-2-yl)methylene]-2H-indol-2-one (KK), rac-(Z)-1,3-Dihydro-4-[3-hydroxy-3-(3-methoxy-2-thiophenyl)-1-propynyl]-3-[(3-methoxy-1H-pyrrol-2-yl)methylene]-2H-indol-2-one (OO), rac-(Z)-1,3-Dihydro-4-[3-(2-furanyl)-3-hydroxy-1-propynyl]-3-[(3-methoxy-1H-pyrrol-2-yl)methylene]-2H-indol-2-one (VV), (Z)-1,3-Dihydro-3-[(3-methoxy-1H-pyrrol-2-yl)methylene]-4-(3-phenoxy-1-propynyl)-2H-indol-2-one (Y), (Z)-1,3-Dihydro-3-[(3-methoxy-1H-pyrrol-2-yl)methylene]-4-[(3-pyridinyl)ethynyl]-2H-indol-2-one (CCC), (Z)-1,3-Dihydro-3-[(3-methoxy-1H-pyrrol-2-yl)methylene]-4-[(2-pyridinyl)ethynyl]-2H-indol-2-one (DDD), (Z)-1,3-Dihydro-3-[(3-methoxy-1H-pyrrol-2-yl)methylene]-4-[(4-pyridinyl)ethynyl]-2H-indol-2-one (EEE), (Z)-1,3-Dihydro-3-[(3-methoxy-1H-pyrrol-2-yl)methylene]-5-nitro-4-[(3-pyridinyl)ethynyl]-2H-indol-2-one (GGG), (Z)-5-Amino-1,3-dihydro-3-[(3-methoxy-1H-pyrrol-2-yl)methylene]-4-[(3-pyridinyl)ethynyl]-2H-indol-2-one (HHH), (Z)-N-[2,3-Dihydro-3-[(3-methoxy-1H-pyrrol-2-yl)methylene]-2-oxo-4-[(3-pyridinyl)ethynyl]-1H-indol-5-yl]-2-thiopheneacetamide (III), 4-[(E)-2-(2-Chlorophenyl)-ethenyl]-1,3-dihydro-(Z)-3-[(1H-pyrrol-2-yl)methylene]-2H-indol-2-one (KKK), 1,3-Dihydro-(Z)-3-[(1H-pyrrol-2yl)methylene]-[(E)-2-phenylethenyl]-2H-indol-2-one (LLL), 1,3-Dihydro-(Z)-3-[(3-methoxy-1H-pyrrol-2yl)methylene]-[(E)-2-phenylethenyl]-2H-indol-2-one (MMM), 1,3-Dihydro-4-[(E)-2-(4-methoxyphenyl)-ethenyl]-(Z)-3-[(1H-pyrrol-2yl)methlene]-2H-indol-2-one (NNN), 1,3-Dihydro-(Z)-3-[(3-methoxy-1H-pyrrol-2-yl)methylene]-4-[(E)-2-(4-methoxy-phenyl)-ethenyl]-2H-indol-2-one (OOO), 4-[(E)-2-[2,3-Dihydro-(Z)-3-[(3-methoxy-1H-pyrrol-2-yl)methylene]-2-oxo-1H-indol-4-yl]ethenyl]benzoic acid methyl ester (PPP), 1,3-Dihydro-4-[(E)-2-(3,4-dimethoxyphenyl)-ethenyl]-(Z)-3-[(3-methoxy-1H-pyrrol-2-yl)methylene]-2H-indol-2-one (QQQ), (Z)-1,3-Dihydro-5-ethynyl-3-[(1H-pyrrol-2-yl)methylene]-2H-indol-2-one (SSS).

(Z)-1,3-Dihydro-5-(4-hydroxyphenyl)ethynyl-3-[(1H-pyrrol-2-yl)methylene]-2H-indol-2-one (TTT), (Z)-1,3-Dihydro-5-(3-nitrophenyl)ethynyl-3-[(1H-pyrrol-2-yl)methylene]-2H-indol-2-one (UUU),
(Z)-1,3-Dihydro-5-phenylethynyl-3-[(1H-pyrrol-2-yl)methylene]-2H-indol-2-one (VVV),
(Z)-1,3-Dihydro-5-(3-hydroxyphenyl)ethynyl-3-[(1H-pyrrol-2-yl)methylene]-2H-indol-2-one (WWW),
(Z)-1,3-Dihydro-5-(2-nitrophenyl)ethynyl-3-[(1H-pyrrol-2-yl)methylene]-2H-indol-2-one (XXX),
(Z)-1,3-Dihydro-5-(4-nitrophenyl)ethynyl-3-[(1H-pyrrol-2-yl)methylene]-2H-indol-2-one (ZZZ),
(Z)-5-(4-Aminophenyl)ethynyl-1,3-dihydro-3-[(1H-pyrrol-2-yl)methylene]-2H-indol-2-one (AAAA),
(Z)-1,3-Dihydro-5-ethynyl-3-[(3-methoxy-1H-pyrrol-2-yl)methylene]-2H-indol-2-one (DDDD),
(Z)-1,3-Dihydro-5-(3-pyridinyl)ethynyl-3-[(1H-pyrrol-2-yl)methylene]-2H-indol-2-one (EEEE),
(Z)-1,3-Dihydro-5-(2-pyridinyl)ethynyl-3-[(1H-pyrrol-2-yl)methylene]-2H-indol-2-one (FFFF),
(Z)-1,3-Dihydro-5-(4-hydroxyphenyl)ethynyl-3-[(3-methoxy-1H-pyrrol-2-yl)-methylene]-2H-indol-2-one (GGGG),
(Z)-1,3-Dihydro-5-(4-methoxyphenyl)ethynyl-3-[(1H-pyrrol-2-yl)-methylene]-2H-indol-2-one (HHHH),
(Z)-1,3-Dihydro-3-[(1H-pyrrol-2-yl)-methylene]-5-(2-thiophenyl)ethynyl-2H-indol-2-one (IIII),
(Z)-1,3-Dihydro-5-ethynyl-3-[(4-methyl-1H-imidazol-5-yl)methylene]-2H-indol-2-one, trifluoroacetate salt (LLLL).

The compounds disclosed herein and covered by the above formulae may exhibit tautomerism or structural isomerism. It is intended that the invention encompasses any tautomeric or structural isomeric form of these compounds, or mixtures of such forms, and is not limited to any one tautomeric or structural isomeric form utilized within the formulae drawn above.

General Synthesis Schemes

The compounds of formulas I and II may be prepared by processes known in the art. Suitable processes for synthesizing these compounds are provided in the examples. Generally, these compounds may be prepared according to the following synthesis schemes.

Compounds of Formula I: Scheme I

General Step 1

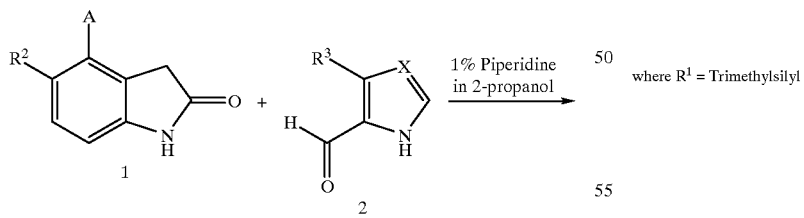

General Step 2a

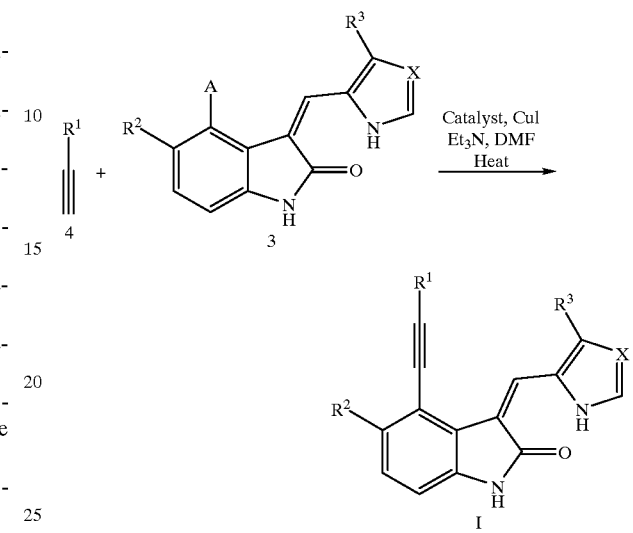

where A = Br or I, X = N or C

General Step 2b

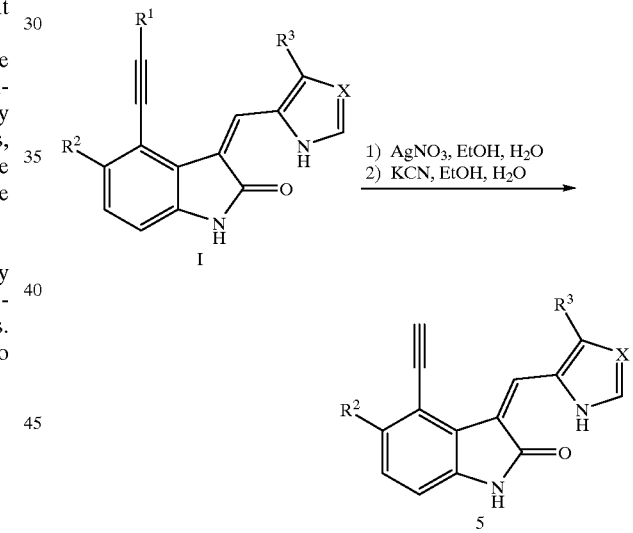

where $R^1$ = Trimethylsilyl

General Step 2C

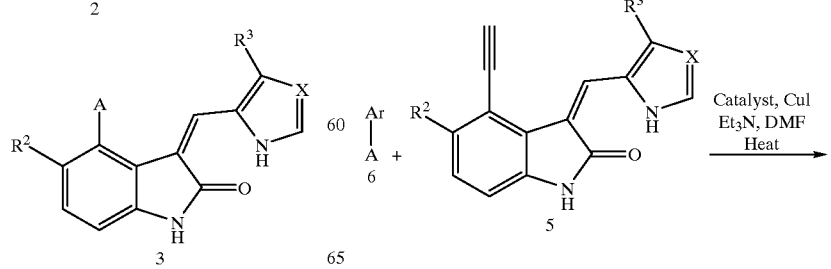

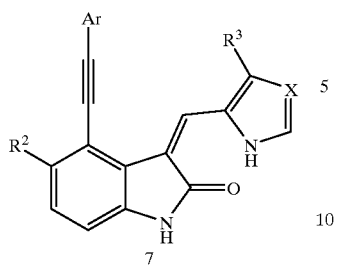

where A = Br or I, Ar = aryl or heteroaryl, X = N or C

Compounds 1 and 2 are either available from commercial sources or are synthesized by methods known in the art. Compounds 1 and 2 are reacted in piperidine to yield compound 3. When $R^1$ of the compound to be synthesized is other than Ar, compound 3 is then reacted with compound 4, which is also either available from commercial sources or is synthesized by methods known in the art, to yield compound I. See, General Step 2a. When $R^1$ of the product to be synthesized is Ar, then compound I wherein $R^1$ is trimethylsilyl is further reacted with AgNO$_3$ and KCN in accordance with General Step 2b to yield compound 5. In accordance with General Step 2c, compound 5 is then reacted with compound 6, which is either available from commercial sources or is synthesized by methods known in the art, to yield compound 7.

Compounds of Formula II: Scheme II

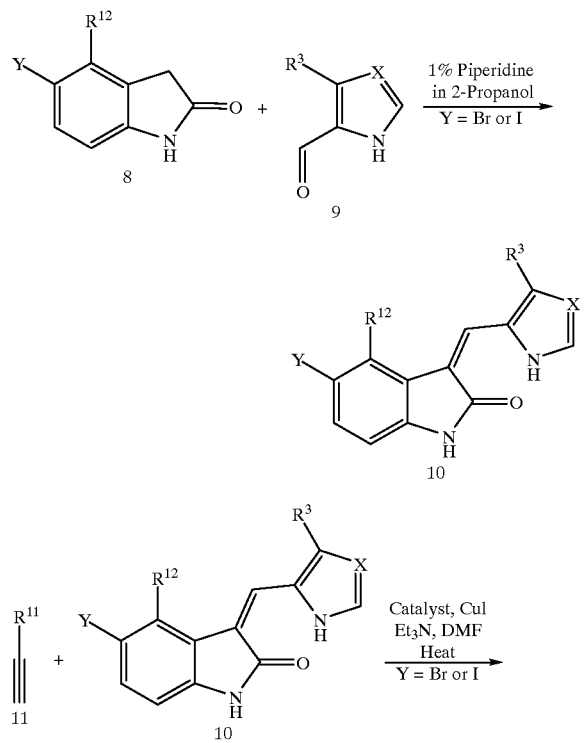

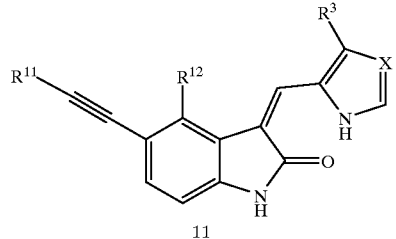

Compounds of formula 8 and 9 are available from commercial sources. These compounds are reacted in piperidine in an appropriate solvent to yield a compound of formula 10. Compounds of formula 10 are then reacted with a compound of formula 11, which is also commercially available, to yield a compound of formula II.

Compositions/Formulations

In an alternative embodiment, the present invention is directed to pharmaceutical compositions comprising at least one compound of formula I or II or a prodrug thereof, or a pharmaceutically acceptable salt of a compound of formula I or II or a prodrug of such compound.

These pharmaceutical compositions can be administered orally, for example, in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of formula I or II, prodrugs of such compounds, or the salts thereof, may be manufactured in a manner that is know in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, maize starch or derivatives thereof, talc, steric acid or its salts can be used as such carriers for tablets, coated tablets, dragees and hard gelatin capsules. Suitable carriers for soft gelatin capsules are vegetable oils, waxes, fats, semi-solid or liquid poll. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerin, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I or II.

Dosages

As mentioned above, the compounds of formula I or II, prodrugs thereof, and their salts, and compositions containing these compounds are useful in the treatment or control of inflammatory diseases and neuro-degenerative diseases, in particular, in the treatment or control of rheumatoid arthritis.

A therapeutically effective amount of a compound in accordance with this invention means an amount of compound that is effective to prevent, alleviate or ameliorate symptoms of disease of the subject being treated. Determination of a therapeutically effective amount is within the skill in the art.

The therapeutically effective amount or dosage of a compound of formula I or II can vary within wide limits and will be adjusted to the individual requirements in each particular case. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

EXAMPLES

The compounds of the present invention may be synthesized according to known techniques, such as for example General Scheme I provided above. The following examples illustrate preferred methods for synthesizing the compounds and formulations of the present invention.

Example 1

General Synthesis Methods and Starting Materials
Method A: Preparation of 1-alkyl or 1-aryl-2-propyn-1-ols Via Grignard Addition to aldehydes

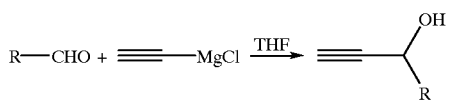

A solution of the appropriate aldehyde (4.0 mmol) in 30 mL dry tetrahydrofuran, under argon, was cooled to 0° C. with an ice bath. Ethynylmagnesium chloride (5 mmol, 0.5 M solution in THF) was added dropwise, and the solution was stirred at 0° C. or room temperature for 1 to 3 h. The reaction was quenched by the addition of a saturated ammonium chloride solution in water (15 mL), and the tetrahydrofuran was evaporated in vacuo. The residue was then extracted with ethyl acetate (3×30 mL), and the combined organic extracts were dried over magnesium sulfate, and concentrated in vacuo to yield the desired propargyl alcohol which was used in the coupling reaction without further purification.

Method B: Preparation of 1-alkyl or 1-aryl-2-propyn-1-ols Via Grignard Addition to aldehydes

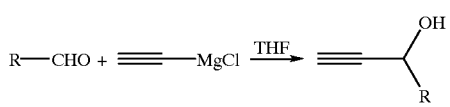

A solution of the appropriate aldehyde (4.0 mmol) in 30 mL dry tetrahydrofuran, under argon, was cooled to 0° C. with an ice bath. Ethynylmagnesium chloride (10 mmol, 0.5 M solution in THF) was added dropwise, and the solution was stirred at 0° C. or room temperature for 1 to 3 h. The reaction was quenched by the addition of a saturated ammonium chloride solution in water (15 mL), and the tetrahydrofuran was evaporated in vacuo. The residue was then extracted with ethyl acetate (3×30 mL), and the combined organic extracts were dried over magnesium sulfate, and concentrated in vacuo to yield the desired propargyl alcohol which was used in the coupling reaction without further purification.

Method C: Preparation of 4-alkynyloxindoles Via Palladium (0)-mediated Coupling

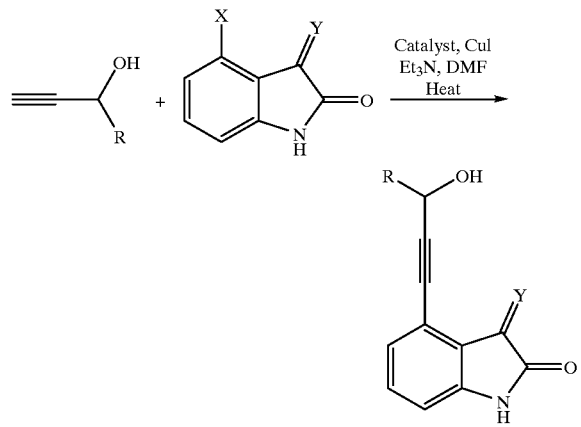

A solution of the appropriate 4-iodooxindole (4 mmol), and the appropriate alkyne (4.4 mmol) in 3 mL dimethylformamide and 3 mL triethylamine was degassed by bubbling argon through the solution for 15 minutes. At this time, copper (I) iodide (16 mg, 0.1 mmol) and palladium (0) catalyst (see Examples) (0.04 mmol) were added, and the reaction was heated, under argon, at a temperature between 60 to 90° C., for 6 to 96 hours. After cooling, water (20 mL) was added and the precipitate was filtered off and dried. The product was purified via either flash column chromatography ($SiO_2$, 230–400 mesh with ethyl acetate/hexane as solvent) or with reverse phase HPLC (using either acetonitrile/water or acetonitrile/water/trifluoroacetic acid as solvent).

Method D: Preparation of 4-alkynyloxindoles Via Palladium (0)-mediated Coupling

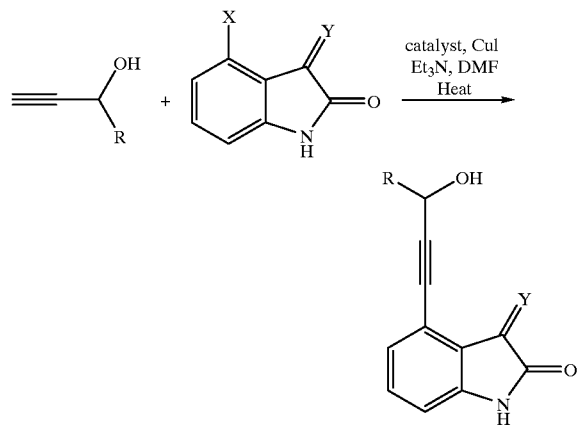

A solution of the appropriate 4-bromooxindole (4 mmol), and the appropriate alkyne (4.4 mmol) in 3 mL dimethylformamide and 3 mL triethylamine was degassed by bubbling argon through the solution for 15 minutes. At this time, copper (I) iodide (16 mg, 0.1 mmol) and catalyst (0.04 mmol) were added, and the reaction was heated, under argon, at between 60 to 90° C. for 6 to 96 hours. After cooling, water (20 mL) was added and the precipitate was filtered off and dried. The product was purified via either flash column chromatography ($SiO_2$, 230–400 mesh with ethyl acetate/hexane as solvent) or with reverse phase HPLC (using either acetonitrile/water or acetonitrile/water/ trifluoroacetic acid as solvent).

Method E: Preparation of Methyl Esters from Carboxylic Acids

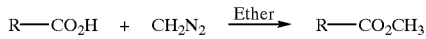

To a solution of the appropriate carboxylic acid (15.3 mmol) in diethyl ether (30 mL) was added a solution of diazomethane (20 mmol, 0.47 M in ether). The reaction was stirred at room temperature for 1 hour at which time a few drops of acetic acid was added. The solution was washed with saturated sodium bicarbonate (3×25 mL) and the solvent was evaporated to yield the desired methyl ester which was used without further purification.

Method F: Preparation of Carboxylic Acids from the Methyl Esters

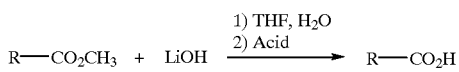

The appropriate methyl ester (0.14 mmol) was dissolved in a mixture of 2 mL tetrahydrofuran and 2 mL water. Lithium hydroxide (2.8 mmol, 20 equiv.) was added, and the reaction was stirred at room temperature from 1 to 96 hours. The tetrahydrofuran was then evaporated and 10 mL water was added. The aqueous layer was then extracted with ethyl acetate (2×10 mL) and the aqueous layer was then acidified to pH=2 with 1 N hydrochloric acid. The aqueous layer was then extracted with ethyl acetate (4×20 mL), and the combined organic extracts were washed with a saturated solution of sodium chloride and were then dried over magnesium sulfate. The ethyl acetate was then evaporated and the product was recrystallized from ethanol.

Method H: Mitsunobu Coupling of N-(2-hydroxyethyl) morpholine to Phenols

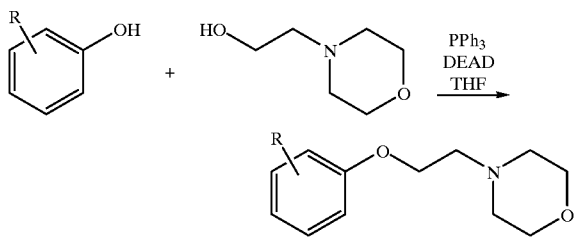

To a solution of the appropriate phenol (3.3 mmol), N-(2-hydroxyethyl)morpholine (4.9 mmol), and triphenylphosphine (5.0 mmol) in tetrahydrofuran (30 mL), under argon, was added via an addition funnel a solution of diethyl azodicarboxylate (5.0 mmol, 0.863 g) in 15 mL tetrahydrofuran. The reaction was stirred at room temperature for 14 hours at which time water (15 mL) was added and the tetrahydrofuran was evaporated. The aqueous layer was extracted with ethyl acetate (4×30 mL), and the combined organic extracts were washed with a saturated solution of sodium chloride, dried over magnesium sulfate and the solvent evaporated. The product was purified via flash column chromatography (SiO$_2$, 230–400 mesh) with ethyl acetate/hexane.

Method J: Preparation of 4-alkynyloxindoles Via Palladium (0)-mediated Coupling

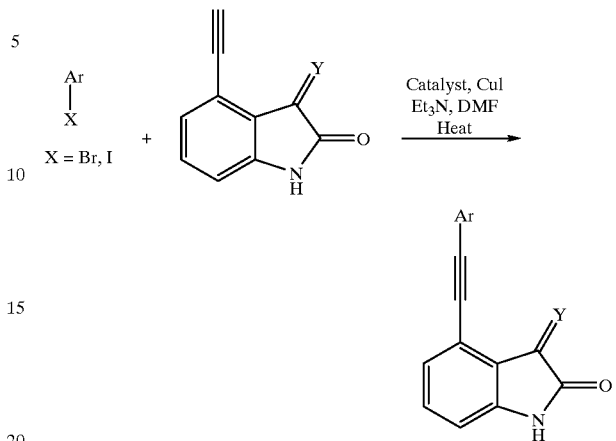

A solution of the appropriate 4-ethynyl-oxindole (4 mmol), and the appropriate aryl halide (4.4 mmol) in 3 mL dimethylformamide and 3 mL triethyl amine was degassed by bubbling argon through the solution for 15 minutes. At this time, copper (I) iodide (16 mg, 0.1 mmol) and palladium (0) catalyst (0.04 mmol) were added, and the reaction was heated, under argon, at between 60 to 90° C. for 12 to 96 hours. After cooling, water (20 mL) was added and the precipitate was filtered off and dried. The product was purified via either flash column chromatography (SiO$_2$, 230–400 mesh with ethyl acetate/hexane as solvent) or with reverse phase HPLC (using either acetonitrile/water or acetonitrile/water/trifluoroacetic acid as solvent).

Method K: Hydrolysis of Trimethylsilyl Alkyne to Alkyne

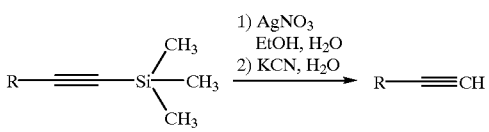

To a solution of the appropriate trimethylsilyl alkyne (4 mmol) in EtOH (80 mL), with addition of THF until complete dissolution if necessary, was added dropwise a solution of AgNO$_3$ (1.46 g, 8.59 mmol) in EtOH (5 mL) and water (15 mL). The mixture was stirred at room temperature for 1 h, then treated with a solution of KCN (2.71 g 41.6 mmol) in water (10 mL). After stirring for an additional 20 min, the reaction mixture was diluted with water (100 mL) and extracted with EtOAc (3×100 mL). Combined EtOAc layers was dried (MgSO$_4$) and concentrated to dryness under reduced pressure to yield the above-identified product.

Method L:

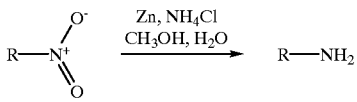

To a solution of nitro compound in 10% water in methanol was added Zn dust and NH$_4$Cl. The mixture was heated at reflux for 6 h then filtered through Celite® (Fisher Scientific). Filtrate was concentrated in vacuo. The product was purified via either flash column chromatography (SiO$_2$, 230–400 mesh with ethyl acetate/hexane as solvent) or with reverse phase HPLC (using either acetonitrile/water or acetonitrile/water/trifluoroacetic acid as solvent).

Method M:

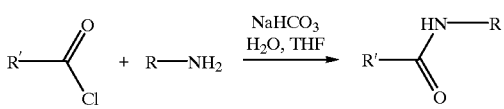

To a mixture of amino compound in THF and saturated aqueous NaHCO₃ was added a THF solution of the acid chloride dropwise. The mixture was stirred for 3 h to 10 days at room temperature then diluted with ethyl acetate. The phases were separated and the organic solution was washed with water then dried (MgSO₄). The product was purified via either flash column chromatography (SiO₂, 230–400 mesh with ethyl acetate/hexane as solvent) or with reverse phase HPLC (using either acetonitrile/water or acetonitrile/water/trifluoroacetic acid as solvent).

Method N: Preparation of 3-arylmethylene-substituted Oxindoles Via Coupling with Aldehyde

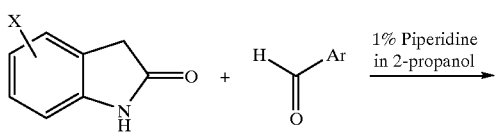

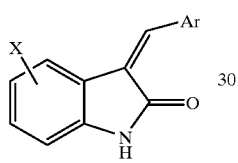

A solution or suspension of the appropriate oxindole (1 mmol), and excess aldehyde (1 to 2 mmol) in 2 mL of 1% piperidine in 2-propanol was heated at between 60 to 90° C. for 1 to 48 hours. Hot water (2 mL) was added. On cooling, the crystallized product was filtered off, washed with aqueous 2-propanol, and dried.

Starting Material 1: (Z)-4-Bromo-1,3-dihydro-3-[(3-methoxy-1H-pyrrol-2-yl)methylene]-2H-indol-2-one

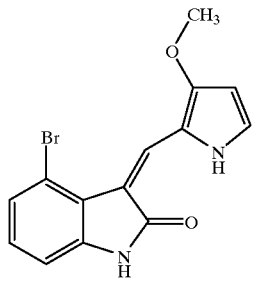

A mixture of 4-bromo-1,3-dihydro-2H-indol-2-one (100 mg, 0.47 mmol) (prepared according to T. Kosuge et al., *Chem. Pharm. Bull.* 33(4):1414–1418 (1985)), and excess 3-methoxy-2-pyrrolecarboxyaldehyde (70.8 mg, 0.57 mmol) (prepared according to F. Bellamy, *J. Chem. Research* (S) (1979) 18–19; *J. Chem. Research* (M) (1979) 0106–0116) in 1% piperidine in 2-propanol (1 mL) was heated at 85° C. for 2 h. Hot water (1 mL) was added. On cooling, the crystallized product was filtered off, washed with aqueous 2-propanol and dried. (Yield 0.13 g, 83%).

Starting Material 2: (Z)-1,3-Dihydro-4-iodo-3-[(3-methoxy-1H-pyrrol-2-yl)methylene]-2H-indol-2-one

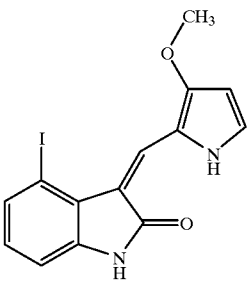

A mixture of 1,3-dihydro-4-iodo-2H-indol-2-one (prepared according to T. Fukuyama et al., *J. A. Chem. Soc.* 118:7426–7427 (1996)) (0.51 g, 1.97 mmol), and excess 3-methoxy-2-pyrrolecarboxyaldehyde (0.30 g, 2.36 mmol) (see Bellamy, supra) in 1% piperidine in 2-propanol (10 mL) was heated at 85° C. for 4 h. Hot water (10 mL) was added. On cooling, the crystallized product was filtered off, washed with aqueous 2-propanol and dried. (Yield 0.46 g, 64%).

Starting Material 3: (Z)-4-bromo-1,3-dihydro-3-[(3-methoxy-1H-pyrrol-2-yl)methylene]-5-nitro-2H-indol-2-one

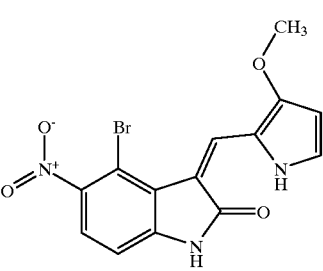

A mixture of 4-bromo-1,3-dihydro-5-nitro-2H-indol-2-one (from Example 4 infra) (0.113 g, 0.44 mmol), and excess 3-methoxy-2-pyrrolecarboxyaldehyde (66.3 mg, 0.53 mmol) (see Bellamy, supra) in 1% piperidine in 2-propanol (2 mL) was heated at 85° C. for 3 h. Hot water (2 mL) was added. On cooling, the crystallized product was filtered off, washed with aqueous 2-propanol and dried. (Yield 0.136 g, 85%).

Starting Material 4: (Z)-1,3-Dihydro-3-[(3-methoxy-1H-pyrrol-2-yl)methylene]-4-(2-trimethylsilyl-ethynyl)-2H-indol-2-one

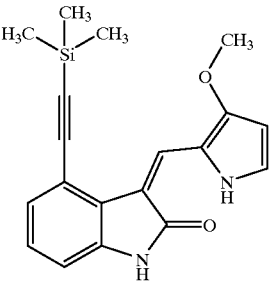

Trimethylsilyl acetylene (0.94 g, 9.63 mmol) (Aldrich) was coupled with (Z)-4-bromo-1,3-dihydro-3-[(3-methoxy-1H-pyrrol-2-yl)methylene]-2H-indol-2-one (2.05 g, 6.42 mmol) (Starting Material 1) using (Ph₃P)₂PdCl₂ (0.23 g)

(Aldrich) and CuI (61 mg), (Aldrich) as catalyst in DMF (15 mL) and Et₃N (15 mL) as solvent at 80° C. for 2 days in accordance with method D above. (Yield 1.3 g, 60%).

Starting Material 5: (Z)-1,3-Dihydro-4-ethynyl-3-[(3-methoxy-1H-pyrrol-2-yl)methylene]-2H-indol-2-one

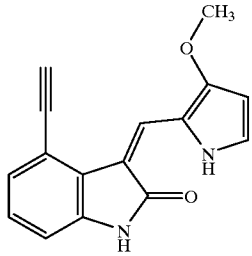

A solution of (Z)-1,3-dihydro-3-[(3-methoxy-1H-pyrrol-2-yl)methylene]-4-(2-trimethylsilyl-ethynyl)-2H-indol-2-one (1.3 g, 3.86 mmol) (Starting Material 4) in EtOH (80 mL) was treated with AgNO₃ (1.46 g, 8.59 mmol) in ethanol (5 mL) and water (15 mL) at room temperature for 1 h followed by KCN (2.71 g, 41.6 mmol) in water (10 mL) according to method K above. (Yield 1.02 g, 100%).

Starting Material 6: 5-Bromo-1,3-dihydro-2H-indol-2-one

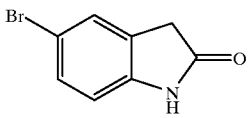

1,3-Dihydro-2H-indol-2-one (5.25 g, 39.43 mmol) (Aldrich) was treated with a 1:1 solution of glacial acetic acid and distilled water (246 mL). The resulting reaction mixture was cooled to 0° C. and then slowly treated with N-bromosuccinimide (14.03 g, 78.85 mmol) (J. T. Baker). After the complete addition of N-bromosuccinimide, the cooling bath was removed, and the reaction mixture was stirred at 23° C. for 1 h. Upon stirring at 23° C., the reaction mixture became viscous and a white solid precipitated. The reaction mixture was poured into 500 mL distilled water and filtered to provide a crude white solid. Recrystallization from methanol provided pure 5-bromo-1,3-dihydro-2H-indol-2-one as a light pink solid. (Yield 5.28 g, 63%; mp 219–220° C.).

Starting Material 7: (Z)-5-Bromo-1,3-dihydro-3-[(1H-pyrrol-2-yl)methylene]-2H-indol-2-one

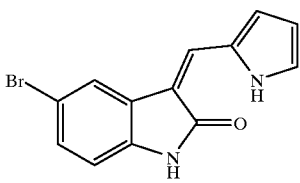

A mixture of 5-bromo-1,3-dihydro-2H-indol-2-one (3.10 g, 14.62 mmol) (Starting Material 6) and pyrrole-2-carboxaldehyde (1.46 g, 15.35 mmol) (Aldrich) in 2-propanol (73 mL) was treated with 10–12 drops of piperidne. The reaction mixture was heated at reflux for 20 h and then allowed to cool to 23° C., at which time, the reaction mixture was filtered. The resulting solid was washed well with hexanes, followed by petroleum ether, and then allowed to air dry to provide pure (Z)-5-bromo-1,3-dihydro-3-[(1H-pyrrol-2-yl)methylene]-2H-indol-2-one as a yellow solid which was used without further purification. (Yield 4.01 g, 95%; mp 267–268° C.).

Starting Material 8: (Z)-1,3-Dihydro-5-iodo-3-[(1H-pyrrol-2-yl)methylene]-2H-indol-2-one

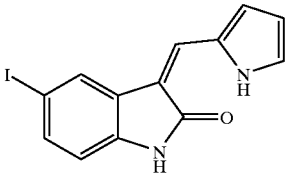

To a solution of [[1-[[(1,1-dimethylethyl)oxy]carbonyl]-1H-pyrrol-2-yl]methyl]triphenylphosphonium iodide (2.3 g, 4.0 mmol) (prepared according to the procedure of: V. H. Rawal et. al., *J. Org. Chem.* 1987, 52(1), 19–28) in 36 mL DMF at 0° C. under argon, was added slowly NaH (0.13 g, 5.4 mmol). The mixture was stirred at 0° C. for 45 min. The solution was then allowed to warm to room temperature and 5-iodoisatin (1.0 g, 3.66 mmol) was added. The solution was heated at reflux for 15 h, at which time acetone (1 mL) was added and the solvent mixture was evaporated. The residue was then purified via flash column chromatography (25% EtOAc/hex) to yield (Z)-1,3-dihydro-5-iodo-3-[(1H-pyrrol-2-yl)methylene]-2H-indol-2-one. (Yield 1.05 g, 83%).

Starting Material 9: (Z)-4-Bromo-1,3-dihydro-3-[(1H-pyrrol-2-yl)methylene]-2H-indol-2-one

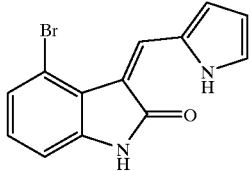

A mixture of 4-bromo-1,3-dihydro-2H-indol-2-one (0.2 g, 0.94 mmol) (see T. Kosuge et. al., *Chem. Pharm. Bull.* 33(4):1414–1418 (1985)), and excess pyrrole-2-carboxaldehyde (0.11 g, 1.13 mmol) (Aldrich) in 1% piperidine in 2-propanol (2 mL) was heated at 85° C. for 2 h. Hot water (2 mL) was added. On cooling, the crystallized product was filtered off, washed with aqueous 2-propanol and dried. (Yield 0.26 g, 96%)

Example 2

Synthesis of 1,3-Dihydro-5-fluoro-4-iodo-2H-indol-2-one (A)

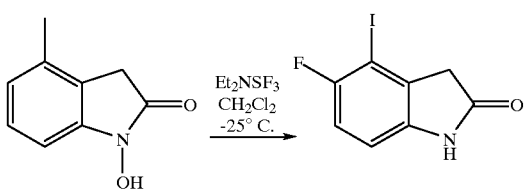

A suspension of 1,3-dihydro-1-hydroxy-4-iodo-2H-indol-2-one (2.43 g, 9 mmol) (prepared according to Kende et al., *Synth. Commun.* 20(14, 2133–2138 (1990)) in dry dichloromethane (500 mL) was cooled to −25° C. under an argon atmosphere with magnetic stirring. A solution of diethylaminosulfur trifluoride (DAST, 1.35 mL) (Aldrich) in dry dichloromethane (40 mL) was added dropwise at such a rate that the reaction temperature did not rise above −25° C. (about 15 min.) After stirring for an additional 30 min. at −25° C., the reaction was quenched by the addition of saturated aqueous sodium bicarbonate solution (180 mL) and allowed to warm to room temperature. The mixture was then filtered through Celite® (Fisher) and the layers separated. The aqueous layer was extracted with dichloromethane (2×300 mL). The dichloromethane layers were washed with saturated aqueous sodium chloride solution (200 mL), combined, dried (magnesium sulfate) and concentrated. The resulting residue was purified by flash chromatography on silics gel using ethyl acetate—dichloromethane (1:7, V/V) as solvent to give 1,3-dihydro-5-fluoro-4-iodo-2H-indol-2-one (Yield 1.08 g, 43%).

Example 3

Synthesis of 1,3-Dihydro-4-iodo-5-nitro-2H-indol-2-one (B)

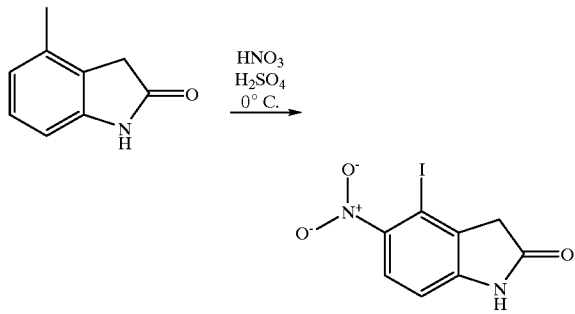

A mixture of concentrated sulfuric acid (0.73 mL) and concentrated nitric acid (0.14 mL) was added slowly to a solution of 1,3-dihydro-4-iodo-2H-indol-2-one (0.5 g, 1.93 mmol) (see Fukuyama, supra) in concentrated sulfuric acid (6 mL) at −5° C., with stirring. The mixture was stirred for an additional 15 min at −5° C., then poured onto ice. After standing for 1 h, solid was collected by filtration and washed with water, and dried in a vacuum oven to give 1,3-dihydro-4-iodo-5-nitro-2H-indol-2-one. (Yield 0.46 g, 78%).

Example 4

Synthesis of 4-Bromo-1,3-dihydro-5-nitro-2H-indol-2-one (C)

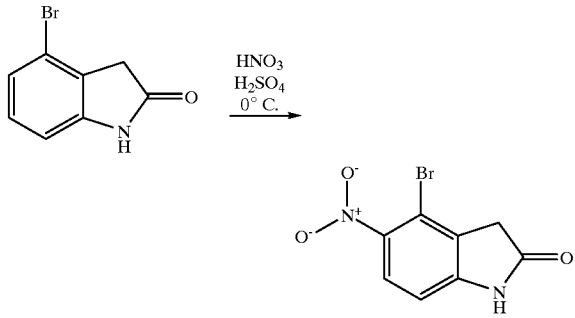

A mixture of concentrated sulfuric acid (3.6 mL) and concentrated nitric acid (0.7 mL) was added slowly to a solution of 4-bromo-1,3-dihydro -2H-indol-2-one (2 g, 9.48 mmol) (prepared according to T. Kosuge et al., *Chem. Pharm. Bull.* 33(4):1414–1418 (1985)) in concentrated sulfuric acid (20 mL) at −5° C., with stirring. The mixture was stirred for an additional 1 h at −5° C., then poured in ice. After standing for 1 h, precipitate formed was collected by filtration and washed with water, and dried in a vacuum oven to give 4-bromo-1,3-dihydro-5-nitro-2H-indol-2-one. (Yield 2.33 g, 96%).

Example 5

Synthesis of (Z)-1,3-Dihydro-4-(phenylethynyl)-3-[(3-methoxy-1H-pyrrol-2-yl)methylene]-2H-indol-2-one (D)

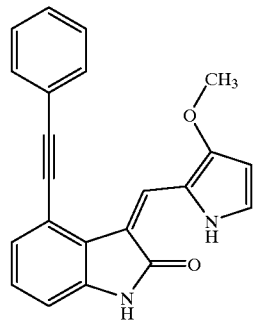

Using general Method D above, phenyl acetylene (32 mg, 0.31 mmol) (Aldrich) was coupled with (Z)-4-bromo-1,3-dihydro-3-[(3-methoxy-1H-pyrrol-2-yl)methylene]-2H-indol-2-one (50 mg, 0.16 mmol) (Starting Material 1) using DPPFPdCl$_2$ (6.5 mg) (Aldrich) and CuI (1.5 mg) (Aldrich) as catalyst in DMF (2 mL) and Et$_3$N (3 mL) as solvent at 85° C. for 18 h, to yield (Z)-1,3-dihydro-4-(phenylethynyl)-3-[(3-methoxy-1H-pyrrol-2-yl)methylene]-2H-indol-2-one. (Yield 20 mg, 37%)

Example 6

Synthesis of (Z)-1,3-Dihydro-4-(phenylethynyl)-3-[(1H-pyrrol-2-yl)methylene]-2H-indol-2-one (E)

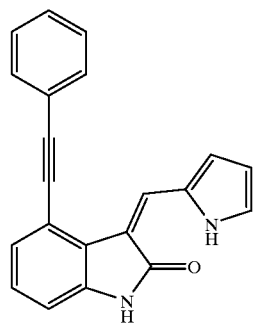

Using general Method D above, phenyl acetylene (32 mg, 0.31 mmol) (Aldrich) was coupled with (Z)-4-bromo-1,3-dihydro-3-[(1H-pyrrol-2-yl)methylene]-2H-indol-2-one (Starting Material 9) (46.3 mg, 0.16 mmol) using (Ph$_3$P)$_4$Pd (8 mg) (Aldrich) and CuI (1.5 mg) (Aldrich) as catalyst in DMF (2 mL) and Et$_3$N (3 mL) as solvent at 85° C. for 18 h, yielding (Z)-1,3-dihydro-4-(phenylethynyl)-3-[(1H-pyrrol-2-yl)methylene]-2H-indol-2-one. (Yield 41 mg, 83%)

Example 7

Synthesis of (Z)-5-[3-[2,3-dihydro-2-oxo-3-(1H-pyrrol-2-ylmethylene)-1H-indol-4-yl]-2-propynyl]-6(5H)-phenanthridinone (F)

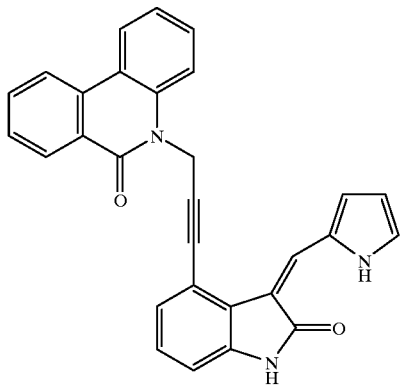

A solution of (Z)-1,3-dihydro-4-iodo-3-[(1H-pyrrol-2-yl)methylene]-2H-indol-2-one (from Example 71, infra) (50 mg, 0.15 mmol), and 5-(2-propynyl)-6(5H)-phenanthridinone (45 mg, 0.19 mmol) (prepared according to Walser et al., *J. Med. Chem.* 34(3), 1209–1221 (1991)) in 1 mL tetrahydrofuran and 1 mL triethylamine was degassed by bubbling argon through the solution for 10 minutes. At this time, copper (I) iodide (11 mg, 0.06 mmol) and tetrakis(triphenylphosphine) palladium(0) (3 mg, 0.03 mmol) were added, and the reaction was stirred at room temperature for 72 hours. Water (10 mL) was then added and the precipitate was filtered off and dried. The product was purified via flash column chromatography ($SiO_2$, 230–400 mesh) with ethyl acetate/hexane, to yield a yellow powder which was recrystallized from ethyl acetate/hexane, to give (Z)-5-[3-[2,3-dihydro-2-oxo- 3-(1H-pyrrol-2-ylmethylene)-1H-indol-4-yl]-2-propynyl]-6(5H)-phenanthridinone. (Yield 25 mg, 38%).

Example 8

Synthesis of (Z)-1,3-Dihydro-4-[(4-methoxyphenyl)ethynyl]-3-[(3-methoxy-1H-pyrrol-2-yl)methylene]-2H-indol-2-one (G)

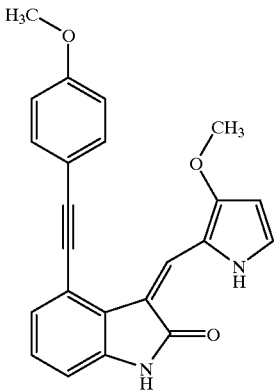

Step A: 4-Methoxyphenyl Acetylene

Using Method D above, 4-bromoanisole (Aldrich) was coupled with trimethylsilylacetylene (Aldrich) using $(Ph_3P)_2PdCl_2$ and CuI as catalyst in DMF and $Et_3N$ as solvent and was heated at reflux for 1 day. The resulting trimethylsilyl derivative was hydrolized with aqueous potassium hydroxide to give 4-methoxyphenyl acetylene.

Step B:

Using general Method D above, 4-methoxyphenyl acetylene (0.49 g, 3.68 mmol) (from Step A above) was coupled with (Z)-4-bromo-1,3-dihydro-3-[(3-methoxy-1H-pyrrol-2-yl)methylene]-2H-indol-2-one (Starting Material 1) (0.47 g, 1.47 mmol) using $DPPFPdCl_2$ (0.12 g) (Aldrich) and CuI (28 mg) (Aldrich) as catalyst in DMF (10 mL) and $Et_3N$ (15 mL) as solvent and was heated at reflux for 1 day, yielding (Z)-1,3-dihydro-4-[(4-methoxyphenyl)ethynyl]-3-[(3-methoxy-1H-pyrrol-2-yl)methylene]-2H-indol-2-one. (Yield 0.31 g, 57%).

Example 9

Synthesis of rac-(Z)-1,3-Dihydro-4-[3-hydroxy-3-(4-methoxyphenyl)-1-propynyl]-3-[(3-methoxy-1H-pyrrol-2-yl)methylene]-2H-indol-2-one (H)

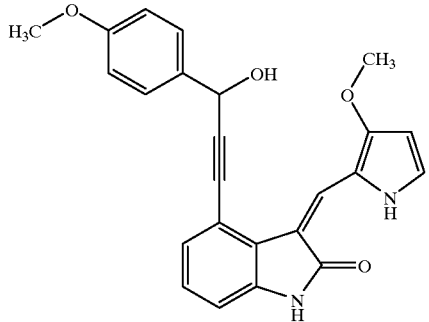

Using Method D above, 3-hydroxy-3-(4-methoxyphenyl)-1-propyne (115 mg, 0.70 mmol) (prepared by the addition of ethylmagnesium chloride (Aldrich) to 4-methoxybenzaldehyde (Aldrich) according to Method A above), was coupled with (Z)-4-bromo-1,3-dihydro-3-[(3-methoxy-1H-pyrrol-2-yl)methylene]-2H-indol-2-one (Starting Material 1) (174 mg, 0.55 mmol) using $(Ph_3P)_2PdCl_2$ (18 mg) (Aldrich) and CuI (10 mg) (Aldrich) as catalyst in DMF (2.5 mL) and $Et_3N$ (2.5 mL) as solvent at 70° C. for 15 h, yielding rac-(Z)-1,3-dihydro-4-[3-hydroxy-3-(4-methoxyphenyl)-1-propynyl]-3-[(3-methoxy-1H-pyrrol-2-yl)methylene]-2H-indol-2-one. (Yield 32 mg, 32%).

Example 10

Synthesis of rac-(Z)-1,3-Dihydro-4-[3-hydroxy-3-(3-hydroxyphenyl)-1-propynyl]-3-[(3-methoxy-1H-pyrrol-2-yl)methylene]-2H-indol-2-one (I)

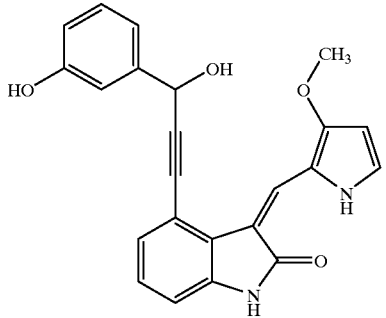

Using Method D above, 3-hydroxy-3-(3-hydroxyphenyl)-1-propyne (140 mg, 0.94 mmol) (prepared by the addition of ethynylmagnesium chloride (Aldrich) to 3-hydroxybenzaldehyde (Aldrich) through Method B above) was coupled to (Z)-4-bromo-1,3-dihydro-3-[(3-methoxy-1H-pyrrol-2-yl)methylene]-2H-indol-2-one (Starting Material 1) (200 mg, 0.63 mmol) using $(Ph_3P)_2PdCl_2$ (68 mg) (Aldrich) and CuI (32 mg) (Aldrich) as catalyst in DMF (4 mL) and $Et_3N$ (4 mL) as solvent at 80° C. for 15 h, yielding rac-(Z)-1,3-dihydro-4-[3-hydroxy-3-(3-hydroxyphenyl)-1-propynyl]-3-[(3-methoxy-1H-pyrrol-2-yl)methylene]-2H-indol-2-one. (Yield 82 mg, 31%).

Example 11

Synthesis of rac-(Z)-1,3-Dihydro-4-[3-hydroxy-3-(3-methoxyphenyl)-1-propynyl]-3-[(3-methoxy-1H-pyrrol-2-yl)methylene]-2H-indol-2-one (J)

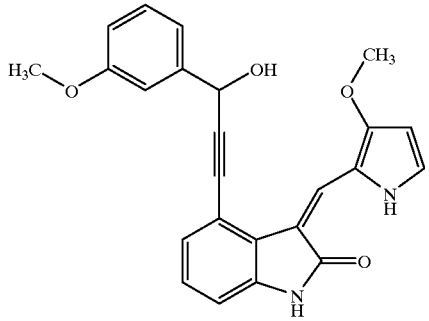

Using Method D above, 3-hydroxy-3-(3-methoxyphenyl)-1-propyne (151 mg, 1.0 mmol) (prepared by the addition of ethynylmagnesium chloride (Aldrich) to 3-methoxybenzaldehyde (Aldrich) according to Method A above) was coupled to (Z)-4-bromo-1,3-dihydro-3-[(3-methoxy-1H-pyrrol-2-yl)methylene]-2H-indol-2-one (Starting Material 1) (220 mg, 0.69 mmol) using $(Ph_3P)_2PdCl_2$ (100 mg) (Aldrich) and CuI (55 mg) (Aldrich) as catalyst in DMF (5 mL) and $Et_3N$ (5 mL) as solvent at 70° C. for 18 h, yielding rac-(Z)-1,3-dihydro-4-[3-hydroxy-3-(3-methoxyphenyl)-1-propynyl]-3-[(3-methoxy-1H-pyrrol-2-yl)methylene]-2H-indol-2-one. (Yield 66 mg, 24%).

Example 12

Synthesis of rac-(Z)-4-[3-[2,3-Dihydro-3-[(3-methoxy-1H-pyrrol-2-yl)methylene]-2-oxo-1H-indol-4-yl]-1-hydroxy-2-propynyl]benzoic Acid Methyl Ester (K)

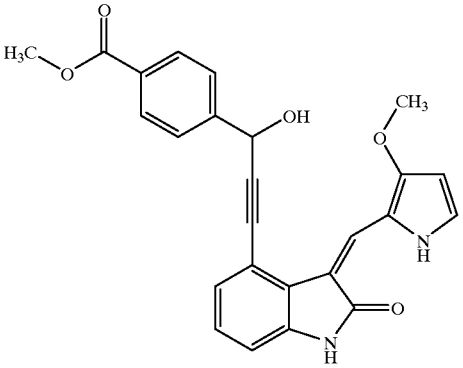

Using Method D above, 4-(1-hydroxy-2-propynyl)-benzoic acid methyl ester (137 mg, 0.72 mmol) (prepared by the addition of ethynylmagnesium chloride (Aldrich) to 4-carboxybenzaldehyde (Aldrich) using Method B above to give the acid which was converted to its methyl ester by Method E above), was coupled to (Z)-4-bromo-1,3-dihydro-3-[(3-methoxy-1H-pyrrol-2-yl)methylene]-2H-indol-2-one (Starting Material 1) (221 mg, 0.69 mmol) using $(Ph_3P)_2PdCl_2$ (37 mg) (Aldrich) and CuI (18 mg) (Aldrich) as catalyst in DMF (4 mL) and $Et_3N$ (4 mL) as solvent at 70° C. for 18 h, yielding rac-(Z)-4-[3-[2,3-dihydro-3-[(3-methoxy-1H-pyrrol-2-yl)methylene]-2-oxo-1H-indol-4-yl]-1-hydroxy-2-propynyl]benzoic acid methyl ester. (Yield 52 mg, 18%).

Example 13

Synthesis of rac-(Z)-4-[3-[2,3-Dihydro-3-[(3-methoxy-1H-pyrrol-2-yl)methylene]-2-oxo-1H-indol-4-yl]-1-hydroxy-2-propynyl]benzoic acid (L)

Using Method F above, 4-[1-hydroxy-3-[3-(3-methoxy-1H-pyrrol-2-ylmethylene)-2-oxo-2,3-dihydro-1H-indol-4-yl]-prop-2-ynyl]-benzoic acid methyl ester (30 mg, 0.07 mmol) (from Example 12 above) was hydrolyzed with $LiOH.H_2O$ (13 mg, 2.7 mmol) in THF (1 mL) and water (1 mL) at room temperature for 18 h, to yield rac-(Z)-4-[3-[2,3-dihydro-3-[(3-methoxy-1H-pyrrol-2-yl)methylene]-2-oxo-1H-indol-4-yl]-1-hydroxy-2-propynyl]benzoic acid. (Yield 21 mg, 72%).

Example 14

Synthesis of rac-(Z)-1,3-Dihydro-4-[3-hydroxy-3-(2-methoxyphenyl)-1-propynyl]-3-[(3-methoxy-1H-pyrrol-2-yl)methylene]-2H-indol-2-one (M)

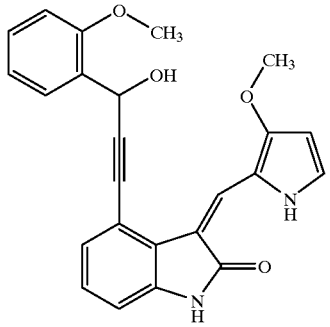

Using Method D above, 3-hydroxy-3-(2-methoxyphenyl)-1-propyne (150 mg, 0.92 mmol) (prepared by the addition of ethynylmagnesium chloride (Aldrich) to 2-methoxybenzaldehyde (Aldrich) according to Method A above), was coupled to (Z)-4-bromo-1,3-dihydro-3-[(3-methoxy-1H-pyrrol-2-yl)methylene]-2H-indol-2-one (Starting Material 1) (200 mg, 0.63 mmol) using (Ph$_3$P)$_2$PdCl$_2$ (70 mg) (Aldrich) and CuI (40 mg) (Aldrich) as catalyst in DMF (3 mL) and Et$_3$N (3 mL) as solvent at 70° C. for 18 h, yielding rac-(Z)-1,3-dihydro-4-[3-hydroxy-3-(2-methoxyphenyl)-1-propynyl]-3-[(3-methoxy-1H-pyrrol-2-yi)methylene]-2H-indol-2-one. (Yield 71 mg, 28%).

Example 15

Synthesis of rac-(Z)-4-[3-(1,3-benzodioxol-5-yl)-3-hydroxy-1-propynyl]-1,3-dihydro-3-[(3-methoxy-1H-pyrrol-2-yl)methylene]-2H-indol-2-one (N)

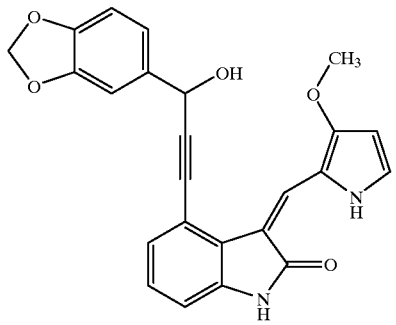

Using Method D above, 3-(1,3-benzodioxol-5-yl)-3-hydroxy-1-propyne (110 mg, 0.62 mmol) (prepared by the addition of ethynylmagnesium chloride (Aldrich) to piperonal (Aldrich) according to Method A above) was coupled to (Z)-4-bromo-1,3-dihydro-3-[(3-methoxy-1H-pyrrol-2-yl)methylene]-2H-indol-2-one (100 mg, 0.34 mmol) (Starting Material 1) using (Ph$_3$P)$_2$PdCl$_2$ (30 mg) (Aldrich) and CuI (16 mg) (Aldrich) as catalyst in DMF (3 mL) and Et$_3$N (3 mL) as solvent at 70° C. for 16 h, yielding rac-(Z)-4-[3-(1, 3-benzodioxol-5-yl)-3-hydroxy-1-propynyl]-1,3-dihydro-3-[(3-methoxy-1H-pyrrol-2-yl)methylene]-2H-indol-2-one. (Yield 46 mg, 33%).

Example 16

Synthesis of rac-(Z)-1,3-Dihydro-4-[3-hydroxy-3-(4-hydroxy-3-methoxyphenyl)-1-propynyl]-3-[(3-methoxy-1H-pyrrol-2-yl)methylene]-2H-indol-2-one (O)

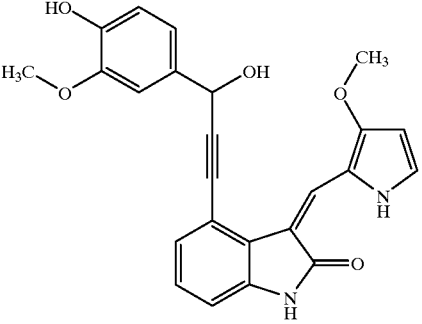

Using Method D above, 3-hydroxy-3-(4-hydroxy-3-methoxyphenyl)-1-propyne (197 mg, 1.1 mmol) (prepared by the addition of ethynylmagnesium chloride (Aldrich) to vanillin (Aldrich) according to Method B above) was coupled to (Z)-4-bromo-1,3-dihydro-3-[(3-methoxy-1H-pyrrol-2-yl)methylene]-2H-indol-2-one (Starting Material 1) (116 mg, 0.36 mmol) using (Ph$_3$P)$_2$PdCl$_2$ (33 mg) (Aldrich) and CuI (18 mg) (Aldrich) as catalyst in DMF (3 mL) and Et$_3$N (3 mL) as solvent at 70° C. for 16 h, yielding rac-(Z)-1,3-dihydro-4-[3-hydroxy-3-(4-hydroxy-3-methoxyphenyl)-1-propynyl]-3-[(3-methoxy-1H-pyrrol-2-yl)methylene]-2H-indol-2-one. (Yield 31 mg, 21%).

Example 17

Synthesis of 3-Hydroxy-3-(4-hydroxyphenyl)-1-propyne (P)

To a solution of trimethylsilylacetylene (1.00 g, 10 mmol) (Aldrich) in dry THF (100 mL) under argon at −78° C. was added n-butyllithium (4.4 mL, 11 mmol, 2.5 M solution in hexanes) (Aldrich) dropwise. The reaction was stirred for 30 min at −78° C., after which time 4-hydroxybenzaldehyde (0.50 g, 4 mmol) (Aldrich) was added and the reaction was allowed to slowly warm to room temperature. A saturated solution of ammonium chloride (5 mL) was then added and the reaction was stirred at room temperature for 2 h. The solution was then diluted by the addition of 30 mL water, and THF was removed in vacuo. The product was extracted with ethyl acetate (3×50 mL) and the combined organic layers were dried over magnesium sulfate and concentrated in vacuo to give clean 3-hydroxy-3-(4-hydroxyphenyl)-1-propyne which was used directly, without further purification. (Yield 501 mg, 84%).

Example 18

Synthesis of rac-(Z)-1,3-Dihydro-4-[3-hydroxy-3-(4-hydroxyphenyl)-1-propynyl]-3-[(3-methoxy-1H-pyrrol-2-yl)methylene]-2H-indol-2-one (Q)

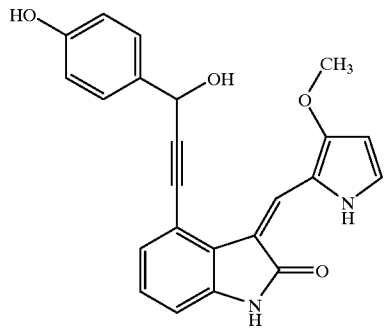

Using Method D above, 3-hydroxy-3-(4-hydroxyphenyl)-1-propyne (120 mg, 0.84 mmol) (from Example 17 above) was coupled to (Z)-4-bromo-1,3-dihydro-3-[(3-methoxy-1H-pyrrol-2-yl)methylene]-2H-indol-2-one (110 mg, 0.34 mmol) (Starting Material 1) using $(Ph_3P)_2PdCl_2$ (30 mg) (Aldrich) and CuI (15 mg) (Aldrich) as catalyst in DMF (3 mL) and $Et_3N$ (3 mL) as solvent at 70° C. for 16 h, yielding rac-(Z)-1,3-dihydro-4-[3-hydroxy-3-(4-hydroxyphenyl)-1-propynyl]-3-[(3-methoxy-1H-pyrrol-2-yl)methylene]-2H-indol-2-one. (Yield 62 mg, 47%).

Example 19

Synthesis of rac-(Z)-1,3-Dihydro-4-[3-(4-dimethylaminophenyl)-3-hydroxy-1-propynyl]-3-[(3-methoxy-1H-pyrrol-2-yl)methylene]-2H-indol-2-one (R)

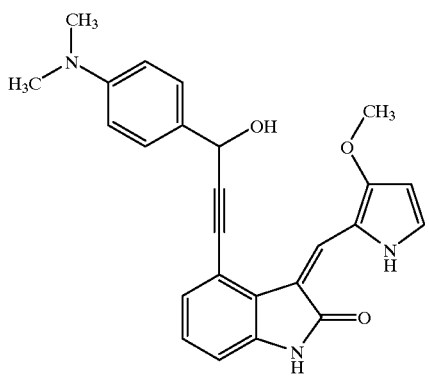

Using Method D above, 3-(4-dimethylaminophenyl)-3-hydroxy-1-propyne (160 mg, 0.91 mmol) (prepared by the addition of ethynylmagnesium chloride (Aldrich) to 4-dimethylaminobenzaldehyde (Aldrich) according to Method A above) was coupled to (Z)-4-bromo-1,3-dihydro-3-[(3-methoxy-1H-pyrrol-2-yl)methylene]-2H-indol-2-one (108 mg, 0.34 mmol) (Starting Material 1) using $(Ph_3P)_2PdCl_2$ (30 mg) (Aldrich) and CuI (16 mg) (Aldrich) as catalyst in DMF (3 mL) and $Et_3N$ (3 mL) as solvent at 70° C. for 19 h, yielding rac-(Z)-1,3-dihydro-4-[3-(4-dimethylaminophenyl)-3-hydroxy-1-propynyl]-3-[(3-methoxy-1H-pyrrol-2-yl)methylene]-2H-indol-2-one. (Yield 190 mg, 77%).

Example 20

Synthesis of rac-(Z)-1,3-Dihydro-4-[3-hydroxy-3-(4-phenoxyphenyl)-1-propynyl]-3-[(3-methoxy-1H-pyrrol-2-yl)methylene]-2H-indol-2-one (S)

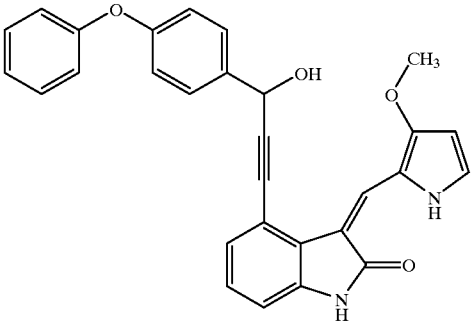

Using Method C above, 3-hydroxy-3-(4-phenoxyphenyl)-1-propyne (200 mg, 0.89 mmol) (prepared by the addition of ethynylmagnesium chloride (Aldrich) to 4-phenoxybenzaldehyde (Aldrich) according to Method A above) was coupled to (Z)-1,3-dihydro-4-iodo-3-[(3-methoxy-1H-pyrrol-2-yl)methylene]-2H-indol-2-one (Starting Material 2) (146 mg, 0.40 mmol) using $(Ph_3P)_2PdCl_2$ (30 mg) (Aldrich) and CuI (16 mg) (Aldrich) as catalyst in DMF (3 mL) and $Et_3N$ (3 mL) as solvent at 70° C. for 16 h, yielding rac-(Z)-1,3-dihydro-4-[3-hydroxy-3-(4-phenoxyphenyl)-1-propynyl]-3-[(3-methoxy-1H-pyrrol-2-yl)methylene]-2H-indol-2-one. (Yield 100 mg, 54%).

Example 21

Synthesis of rac-(Z)-1,3-Dihydro-4-[3-hydroxy-3-phenyl-1-butynyl]-3-[(3-methoxy-1H-pyrrol-2-yl)methylene]-2H-indol-2-one (T)

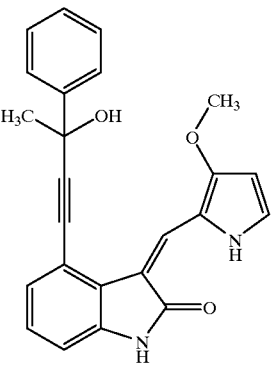

Using Method C above, 2-phenyl-3-butyn-2-ol (70 mg, 0.48 mmol) (Aldrich) was coupled to (Z)-1,3-dihydro-4-iodo-3-[(3-methoxy-1H-pyrrol-2-yl)methylene]- 2H-indol-2-one (146 mg, 0.4 mmol) (Starting Material 2) using $(Ph_3P)_2PdCl_2$ (20 mg) (Aldrich) and CuI (10 mg) (Aldrich) as catalyst in DMF (2 mL) and $Et_3N$ (2 mL) as solvent at 70° C. for 15 h, yielding rac-(Z)-1,3-dihydro-4-[3-hydroxy-3-phenyl-1-butynyl]-3-[(3-methoxy-1H-pyrrol-2-yl)methylene]-2H-indol-2-one. (Yield 85 mg, 55%).

Example 22

Synthesis of 3-[4-(3-Dimethylaminopropoxy)-phenyl]-3-hydroxy-1-propyne (U)

To a solution of 4-(3-dimethylaminopropoxy) benzaldehyde (0.83 g, 4 mmol) (Aldrich) in dry tetrahydrofuran (30 mL) under argon at room temperature was added ethynylmagnesium chloride (5 mmmol, 10 mL, 0.5M solution in tetrahydrofuran) (Aldrich) dropwise. The resulting solution was stirred for 1.5 h at which time 100 mL water was added, and the THF was removed in vacuo. The product was extracted with ethyl acetate (3×50 mL) and the combined organic layers were dried over magnesium sulfate and concentrated in vacuo to give clean 3-[4-(3-dimethylaminopropoxy)-phenyl]-3-hydroxy-1-propyne which was used directly, without further purification. (Yield 831 mg, 89%)

Example 23

Synthesis of rac-(Z)-1,3-Dihydro-4-[3-[4-(3-dimethylaminopropoxy)-phenyl]-3-hydroxy-1-propynyl]-3-[(3-methoxy-1H-pyrrol-2-yl)methylene]-2H-indol-2-one (V)

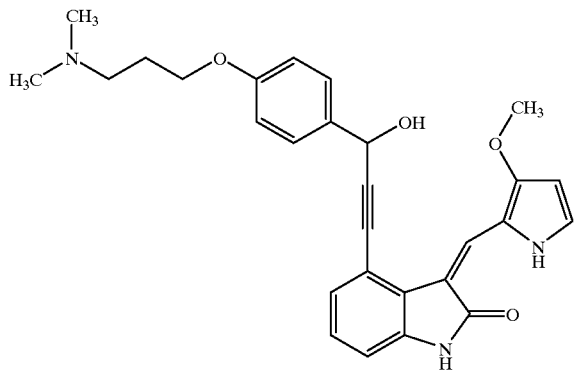

Using Method C above, 3-[4-(3-dimethylaminopropoxy)-phenyl]-3-hydroxy-1-propyne (201 mg, 0.86 mmol) (from Example 22 above) was coupled to (Z)-1,3-dihydro-4-iodo-3-[(3-methoxy-1H-pyrrol-2-yl)methylene]-2H-indol-2-one (Starting Material 2) (146 mg, 0.4 mmol) using (Ph$_3$P)$_2$PdCl$_2$ (34 mg) (Aldrich) and CuI (15 mg) (Aldrich) as catalyst in DMF (3 mL) and Et$_3$N (3 mL) as solvent at 70° C. for 16 h, to yield rac-(Z)-1,3-dihydro-4-[3-[4-(3-dimethylaminopropoxy)-phenyl]-3-hydroxy-1-propynyl]-3-[(3-methoxy-1H-pyrrol-2-yl)methylene]-2H-indol-2-one. (Yield 151 mg, 80%).

Example 24

Synthesis of 3-Hydroxy-3-(3-pyridinyl)-1-propyne (W)

3-Hydroxy-3-(3-pyridinyl)-1-propyne was prepared according to Method A above using 3-pyridine carboxaldehyde (0.428 g, 4 mmol) (Aldrich) in THF (20 mL) and ethynylmagnesium chloride (5 mmol, 10 mL, 0.5M solution in tetrahydrofuran) (Aldrich). (Yield 440 mg, 83%).

Example 25

Synthesis of rac-(Z)-1,3-Dihydro-4-[3-hydroxy-3-(3-pyridinyl)-1-propynyl]-3-[(3-methoxy-1H-pyrrol-2-yl)methylene]-2H-indol-2-one (X)

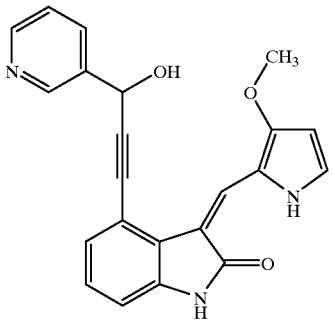

Using Method D above, 3-hydroxy-3-(3-pyridinyl)-1-propyne (150 mg, 1.13 mmol) (from Example 24 above) was coupled to (Z)-4-bromo-1,3-dihydro-3-[(3-methoxy-1H-pyrrol-2-yl)methylene]-2H-indol-2-one (135 mg, 0.42 mmol) (Starting Material 1) using (Ph$_3$P)$_2$PdCl$_2$ (32 mg) (Aldrich) and CuI (17 mg) (Aldrich) as catalyst in DMF (3 mL) and Et$_3$N (3 mL) as solvent at 70° C. for 17 h, to yield rac-(Z)-1,3-dihydro-4-[3-hydroxy-3-(3-pyridinyl)-1-propynyl]-3-[(3-methoxy-1H-pyrrol-2-yl)methylene]-2H-indol-2-one. (Yield 40 mg, 22%).

Example 26

Synthesis of (Z)-1,3-Dihydro-3-[(3-methoxy-1H-pyrrol-2-yl)methylene]-4-(3-phenoxy-1-propynyl)-2H-indol-2-one (Y)

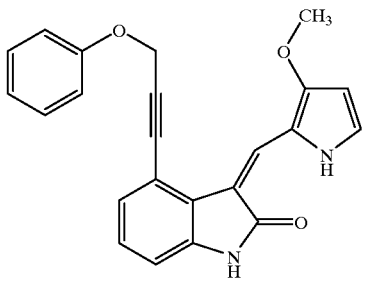

Using Method C above, phenyl propargyl ether (65 mg, 0.49 mmol) (Lancaster) was coupled to (Z)-1,3-dihydro-4-iodo-3-[(3-methoxy-1H-pyrrol-2-yl)methylene]-2H-indol-2-one (146 mg, 0.4 mmol) (Starting Material 2) using (Ph$_3$P)$_2$PdCl$_2$ (20 mg) (Aldrich) and CuI (10 mg) (Aldrich) as catalyst in DMF (2 mL) and Et$_3$N (2 mL) as solvent at 70° C. for 18 h, yielding (Z)-1,3-dihydro-3-[(3-methoxy-1H-pyrrol-2-yl)methylene]-4-(3-phenoxy-1-propynyl)-2H-indol-2-one. (Yield 92 mg, 62%).

Example 27

Synthesis of 3-Hydroxy-3-(1-methyl-pyrrol-2-yl)-1-propyne (Z)

3-Hydroxy-3-(1-methyl-pyrrol-2-yl)-1-propyne was prepared according to Method A above using 1-methyl-2-pyrrolecarboxaldehyde (0.450 g, 4 mmol) (Aldrich) in THF (20 mL) and ethynylmagnesium chloride (5 mmol, 10 mL, 0.5M solution in tetrahydrofuran) (Aldrich). (Yield 422 mg, 76%).

Example 28

Synthesis of rac-(Z)-1,3-Dihydro-4-[3-hydroxy-3-(1-methyl-pyrrol-2-yl)-1-propynyl]-3-[(3-methoxy-1H-pyrrol-2-yl)methylene]-2H-indol-2-one (AA)

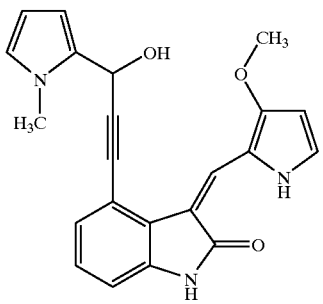

Using Method D above, 3-hydroxy-3-(1-methyl-pyrrol-2-yl)-1-propyne (132 mg, 0.98 mmol) (from Example 27 above) was coupled to (Z)-4-bromo-1,3-dihydro-3-[(3-methoxy-1H-pyrrol-2-yl)methylene]-2H-indol-2-one (112 mg, 0.35 mmol) (Starting Material 2) using $(Ph_3P)_2PdCl_2$ (31 mg)(Aldrich) and CuI (17 mg)(Aldrich) as catalyst in DMF (3 mL) and $Et_3N$ (3 mL) as solvent at 70° C. for 28 h, yielding rac-(Z)-1,3-dihydro-4-[3-hydroxy-3-(1-methyl-pyrrol-2-yl)-1-propynyl]-3-[(3-methoxy-1H-pyrrol-2-yl) methylene]-2H-indol-2-one. (Yield 114 mg, 87%).

Example 29: Synthesis of rac-(Z)-1,3-Dihydro-4-[3-hydroxy-3-(thiophen-3-yl)-1-propynyl]-3-[(3-methoxy-1H-pyrrol-2-yl)methylene]-2H-indol-2-one (BB)

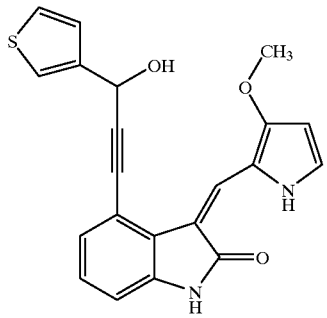

Using Method D above, 3-hydroxy-3-(thiophen-3-yl)-1-propyne (131 mg, 0.95 mmol) (prepared by the addition of ethynylmagnesium chloride (Aldrich) to 3-thiophenecarboxaldehyde (Aldrich) according to Method A above) was coupled to (Z)-4-bromo-1,3-dihydro-3-[(3-methoxy-1H-pyrrol-2-yl)methylene]-2H-indol-2-one (107 mg, 0.34 mmol) (Starting Material 1) using $(Ph_3P)_2PdCl_2$ (32 mg) (Aldrich) and CuI (17 mg) (Aldrich) as catalyst in DMF (3 mL) and $Et_3N$ (3 mL) as solvent at 70° C. or 18 h, yielding rac-(Z)-1,3-dihydro-4-[3-hydroxy-3-(thiophen-3-yl)-1-propynyl]-3-[(3-methoxy-1H-pyrrol-2-yl)methylene]-2H-indol-2-one. (Yield 93 mg, 72%).

Example 30

Synthesis of 3-Hydroxy-3-(1H-pyrrol-2-yl)-1-propyne (CC)

3-Hydroxy-3-(1H-pyrrol-2-yl)-1-propyne was prepared by Method B above using 2-pyrrolecarboxaldehyde (0.389 g, 4 mmol) (Aldrich) in THF (30 mL) and ethynylmagnesium chloride (20 mmol, 40 mL, 0.5M solution in tetrahydrofuran) (Aldrich). (Yield 345 mg, 82%).

Example 31

Synthesis of rac-(Z)-1,3-Dihydro-4-[3-hydroxy-3-(1H-pyrrol-2-yl)-1-propynyl]-3-[(3-methoxy-1H-pyrrol-2-yl)methylene]-2H-indol-2-one (DD)

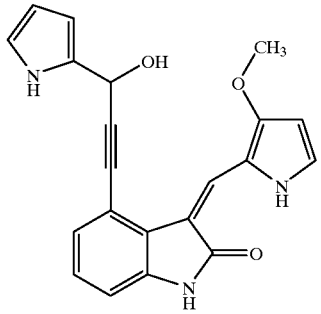

Using Method D above, 3-hydroxy-3-(1H-pyrrol-2-yl)-1-propyne (212 mg, 1.75 mmol) (from Example 30 above) was coupled to (Z)-4-bromo-1,3-dihydro-3-[(3-methoxy-1H-pyrrol-2-yl)methylene]-2H-indol-2-one (125 mg, 0.39 mmol) (Starting Material 1) using $(Ph_3P)_2PdCl_2$ (42 mg) (Aldrich) and CuI (20 mg) (Aldrich) as catalyst in DMF (4 mL) and $Et_3N$ (4 mL) as solvent at 70° C. for 18 h, yielding rac-(Z)-1,3-dihydro-4-[3-hydroxy-3-(1H-pyrrol-2-yl)-1-propynyl]-3-[(3-methoxy-1H-pyrrol-2-yl)methylene]-2H-indol-2-one. (Yield 68 mg, 49%).

Example 32

Synthesis of rac-(Z)-1,3-Dihydro-4-[3-(2,3-dimethoxyphenyl)-3-hydroxy-1-propynyl]-3-[(3-methoxy-1H-pyrrol-2-yl)methylene]-2H-indol-2-one (EE)

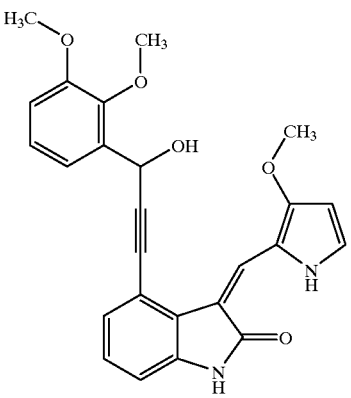

Using Method D above, 3-(2,3-dimethoxyphenyl)-3-hydroxy-1-propyne (132 mg, 0.69 mmol) (prepared by the addition of ethynylmagnesium chloride (Aldrich) to 2,3-dimethoxybenzaldehyde (Aldrich) according to Method A above) was coupled to (Z)-4-bromo-1,3-dihydro-3-[(3-methoxy-1H-pyrrol-2-yl)methylene]-2H-indol-2-one (Starting Material 1) (98 mg, 0.31 mmol) using $(Ph_3P)_2PdCl_2$ (38 mg) (Aldrich) and CuI (17 mg) (Aldrich) as catalyst in DMF (3 mL) and $Et_3N$ (3 mL) as solvent at 70°

C. for 17 h, yielding rac-(Z)-1,3-dihydro-4-[3-(2,3-dimethoxyphenyl)-3-hydroxy-1-propynyl]-3-[(3-methoxy-1H-pyrrol-2-yl)methylene]-2H-indol-2-one. (Yield 98 mg, 71%).

Example 33

Synthesis of rac-(Z)-1,3-Dihydro-4-[3-(3,4-dimethoxyphenyl)-3-hydroxy-1-propynyl]-3-[(3-methoxy-1H-pyrrol-2-yl)methylene]-2H-indol-2-one (FF)

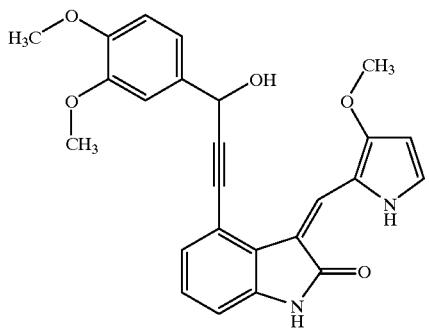

Using Method C above, 3-(3,4-dimethoxyphenyl)-3-hydroxy-1-propyne (150 mg, 0.78 mmol) (prepared by the addition of ethynylmagnesium chloride (Aldrich) to 3,4-dimethoxybenzaldehyde (Aldrich) according to Method A above) was coupled to (Z)-1,3-dihydro-4-iodo-3-[(3-methoxy-1H-pyrrol-2-yl)methylene]-2H-indol-2-one (Starting Material 2) (146 mg, 0.4 mmol) using $(Ph_3P)_2PdCl_2$ (40 mg) (Aldrich) and CuI (22 mg) (Aldrich) as catalyst in DMF (3 mL) and $Et_3N$ (3 mL) as solvent at 70° C. for 18 h, yielding rac-(Z)-1,3-dihydro-4-[3-(3,4-dimethoxyphenyl)-3-hydroxy-1-propynyl]-3-[(3-methoxy-1H-pyrrol-2-yl)methylene]-2H-indol-2-one. (Yield 121 mg, 70%).

Example 34

Synthesis of 3-Hydroxy-3-(3-hydroxy-4-methoxyphenyl)-1-propyne (GG)

3-Hydroxy-3-(3-hydroxy-4-methoxyphenyl)-1-propyne was prepared according to Method B above from 3-hydroxy-4-methoxybenzaldehyde (0.304 g, 2 mmol) (Aldrich) in THF (20 mL) and ethynylmagnesium chloride (5 mmol, 10 mL, 0.5M solution in tetrahydrofuran) (Aldrich). (Yield 273 mg, 77%).

Example 35

Synthesis of rac-(Z)-1,3-Dihydro-4-[3-hydroxy-3-(3-hydroxy-4-methoxyphenyl)-1-propynyl]-3-[(3-methoxy-1H-pyrrol-2-yl)methylene]-2H-indol-2-one (HH)

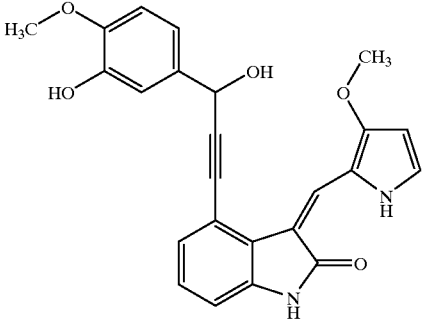

Using Method D above, 3-hydroxy-3-(3-hydroxy-4-methoxyphenyl)-1-propyne (105 mg, 0.59 mmol) (from Example 34 above) was coupled to (Z)-4-bromo-1,3-dihydro-3-[(3-methoxy-1H-pyrrol-2-yl)methylene]-2H-indol-2-one (122 mg, 0.38 mmol) (Starting Material 1) using $(Ph_3P)_2PdCl_2$ (34 mg) (Aldrich) and CuI (15 mg) (Aldrich) as catalyst in DMF (3 mL) and $Et_3N$ (3 mL) as solvent at 70° C. for 18 h, yielding rac-(Z)-1,3-dihydro-4-[3-hydroxy-3-(3-hydroxy-4-methoxyphenyl)-1-propynyl]-3-[(3-methoxy-1H-pyrrol-2-yl)methylene]-2H-indol-2-one. (Yield 101 mg, 64%).

Example 36

Synthesis of 3-Hydroxy-3-(2-pyridinyl)-1-propyne (II)

3-Hydroxy-3-(2-pyridinyl)-1-propyne was prepared according to Method A above from 2-pyridine carboxaldehyde (1.0 g, 9.3 mmol) (Aldrich) in THF (50 mL) and ethynylmagnesium chloride (10 mmol, 20 mL, 0.5M solution in tetrahydrofuran) (Aldrich). (Yield 956 mg, 77%).

Example 37

Synthesis of rac-(Z)-1,3-Dihydro-4-[3-hydroxy-3-(2-pyridinyl)-1-propynyl]-3-[(3-methoxy-1H-pyrrol-2-yl)methylene]-2H-indol-2-one (JJ)

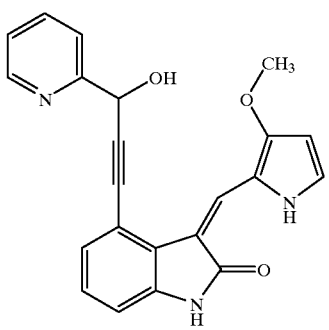

Using Method C above, 3-hydroxy-3-(2-pyridinyl)-1-propyne (133 mg, 1 mmol) (from Example 36 above) was coupled to (Z)-1,3-dihydro-4-iodo-3-[(3-methoxy-1H- pyrrol-2-yl)methylene]-2H-indol-2-one (147 mg, 0.4 mmol) using (Starting Material 2) (Ph₃P)₂PdCl₂ (40 mg) (Aldrich) and CuI (20 mg) (Aldrich) as catalyst in DMF (3 mL) and Et₃N (3 mL) as solvent at 70° C. for 19 h, yielding rac-(Z)-1,3-dihydro-4-[3-hydroxy-3-(2-pyridinyl)-1-propynyl]-3-[(3-methoxy-1H-pyrrol-2-yl)methylene]-2H-indol-2-one. (Yield 84 mg, 56%).

Example 38

Synthesis of rac-(Z)-1,3-Dihydro-4-[3-hydroxy-3-(2-thiophenyl)-1-propynyl]-3-[(3-methoxy-1H-pyrrol-2-yl)methylene]-2H-indol-2-one (KK)

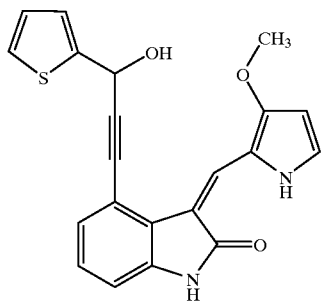

Using Method D above, 3-hydroxy-3-(2-thiophenyl)-1-propyne (102 mg, 0.74 mmol) (prepared by the addition of ethynylmagnesium chloride (Aldrich) to 2-thiophenecarboxaldehyde (Aldrich) according to Method A above) was coupled to (Z)-4-bromo-1,3-dihydro-3-[(3-methoxy-1H-pyrrol-2-yl)methylene]-2H-indol-2-one (126 mg, 0.39 mmol) (Starting Material 1) using (Ph₃P)₂PdCl₂ (35 mg) (Aldrich) and CuI (17 mg) (Aldrich) as catalyst in DMF (3 mL) and Et₃N (3 mL) as solvent at 70° C. for 18 h, yielding rac-(Z)-1,3-dihydro-4-[3-hydroxy-3-(2-thiophenyl)-1-propynyl]-3-[(3-methoxy-1H-pyrrol-2-yl)methylene]-2H-indol-2-one. (Yield 105 mg, 71%).

Example 39

Synthesis of 3-Hydroxy-3-[3-methoxy-4-[2-(4-morpholinyl)-ethoxy]-phenyl]-1-propyne (LL)

3-Hydroxy-3-[3-methoxy-4-[2-(4-morpholinyl)-ethoxy]-phenyl]-1-propyne was prepared according to Method A above from 3-methoxy-4-(2-morpholin-4-yl-ethoxy)-benzaldehyde (0.60 g, 2.26 mmol) (see below) in THF (25 mL) and ethynylmagnesium chloride (5 mmol, 10 mL, 0.5M solution in tetrahydrofuran) (Aldrich). (Yield 502 mg, 76%).

3-Methoxy-4-(2-morpholin-4-yl-ethoxy)-benzaldehyde was prepared from N-(2-hydroxyethyl)morpholine (Aldrich) and vanillin (Aldrich) by method H above.

Example 40

Synthesis of rac-(Z)-1,3-Dihydro-4-[3-hydroxy-3-[3-methoxy-4-[2-(4-morpholinyl)-ethoxy]-phenyl]-1-propynyl]-3-[(3-methoxy-1H-pyrrol-2-yl)methylene]-2H-indol-2-one (MM)

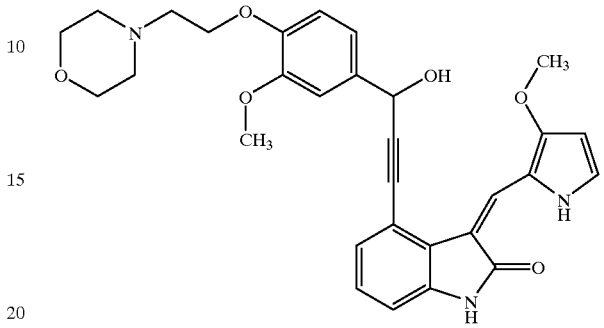

Using Method C above, 3-hydroxy-3-[3-methoxy-4-[2-(4-morpholinyl)-ethoxy]-phenyl]-1-propyne (610 mg, 2.09 mmol) (from Example 39 above) was coupled to (Z)-1,3-dihydro-4-iodo-3-[(3-methoxy-1H-pyrrol-2-yl)methylene]-2H-indol-2-one (200 mg, 0.55 mmol) (Starting Material 2) using (Ph₃P)₂PdCl₂ (50 mg) (Aldrich) and CuI (25 mg) (Aldrich) as catalyst in DMF (3 mL) and Et₃N (3 mL) as solvent at 70° C. for 22 h, yielding rac-(Z)-1,3-dihydro-4-[3-hydroxy-3-[3-methoxy-4-[2-(4-morpholinyl)-ethoxy]-phenyl]-1-propynyl]-3-[(3-methoxy-1H-pyrrol-2-yl)methylene]-2H-indol-2-one. (Yield 154 mg, 53%).

Example 41

Synthesis of rac-(Z)-1,3-Dihydro-4-[3-hydroxy-3-[3-methoxy-4-[2-(4-morpholinyl)-ethoxy]-phenyl]-1-propynyl]-3-[(3-methoxy-1H-pyrrol-2-yl)methylene]-2H-indol-2-one hydrochloride salt (NN)

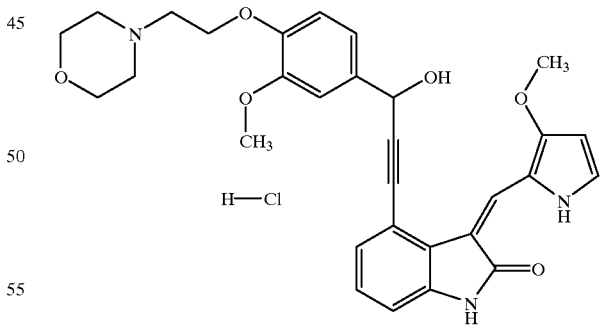

The hydrochloride salt of rac-(Z)-1,3-dihydro-4-[3-hydroxy-3-[3-methoxy-4-[2-(4-morpholinyl)-ethoxy]-phenyl]-1-propynyl]-3-[(3-methoxy-1H-pyrrol- 2-yl)methylene]-2H-indol-2-one (Compound MM from Example 40) was prepared by dissolving Compound MM in ethyl acetate and bubbling hydrogen chloride gas through the solution. The resulting red precipitate was then filtered off and dried.

Example 42

Synthesis of rac-(Z)-1,3-Dihydro-4-[3-hydroxy-3-(3-methoxy-2-thiophenyl)-1-propynyl]-3-[(3-methoxy-1H-pyrrol-2-yl)methylene]-2H-indol-2-one (OO)

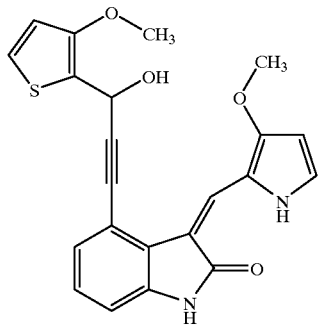

Step A: 3-Hydroxy-3-(3-methoxy-2-thiophenyl)-1-propyne.

3-Methoxy-2-thiophenecarboxadlehyde was prepared by adding n-butyllithium (10.56 mmol, 2.5M solution in hexane)(Aldrich), without cooling, to a solution of 3-methoxythiophene (1 g,8.8 mmol) (Aldrich) in dry diethyl ether (5 mL) over a period of 5 min. The mixture was gently heated at reflux for 2 h at which time the organolithium compound was transferred, via cannula, to a solution of DMF (23 mmol) in diethyl ether (5 mL) which was cooled in an ice bath. The reaction was stirred at room temperature for 14 h, at which time 1N HCl (10 mL) was added and the layers were separated. The aqueous layer was extracted with diethyl ether (3×25 mL), and the combined organic extracts were dried over magnesium sulfate, and concentrated to yield 3-methoxy-2-thiophenecarboxaldehyde as a pale, yellow solid. The 3-methoxy-2-thiophenecarboxaldehyde was then added to ethynylmagnesium chloride (Aldrich) according to Method A above to yield 3-hydroxy-3-(3-methoxy-2-thiophenyl)-1-propyne. (Yield 151 mg, 0.9 mmol).

Step B: Using Method C above, 3-hydroxy-3-(3-methoxy-2-thiophenyl)-1-propyne (from Step A above) was coupled to (Z)-1,3-dihydro-4-iodo-3-[(3-methoxy-1H-pyrrol-2-yl)methylene]-2H-indol-2-one (150 mg, 0.41 mmol) (Starting Material 2) using $(Ph_3P)_2PdCl_2$ (20 mg) (Aldrich) and CuI (10 mg) (Aldrich) as catalyst in DMF (2 mL) and $Et_3N$ (2 mL) as solvent at 70° C. for 20 h, yielding rac-(Z)-1,3-dihydro-4-[3-hydroxy-3-(3-methoxy-2-thiophenyl)-1-propynyl]-3-[(3-methoxy-1H-pyrrol-2-yl)methylene]-2H-indol-2-one. (Yield 98 mg, 59%: mp=213–216° C.).

Example 43

Synthesis of 3-Hydroxy-3-(2,4,5-trimethoxyphenyl)-1-propyne

3-Hydroxy-3-(2,4,5-trimethoxyphenyl)-1-propyne was prepared according to Method A above from 2,4,5-trimethoxybenzaldehyde (0.784 g, 4 mmol) (Aldrich) in THF (20 mL) and ethynylmagnesium chloride (5 mmol, 10 mL, 0.5M solution in tetrahydrofuran) (Aldrich). (Yield 548 mg, 71%).

Example 44

Synthesis of rac-(Z)-1,3-Dihydro-4-[3-hydroxy-3-(2,4,5-trimethoxyphenyl)-1-propynyl]-3-[(3-methoxy-1H-pyrrol-2-yl)methylene]-2H-indol-2-one (PP)

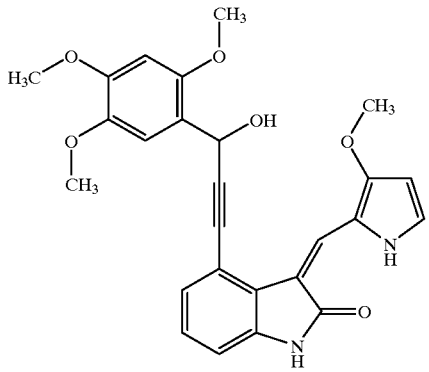

Using Method C above, 3-hydroxy-3-(2,4,5-trimethoxyphenyl)-1-propyne (150 mg, 0.67 mmol) (from Example 43 above) was coupled to (Z)-1,3-dihydro-4-iodo-3-[(3-methoxy-1H-pyrrol-2-yl)methylene]-2H-indol-2-one (150 mg, 0.41 mmol) (Starting Material 2) using $(Ph_3P)_2PdCl_2$ (35 mg) (Aldrich) and CuI (16 mg) (Aldrich) as catalyst in DMF (3 mL) and $Et_3N$ (3 mL) as solvent at 70° C. for 16 h, yielding rac-(Z)-1,3-dihydro-4-[3-hydroxy-3-(2,4,5-trimethoxyphenyl)-1-propynyl]-3-[(3-methoxy-1H-pyrrol-2-yl)methylene]-2H-indol-2-one. (Yield 101 mg, 53%).

Example 45

Synthesis of (4-Formyl-2-methoxy-phenoxy)-acetic acid methyl ester (4-Formyl-2-methoxy-phenoxy)-acetic acid methyl ester was prepared by dissolving vanillin (4.1 mmol) (Aldrich) in dry THF (10 mL) and dry DMF (1 mL). Sodium hydride (109 mg, 4.5 mmol) was then added to the solution slowly and the resulting mixture was stirred at room temperature for 1 h at which time methyl bromoacetate (5 mmol) (Aldrich) was added dropwise. The reaction was stirred at room temperature for 14 h at which time water (10 mL) was added and the THF was evaporated in vacuo. The aqueous layer was then extracted with ethyl acetate (3×15 mL), and the combined organic layers were dried over magnesium sulfate and concentrated. The resulting (4-formyl-2-methoxy-phenoxy)-acetic acid methyl ester was purified via flash column chromatography ($SiO_2$, 230–400 mesh) with ethyl acetate/hexane.

Example 46

Synthesis of [4-(1-Hydroxy-2-propynyl)-2-methoxy-phenoxy]-acetic acid methyl ester

[4-(1-Hydroxy-2-propynyl)-2-methoxy-phenoxy]-acetic acid methyl ester was prepared according to Method A above (except the Grignard reagent was added at −78° C.) from (4-formyl-2-methoxy-phenoxy)-acetic acid methyl ester (0.645 g, 2.9 mmol) (from Example 45) in THF (30 mL) and ethynylmagnesium chloride (3.45 mmol, 7 mL, 0.5M solution in tetrahydrofuran) (Aldrich). (Yield 525 mg, 72%).

Example 47

Synthesis of rac-(Z)-[4-[3-[2,3-Dihydro-3-[(3-methoxy-1H-pyrrol-2-yl)methylene]-2-oxo-1H-indol-4-yl]-1-hydroxy-2-propynyl]-2-methoxyphenoxy]acetic Acid Methyl Ester (QQ)

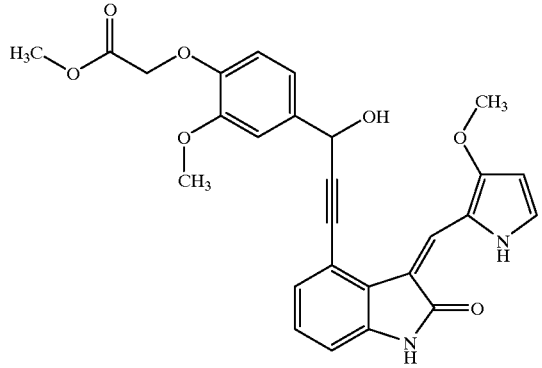

Using Method C above, [4-(1-hydroxy-2-propynyl)-2-methoxy-phenoxy]-acetic acid methyl ester (158 mg, 0.63 mmol) (from Example 46) was coupled to (Z)-1,3-dihydro-4-iodo-3-[(3-methoxy-1H-pyrrol-2-yl)methylene]-2H-indol-2-one (150 mg, 0.41 mmol) (Starting Material 2) using $(Ph_3P)_2PdCl_2$ (20 mg) (Aldrich) and CuI (10 mg) (Aldrich) as catalyst in DMF (2 mL) and $Et_3N$ (2 mL) as solvent at 70° C. for 16 h, yielding rac-(Z)-[4-[3-[2,3-dihydro-3-[(3-methoxy-1H-pyrrol-2-yl)methylene]-2-oxo-1H-indol-4-yl]-1-hydroxy-2-propynyl]-2-methoxyphenoxy]acetic acid methyl ester. (Yield 91 mg, 46%).

Example 48

Synthesis of rac-(Z)-[4-[3-[2,3-Dihydro-3-[(3-methoxy-1H-pyrrol-2-yl)methylene]-2-oxo-1H-indol-4-yl]-1-hydroxy-2-propynyl]-2-methoxyphenoxy]acetic Acid (RR)

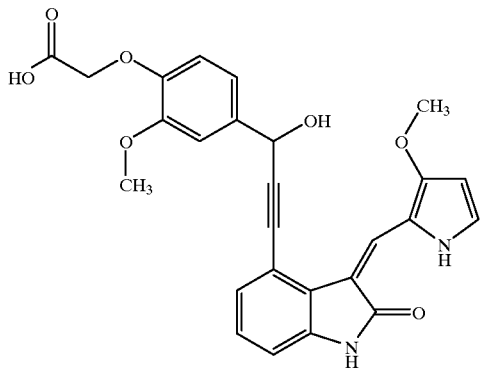

rac-(Z)-[4-[3-[2,3-Dihydro-3-[(3-methoxy-1H-pyrrol-2-yl)methylene]-2-oxo-1H-indol-4-yl]-1-hydroxy-2-propynyl]-2-methoxyphenoxy]acetic acid methyl ester(28 mg, 0.057 mmol) (from Example 47) was hydrolyzed with $LiOH.H_2O$ (55 mg, 1.15 mmol) in THF (0.5 mL) and $H_2O$ (0.5 mL) at room temperature for 20 h according to Method F above to yield rac-(Z)-[4-[3-[2,3-dihydro-3-[(3-methoxy-1H-pyrrol-2-yl)methylene]-2-oxo-1H-indol-4-yl]-1-hydroxy-2-propynyl]-2-methoxyphenoxy]acetic acid. (Yield 22 mg, 81%).

Example 49

Synthesis of 3-Hydroxy-3-(4-methoxy-1,3-benzodioxol-6-yl)-1-propyne

3-Hydroxy-3-(4-methoxy-1,3-benzodioxol-6-yl)-1-propyne was prepared according to Method A above from 3-methoxy-4,5-methylenedioxybenzaldehyde (0.721 g, 4 mmol) (Lancaster) in THF (20 mL) and ethynylmagnesium chloride (5 mmol, 10 mL, 0.5M solution in tetrahydrofuran) (Aldrich). (Yield 629 mg, 76%).

Example 50

Synthesis of rac-(Z)-4-[3-hydroxy-3-(4-methoxy-1,3-benzodioxol-6-yl)-1-propynyl]-1,3-dihydro-3-[(3-methoxy-1H-pyrrol-2-yl)methylene]-2H-indol-2-one (SS)

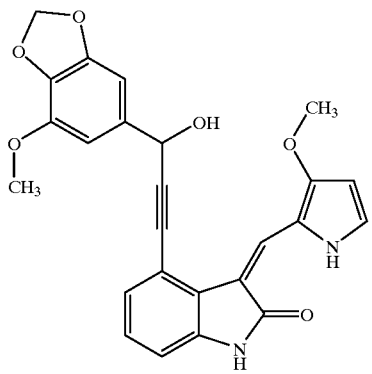

Using Method C above, 3-hydroxy-3-(4-methoxy-1,3-benzodioxol-6-yl)-1-propyne (153 mg, 0.74 mmol) (from Example 49 above) was coupled to (Z)-1,3-dihydro-4-iodo-3-[(3-methoxy-1H-pyrrol-2-yl)methylene]-2H-indol-2-one (147 mg, 0.4 mmol) (Starting Material 2) using $(Ph_3P)_2PdCl_2$ (40 mg) (Aldrich) and CuI (20 mg) (Aldrich) as catalyst in DMF (3 mL) and $Et_3N$ (3 mL) as solvent at 70° C. for 16 h, yielding rac-(Z)-4-[3-hydroxy-3-(4-methoxy-1,3-benzodioxol-6-yl)-1-propynyl]-1,3-dihydro-3-[(3-methoxy-1H-pyrrol-2-yl)methylene]-2H-indol-2-one. (Yield 98 mg, 55%).

Example 51

Synthesis of 3-Hydroxy-3-[4-[2-(4-morpholinyl)-ethoxy]-phenyl]-1-propyne

3-Hydroxy-3-[4-[2-(4-morpholinyl)-ethoxy]-phenyl]-1-propyne was prepared according to Method A above from 4-[2-(4-morpholinyl)-ethoxy]-benzaldehyde (0.630 g, 2.68 mmol) (see below) in THF (20 mL) and ethynylmagnesium chloride (3.0 mmol, 6 mL, 0.5M solution in tetrahydrofuran) (Aldrich). (Yield 492 mg, 70%).

4-[2-(4-Morpholinyl)-ethoxy]-benzaldehyde was prepared from N-(2-hydroxyethyl)morpholine (Aldrich) and vanillin (Aldrich) by method H above.

Example 52

Synthesis of rac-(Z)-1,3-Dihydro-4-[3-hydroxy-3-[4-[2-(4-morpholinyl)-ethoxy]-phenyl]-1-propynyl]-3-[(3-methoxy-1H-pyrrol-2-yl)methylene]-2H-indol-2-one (TT)

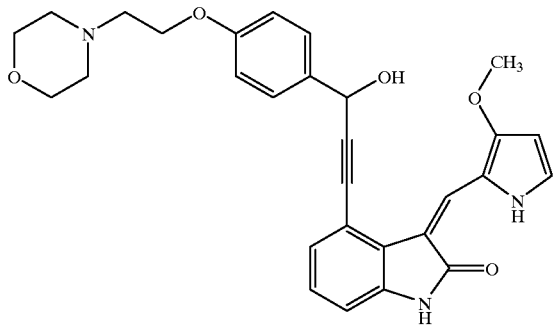

Using Method C above, 3-hydroxy-3-[4-[2-(4-morpholinyl)-ethoxy]-phenyl]-1-propyne (220 mg, 0.84 mmol) (from Example 51) was coupled to (Z)-1,3-dihydro-4-iodo-3-[(3-methoxy-1H-pyrrol-2-yl)methylene]-2H-indol-2-one (147 mg, 0.4 mmol) (Starting Material 2) using $(Ph_3P)_2PdCl_2$ (38 mg) (Aldrich) and CuI (17 mg) (Aldrich) as catalyst in DMF (3 mL) and $Et_3N$ (3 mL) as solvent at 70° C. for 20 h, yielding rac-(Z)-1,3-dihydro-4-[3-hydroxy-3-[4-[2-(4-morpholinyl)-ethoxy]-phenyl]-1-propynyl]-3-[(3-methoxy-1H-pyrrol-2-yl)methylene]-2H-indol-2-one. (Yield 164 mg, 82%).

Example 53

Synthesis of 3-(4-Chloro-2-methylsulfanylmethoxy-phenyl)-3-hydroxy-1-propyne

Step A:

4-Chlorosalicylic acid (34.51 g, 0.2 mol) (Aldrich) was suspended in a solution of methanol (100 mL) and concentrated sulfuric acid (8 mL). The mixture was heated at reflux for 17 h. After cooling to room temperature, the mixture was concentrated under reduced pressure. The resulting residue was dissolved in ether (400 mL) and washed successively with water (400 mL), saturated aqueous sodium bicarbonate (400 mL), and saturated aqueous sodium chloride (400 mL). The ether solution was then dried ($MgSO_4$), filtered, and concentrated. The resulting yellow oil was distilled to give methyl 4-chlorosalicylate. (Yield 32.89 g, 88%; b.p. 86–90° C., 0.15 mm Hg).

Step B:

Sodium hydride (11.80 g, 50% in oil) was washed with petroleum ether twice to remove oil. Hexamethylphosphorimide (HMPA) (100 mL) (Aldrich) was added to this washed sodium hydride under an argon atmosphere. The resulting mixture was stirred magnetically and cooled in an ice/water bath. Methyl 4-chlorosalicylate (37.32 g) (from Step A above) in HMPA (50 mL) was added dropwise and the mixture stirred for an additional 10 min. A solution of chloromethyl methyl sulfide (20 mL) (Aldrich) in HMPA (100 mL) was added and stirring at room temperature was continued for 24 h. The reaction mixture was then partitioned between toluene (3×1 L) and water (3×1 L). The toluene layers were combined, dried ($MgSO_4$), and concentrated under reduced pressure. The resulting oil was recrystallized from dichloromethane—hexane mixture to give the desired methyl thiomethyl ether. (Yield 33.92 g, 68.75%; mp 64–65.5° C.).

Step C:

A solution of the methyl thiomethyl ether (10.0 g, 40.5 mmol) from Step B above in THF (50 mL) was added dropwise to a suspension of lithium aluminum hydride (LAH) (Aldrich) in THF (50 mL) under argon with magnetic stirring over 30 min. The suspension was then heated at reflux for 3 h. After cooling, the mixture was poured into 2N aqueous HCl (200 mL) and extracted with ether (2×200 mL). The ether layers were washed with saturated aqueous sodium chloride solution (200 mL), then combined, dried ($MgSO_4$) and concentrated. Residue was filtered through silica gel (100 g) and product eluted with dichloromethane (Fisher Scientific). The product was further purified by vacuum distillation to give the benzyl alcohol product as a colorless oil. (Yield 7.24 g, 82%), bp 156–160° C., 0.07 mm Hg).

Step D:

The benzyl alcohol (5.66 g, 25.9 mmol) oil of Step C above, in dichloromethane (70 mL), was mixed with pyridinium dichromate (20 g) (Aldrich) and stirred at 4° C. for 20 h. The mixture was then diluted with dichloromethane (35 mL) and hexane (35 mL) and filtered through silica gel (50 g) and eluted with dichloromethane. The first 500 mL of eluate were concentrated under reduced pressure and the residue recrystallized from hexane to give 4-chloro-2-methylsulfanylmethoxybenzaldehyde as white needles. (Yield 4.99 g, 89%; mp 67–68° C.).

Step E:

The desired 3-(4-Chloro-2-methylsulfanylmethoxy-phenyl)-3-hydroxy-1-propyne was then prepared according to Method A above from the 4-chloro-2-methylsulfanylmethoxybenzaldehyde (0.870 g, 4 mmol) (from step D above) in THF (20 mL) and ethynylmagnesium chloride (5 mmol, 10 mL, 0.5M solution in tetrahydrofuran) (Aldrich). (Yield 802 mg, 83%).

Example 54

Synthesis of rac-(Z)-4-[3-(4-Chloro-2-methylsulfanylmethoxy-phenyl)-3-hydroxy-1-propynyl]-1,3-dihydro-3-[(3-methoxy-1H-pyrrol-2-yl)methylene]-2H-indol-2-one (UU)

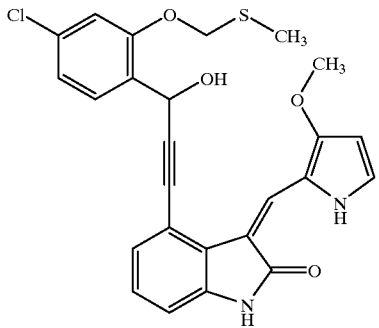

Using Method D above, 3-(4-chloro-2-methylsulfanylmethoxy-phenyl)-3-hydroxy-1-propyne (158 mg, 0.65 mmol) (from Example 53 above) was coupled to (Z)-4-bromo-1,3-dihydro-3-[(3-methoxy-1H-pyrrol-2-yl)methylene]-2H-indol-2-one (152 mg, 0.48 mmol) (Starting Material 1) using $(Ph_3P)_2PdCl_2$ (40 mg) (Aldrich) and CuI (22 mg) (Aldrich) as catalyst in DMF (3 mL) and $Et_3N$ (3 mL) as solvent at 70° C. for 17 h, yielding rac-(Z)-4-[3-(4-chloro-2-methylsulfanylmethoxy-phenyl)-3-hydroxy-1-propynyl]-1,3-dihydro-3-[(3-methoxy-1H-pyrrol-2-yl)methylene]-2H-indol-2-one. (Yield 132 mg, 57%).

Example 55

Synthesis of rac-(Z)-1,3-Dihydro-4-[3-(2-furanyl)-3-hydroxy-1-propynyl]-3-[(3-methoxy-1H-pyrrol-2-yl)methylene]-2H-indol-2-one (VV)

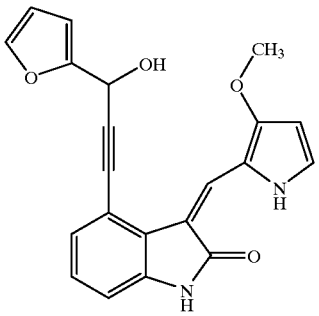

Using Method C above, 3-(2-furanyl)-3-hydroxy-1-propyne (148 mg, 1.24 mmol) (prepared by the addition of ethynylmagnesium chloride (Aldrich) to 2-furfural (Aldrich) according to Method A above) was coupled to (Z)-1,3-dihydro-4-iodo- 3-[(3-methoxy-1H-pyrrol-2-yl)methylene]-2H-indol-2-one (152 mg, 0.42 mmol) (Starting Material 2) using $(Ph_3P)_2PdCl_2$ (34 mg) and CuI (16 mg) as catalyst in DMF (3 mL) and $Et_3N$ (3 mL) as solvent at 70° C. for 20 h, to yield rac-(Z)-1,3-dihydro-4-[3-(2-furanyl)-3-hydroxy-1-propynyl]-3-[(3-methoxy-1H-pyrrol-2-yl)methylene]-2H-indol-2-one. (Yield 88 mg, 58%).

Example 56

Synthesis of rac-(Z)-4-[3-(3-Chlorophenyl)-3-hydroxy-1-propynyl]-1,3-dihydro-3-[(3-methoxy-1H-pyrrol-2-yl)methylene]-2H-indol-2-one (WW)

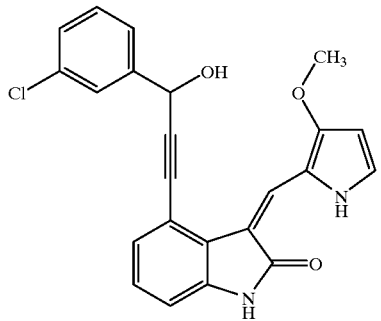

Using Method C above, 3-(3-chlorophenyl)-3-hydroxy-1-propyne (150 mg, 0.9 mmol) (prepared by the addition of ethynylmagnesium chloride to 3-chlorobenzaldehyde according to Method A above) was coupled to (Z)-1,3-dihydro-4-iodo-3-[(3-methoxy-1H-pyrrol-2-yl)methylene]-2H-indol-2-one (148 mg, 0.4 mmol) (Starting Material 2) using $(Ph_3P)_2PdCl_2$ (35 mg) and CuI (16 mg) as catalyst in DMF (3 mL) and $Et_3N$ (3 mL) as solvent at 70° C. for 17 h, yielding rac-(Z)-4-[3-(3-chlorophenyl)-3-hydroxy-1-propynyl]-1,3-dihydro-3-[(3-methoxy-1H-pyrrol-2-yl)methylene]-2H-indol-2-one. (Yield 132 mg, 81%).

Example 57

Synthesis of [4-(1-Hydroxy-2-propynyl)-phenoxy]-acetic Acid 1,1-dimethyl ethyl ester Step A:

Sodium hydride (109 mg, 4.5 mmol) was added slowly to a solution of 4-hydroxybenzaldehyde (4.1 mmol) (Aldrich) in dry THF (10 mL) and dry DMF (1 mL), and the resulting mixture was stirred at room temperature for 1 h at which time 1,1-dimethylethyl bromoacetate (5 mmol) (Aldrich) was added dropwise. The reaction was stirred at room temperature for 14 h. Water (10 mL) was then added and the THF was evaporated in vacuo. The aqueous layer was extracted with ethyl acetate (3×15 mL), and the combined organic layers were dried over magnesium sulfate and concentrated. The resulting product, (4-formyl-phenoxy)-acetic acid 1,1-dimethyl ethyl ester, was purified via flash column chromatography ($SiO_2$, 230–400 mesh) with ethyl acetate/hexane.

Step B:

[4-(1-Hydroxy-2-propynyl)-phenoxy]-acetic acid 1,1-dimethyl ethyl ester was then prepared according to Method A above (except the Grignard reagent was added at 0° C.) from (4-formyl-phenoxy)-acetic acid 1,1-dimethyl ethyl ester (1.0 g, 4.2 mmol) (from Step A above) in THF (20 mL) and ethynylmagnesium chloride (5.1 mmol, 10.2 mL, 0.5M solution in tetrahydrofuran) (Aldrich). (Yield 817 mg, 74%).

Example 58

Synthesis of rac-(Z)-[4-[3-[2,3-dihydro-3-[(3-methoxy-1H-pyrrol-2-yl)methylene]-2-oxo-1H-indol-4-yl]-1-hydroxy-2-propynyl]phenoxy]acetic Acid 1,1-dimethylethyl ester (XX)

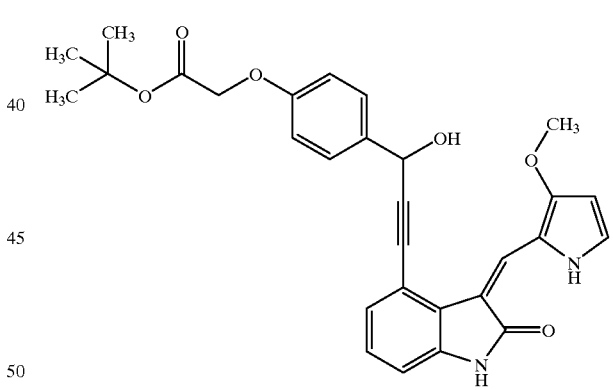

Using Method C above, [4-(1-hydroxy-2-propynyl)-phenoxy]-acetic acid 1,1-dimethyl ehtyl ester (129 mg, 0.49 mmol) (from Example 57 above) was coupled to (Z)-1,3-dihydro-4-iodo-3-[(3-methoxy-1H-pyrrol-2-yl)methylene]-2H-indol-2-one (150 mg, 0.41 mmol) (Starting Material 2) using $(Ph_3P)_2PdCl_2$ (20 mg) (Aldrich) and CuI (10 mg) (Aldrich) as catalyst in DMF (2 mL) and $Et_3N$ (2 mL) as solvent at 70° C. for 20 h, yielding rac-(Z)-[4-[3-[2,3-dihydro-3-[(3-methoxy-1H-pyrrol-2-yl)methylene]-2-oxo-1H-indol-4-yl]-1-hydroxy-2-propynyl]phenoxy]acetic acid 1,1-dimethylethyl ester. (Yield 106 mg, 52%: m.p. 173–175° C.).

Example 59

Synthesis of rac-(Z)-[4-[3-[2,3-dihydro-3-[(3-methoxy-1H-pyrrol-2-yl)methylene]-2-oxo-1H-indol-4-yl]-1-hydroxy-2-propynyl]phenoxy]acetic Acid (YY)

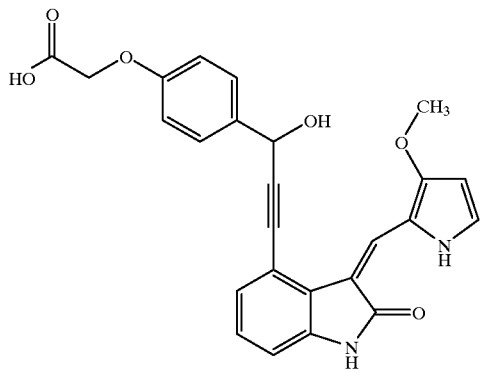

Using Method F above, rac-(Z)-[4-[3-[2,3-dihydro-3-[(3-methoxy-1H-pyrrol-2-yl)methylene]-2-oxo-1H-indol-4-yl]-1-hydroxy-2-propynyl]phenoxy]acetic acid 1,1-dimethylethyl ester (from Example 58 above) (30 mg, 0.061 mmol) was hydrolyzed with LiOH.H$_2$O (58 mg, 1.22 mmol) in THF (0.5 mL) and H$_2$O (0.5 mL) for 12 h, yielding rac-(Z)-[4-[3-[2,3-dihydro-3-[(3-methoxy-1H-pyrrol-2-yl)methylene]-2-oxo-1H-indol-4-yl]-1-hydroxy-2-propynyl]phenoxy]acetic acid. (Yield 24 mg, 89%).

Example 60

Synthesis of rac-(Z)-1,3-Dihydro-4-[3-hydroxy-3-(3-nitrophenyl)-1-propynyl]-3-[(3-methoxy-1H-pyrrol-2-yl)methylene]-2H-indol-2-one (ZZ)

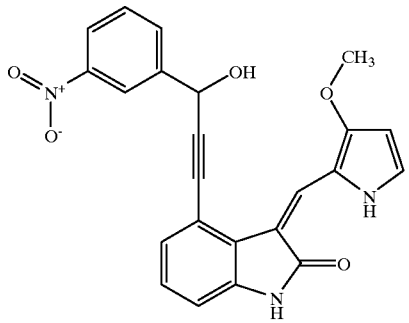

Using Method C above, 1-(3-nitro-phenyl)-2-propyn-1-ol (126 mg, 0.71 mmol) (prepared by the addition of ethynylmagnesium chloride (Aldrich) to 3-nitrobenzaldehyde (Aldrich) according to Method A above) was coupled to (Z)-1,3-dihydro-4-iodo-3-[(3-methoxy-1H-pyrrol-2-yl)methylene]-2H-indol-2-one (134 mg, 0.37 mmol) (Starting Material 2) using (Ph$_3$P)$_2$PdCl$_2$ (35 mg) (Aldrich) and CuI (20 mg) (Aldrich) as catalyst in DMF (3 mL) and Et$_3$N (3 mL) as solvent at 70° C. for 20 h, yielding rac-(Z)-1,3-dihydro-4-[3-hydroxy-3-(3-nitrophenyl)-1-propynyl]-3-[(3-methoxy-1H-pyrrol-2-yl)methylene]-2H-indol-2-one. (Yield 84 mg, 52%).

Example 61

Synthesis of rac-(Z)-4-[3-(3-Aminophenyl)-3-hydroxy-1-propynyl]-1,3-dihydro-3-[(3-methoxy-1H-pyrrol-2-yl)methylene]-2H-indol-2-one (AAA)

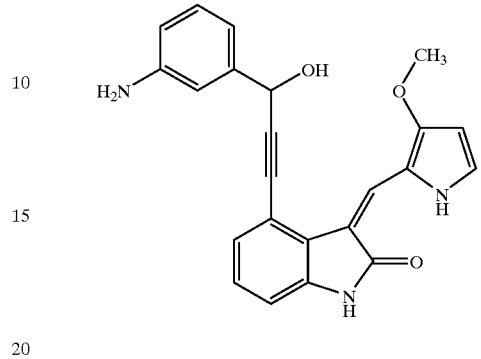

rac-(Z)-1,3-Dihydro-4-[3-hydroxy-3-(3-nitrophenyl)-1-propynyl]-3-[(3-methoxy-1H-pyrrol-2-yl)methylene]-2H-indol-2-one (25 mg, 0.068 mmol) (from Example 60) was added to 10% H$_2$O in methanol (2 mL) and to this mixture was added zinc dust (35 mg, 0.53 mmol) and ammonium chloride (10 mg, 0.19 mmol). The reaction was heated at reflux for 3 h, at which time the reaction was cooled and the solid was filtered off. The solids were washed extensively with ethyl acetate, and the ethyl acetate and methanol were evaporated in vacuo. The resulting precipitate was filtered off, dried and recrystallized from ethyl acetate/hexane to give rac-(Z)-4-[3-(3-aminophenyl)-3-hydroxy-1-propynyl]-1,3-dihydro-3-[(3-methoxy-1H-pyrrol-2-yl)methylene]-2H-indol-2-one. (Yield 19 mg, 73%).

Example 62

Synthesis of 3-(4-Acetamidophenyl)-3-hydroxy-1-propyne

Step A:

1-(4-Nitro-phenyl)-2-propyn-1-ol (4.89 mmol) (prepared by the addition of ethynylmagnesium chloride (Aldrich) to 4-nitrobenzaldehyde (Aldrich) according to method A above) was added to 10% H$_2$O in methanol (150 mL) and to this mixture was added zinc dust (44.01 mmol) and ammonium chloride (10.67 mmol). The reaction was heated at reflux for 3 h, at which time the reaction was cooled and the solid was filtered off. The solids were washed extensively with ethyl acetate, and the ethyl acetate and methanol were evaporated in vacuo. The resulting precipitate was filtered off, dried and recrystallized from ethyl acetate/hexane to yield 1-(4-amino-phenyl)-2-propyn-1-ol.

Step B:

1-(4-Amino-phenyl)-2-propyn-1-ol (3.0 mmol) (from Step A above) was dissolved in dry THF (20 mL) and DMF (1 mL). Acetic anhydride (4.2 mmol) was added dropwise followed by triethylamine (3.0 mmol). The reaction was stirred at room temperature for 2 h, after which time water (30 mL) was added, and the THF was evaporated in vacuo. The aqueous layer was extracted with ethyl acetate (3×50 mL), and the combined organic layers were dried over magnesium sulfate and concentrated. The resulting product, 3-(4-acetamidophenyl)-3-hydroxy-1-propyne, was purified via flash column chromatography (SiO$_2$, 230–400 mesh) with ethyl acetate/hexane.

Example 63

Synthesis of rac-(Z)-4-[3-(4-Acetamidophenyl)-3-hydroxy-1-propynyl]-1,3-dihydro-3-[(3-methoxy-1H-pyrrol-2-yl)methylene]-2H-indol-2-one (BBB)

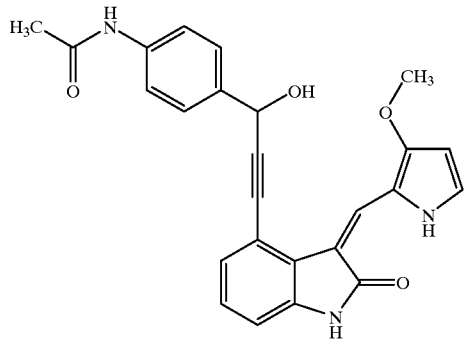

Using Method C above, 3-(4-acetamidophenyl)-3-hydroxy-1-propyne (111 mg, 0.59 mmol) (from Example 62 above) was coupled to (Z)-1,3-dihydro-4-iodo-3-[(3-methoxy-1H-pyrrol-2-yl)methylene]-2H-indol-2-one (110 mg, 0.3 mmol) (Starting Material 2) using $(Ph_3P)_2PdCl_2$ (25 mg) (Aldrich) and CuI (10 mg) (Aldrich) as catalyst in DMF (3 mL) and $Et_3N$ (3 mL) as solvent at 70° C. for 16 h, yielding rac-(Z)-4-[3-(4-acetamidophenyl)-3-hydroxy-1-propynyl]-1,3-dihydro-3-[(3-methoxy-1H-pyrrol-2-yl)methylene]-2H-indol-2-one. (Yield 57 mg, 44%).

Example 64

Synthesis of (Z)-1,3-Dihydro-3-[(3-methoxy-1H-pyrrol-2-yl)methylene]-4-[(3-pyridinyl)ethynyl]-2H-indol-2-one (CCC)

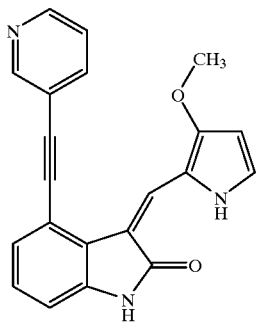

Using Method D above, 3-ethynyl pyridine (60.6 mg, 0.59 mmol) (see below) was coupled with (Z)-4-bromo-1,3-dihydro-3-[(3-methoxy-1H-pyrrol-2-yl)methylene]-2H-indol-2-one (75 mg, 0.23 mmol) (Starting Material 1) using $(Ph_3P)_4Pd$ (13.3 mg) (Aldrich) and CuI (3 mg) (Aldrich) as catalyst in DMF (4 mL) and $Et_3N$ (4 mL) as solvent at 100° C. for 18 h, to yield (Z)-1,3-dihydro-3-[(3-methoxy-1H-pyrrol-2-yl)methylene]-4-[(3-pyridinyl)ethynyl]-2H-indol-2-one. (Yield 52 mg, 66%).

3-Ethynyl pyridine was prepared by coupling 2-methyl-3-butyne-2-ol to 3-bromopyridine using $(Ph_3P)_2PdCl_2$ (Aldrich) and CuI (Aldrich) as catalyst in DMF and $Et_3N$ as solvent according to method D above.

Example 65

Synthesis of (Z)-1,3-Dihydro-3-[(3-methoxy-1H-pyrrol-2-yl)methylene]-4-[(2-pyridinyl)ethynyl]-2H-indol-2-one (DDD)

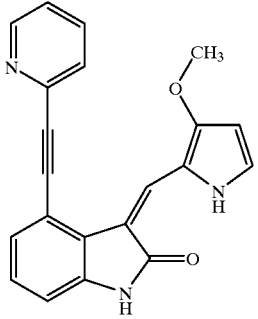

Using Method J above, 2-bromopyridine (44.9 mg, 0.28 mmol) (Aldrich) was coupled with (Z)-1,3-dihydro-4-ethynyl-3-[(3-methoxy-1H-pyrrol-2-yl)methylene]-2H-indol-2-one (Starting Material 5) (50 mg, 0.19 mmol) using $DPPFPdCl_2$ (7.7 mg) (Aldrich) and CuI (2 mg) (Aldrich) as catalyst in DMF (3 mL) and $Et_3N$ (3 mL) as solvent and heating at reflux for 2 days, yielding (Z)-1,3-dihydro-3-[(3-methoxy-1H-pyrrol-2-yl)methylene]-4-[(2-pyridinyl)ethynyl]-2H-indol-2-one. (Yield 30 mg, 47%).

Example 66

Synthesis of (Z)-1,3-Dihydro-3-[(3-methoxy-1H-pyrrol-2-yl)methylene]-4-[(4-pyridinyl)ethynyl]-2H-indol-2-one (EEE)

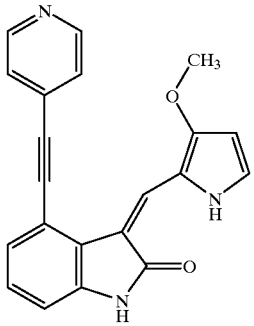

Using Method J above, 4-bromopyridine hydrochloride (110 mg, 0.57 mmol) (Aldrich) was coupled with (Z)-1,3-dihydro-4-ethynyl-3-[(3-methoxy-1H-pyrrol-2-yl)methylene]-2H-indol-2-one (Starting Material 5) (100 mg, 0.38 mmol) using $DPPFPdCl_2$ (15.4 mg) (Aldrich) and CuI (4 mg) (Aldrich) as catalyst in DMF (5 mL) and $Et_3N$ (5 mL) as solvent and heating at reflux for 1 day, yielding (Z)-1,3-dihydro-3-[(3-methoxy-1H-pyrrol-2-yl)methylene]-4-[(4-pyridinyl)ethynyl]-2H-indol-2-one. (Yield 70 mg, 54%).

Example 67

Synthesis of rac-(Z)-1,3-Dihydro-4-(3-hydroxy-3-phenyl-1-propynyl)-3-[(3-methoxy-1H-pyrrol-2-yl)methylene]-2H-indol-2-one (FFF)

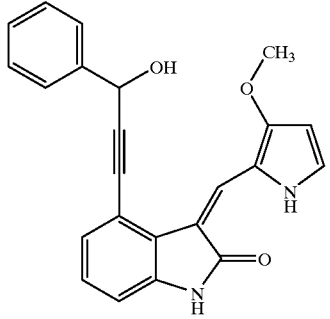

Using Method D above, 3-hydroxy-3-phenyl-1-propyne (0.1 g, 0.78 mmol) (prepared by the addition of ethynylmagnesium chloride (Aldrich) to benzaldehyde (Aldrich) through Method A above) was coupled to (Z)-4-bromo-1,3-dihydro-3-[(3-methoxy-1H-pyrrol-2-yl)methylene]-2H-indol-2-one (0.1 g, 0.31 mmol) (Starting Material 1) using DPPFPdCl$_2$ (12.6 mg) (Aldrich) and CuI (3 mg) (Aldrich) as catalyst in DMF (5 mL) and Et$_3$N (5 mL) as solvent at 85° C. for 18 h, yielding rac-(Z)-1,3-dihydro-4-(3-hydroxy-3-phenyl-1-propynyl)-3-[(3-methoxy-1H-pyrrol-2-yl)methylene]-2H-indol-2-one. (Yield 42 mg, 38%).

Example 68

Synthesis of (Z)-1,3-Dihydro-3-[(3-methoxy-1H-pyrrol-2-yl)methylene]-5-nitro-4-[(3-pyridinyl)ethynyl]-2H-indol-2-one (GGG)

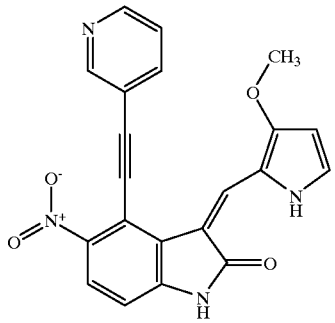

Using Method D above, 3-ethynyl pyridine (0.14 g, 1.38 mmol) (see Example 64) was coupled with (Z)-4-bromo-1,3-dihydro-3-[(3-methoxy-1H-pyrrol-2-yl)methylene]-5-nitro-2H-indol-2-one (0.2 g, 0.55 mmol) (Starting Material 3) using (Ph$_3$P)$_4$Pd (31.8 mg) (Aldrich) and CuI (5.3 mg) (Aldrich) as catalyst in DMF (6 mL) and Et$_3$N (6 mL) as solvent and at 85° C. for 18 h, yielding (Z)-1,3-dihydro-3-[(3-methoxy-1H-pyrrol-2-yl)methylene]-5-nitro-4-[(3-pyridinyl)ethynyl]-2H-indol-2-one. (Yield 0.16 g, 71%).

Example 69

Synthesis of (Z)-5-Amino-1,3-dihydro-3-[(3-methoxy-1H-pyrrol-2-yl)methylene]-4-[(3-pyridinyl)ethynyl]-2H-indol-2-one (HHH)

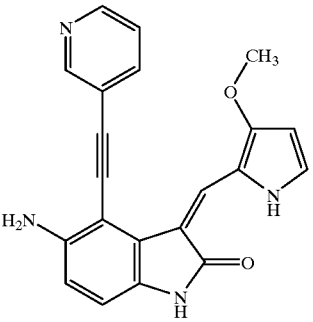

Using Method L above, (Z)-1,3-dihydro-3-[(3-methoxy-1H-pyrrol-2-yl)methylene]-5-nitro-4-[(3-pyridinyl)ethynyl]-2H-indol-2-one (0.1 g, 0.26 mmol) (from Example 68 above) was reduced with Zn (0.15 g, 2.33 mmol) and NH$_4$Cl (30.6 mg, 0.57 mmol) in 10% water in methanol (10 mL) with a trace of DMF and heating at 90° C. for 5 h, to yield (Z)-5-amino-1,3-dihydro-3-[(3-methoxy-1H-pyrrol-2-yl)methylene]-4-[(3-pyridinyl)ethynyl]-2H-indol-2-one. (Yield 28 mg, 30%).

Example 70

Synthesis of (Z-N-[2,3-Dihydro-3-[(3-methoxy-1H-pyrrol-2-yl)methylene]-2-oxo-4-[(3-pyridinyl)ethynyl]-1H-indol-5-yl]-2-thiopheneacetamide (III)

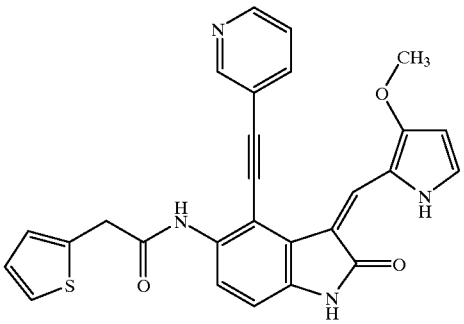

Using Method M above, (Z)-5-amino-1,3-dihydro-3-[(3-methoxy-1H-pyrrol-2-yl)methylene]-4-[(3-pyridinyl)ethynyl]-2H-indol-2-one (18 mg, 0.051 mmol) (from Example 69) was coupled with 2-thiopheneacetyl chloride (16.2 mg, 0.10 mmol) (Aldrich) in THF (2 mL) and saturated aqueous sodium bicarbonate (1 mL) at room temperature for 1 h, to yield (Z)-N-[2,3-dihydro-3-[(3-methoxy-1H-pyrrol-2-yl)methylene]-2-oxo-4-[(3-pyridinyl)ethynyl]-1H-indol-5-yl]-2-thiopheneacetamide. (Yield 7.7 mg, 32%).

Example 71

Synthesis of (Z)-1,3-Dihydro-4-iodo-3-[(1H-pyrrol-2-yl)methylene]-2H-indol-2-one (JJJ)

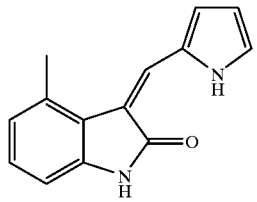

A mixture of 4-iodooxindole (404.1 mg, 1.56 mmol) (see Fukuyama, supra) and pyrrole-2-carboxaldehyde (163.2 mg, 1.72 mmol) (Aldrich) in 2-propanol (6.2 mL) was treated with 2 drops of piperidne. The reaction mixture was heated at reflux for 24 h and then allowed to cool to 23° C., at which time, the reaction mixture was filtered. The solid was washed several times with cold distilled water and then allowed to air dry to provide pure (Z)-1,3-dihydro-4-iodo-3-[(1H-pyrrol-2-yl)methylene]-2H-indol-2-one (341.8 mg, 65%) as a yellow solid which was used without further purification:

Example 72

Synthesis of 4-[(E)-2-(2-Chlorophenyl)-ethenyl]-1,3-dihydro-(Z)-3-[(1H-pyrrol-2-yl)methylene]-2H-indol-2-one (KKK)

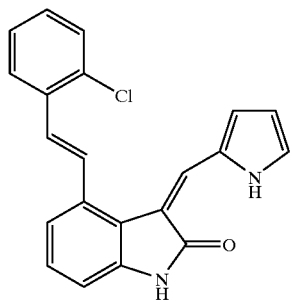

A solution of (Z)-1,3-dihydro-4-iodo-3-[(1H-pyrrol-2-yl)methylene]-2H-indol-2-one (39 mg, 0.116 mmol) (from Example 71 above), triethylamine (65 µL, 0.464 mmol), tri-o-tolylphosphine (7 mg, 0.023 mmol) (Aldrich), palladium(ll) acetate (2 mg, 0.009 mmol) (Aldrich), and 2-chlorostyrene (24 mg, 0.173 mmol) (Aldrich) in 3 mL of dry N,N-dimethylformamide was heated at 85° C. under a nitrogen atmosphere for 20 h. The reaction mixture was allowed to cool to room temperature and then directly purified by flash chromatography (Merck Silica gel 60, 230–400 mesh, 5% ethyl acetate-benzene elution) to yield pure 4-[(E)-2-(2-chlorophenyl)-ethenyl]-1,3-dihydro-(Z)-3-[(1H-pyrrol-2-yl)methylene]-2H-indol-2-one as a yellow solid. (Yield 27 mg, 67%; mp=257–258° C.).

Example 73

Synthesis of 1,3-Dihydro-(Z)-3-[(1H-pyrrol-2yl)methylene]-[(E)-2-phenylethenyl]-2H-indol-2-one (LLL)

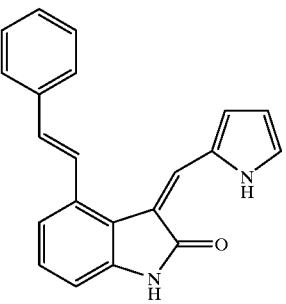

To a stirred solution of (Z)-1,3-dihydro-4-iodo-3-[(1H-pyrrol-2-yl)methylene]-2H-indol-2-one (from Example 71 above) (500 mg, 1.49 mmol) in DMF (8 mL) and TEA (3 mL) was added styrene (0.34 mL, 2.98 mmol) (Aldrich), tri-o-tolylphosphine (361 mg, 1.19 mmol) (Aldrich) and Pd(OAc)$_2$ (67 mg, 0.30 mmol) (Aldrich). The reaction mixture was stirred at 85° C. overnight in a pressure tube. The solvent was removed in vacuo, and the residue was purified by silica gel chromatography (Hex:EtOAc 5:1) to 1,3-dihydro-(Z)-3-[(1H-pyrrol-2yl)methylene]-[(E)-2-phenylethenyl]-2H-indol-2-one. (Yield 371 mg, 80%).

Example 74

Synthesis of 1,3-Dihydro-(Z)-3-[(3-methoxy-1H-pyrrol-2yl)methylene]-[(E)-2-phenylethenyl]-2H-indol-2-one (MMM)

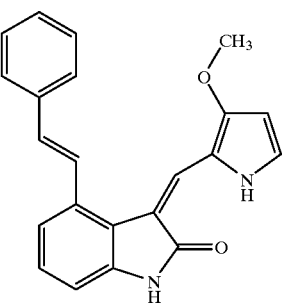

To a stirred solution of (Z)-1,3-dihydro-4-iodo-3-[(3-methoxy-1H-pyrrol-2-yl)methylene]-2H-indol-2-one (500 mg, 1.49 mmol) (Starting Material 2) in DMF (8 mL) and TEA (3 mL) was added styrene (0.33 mL, 2.92 mmol) (Aldrich), tri-o-tolylphosphine (361 mg, 1.19 mmol) (Aldrich) and Pd(OAc)$_2$ (67 mg, 0.30 mmol) (Aldrich). The reaction mixture was stirred at 85° C. overnight in a pressure tube. The solvent was removed in vacuo, and the residue was purified by silica gel chromatography (Hex:EtOAc=5:1) to provide 1,3-dihydro-(Z)-3-[(3-methoxy-1H-pyrrol-2yl)methylene]-[(E)-2-phenylethenyl]-2H-indol-2-one as a yellow solid. (Yield 407 mg, 80%).

Example 75

Synthesis of 1,3-Di hydro-4-[(E)-2-(4-methoxyphenyl)-ethenyl]-(Z)-3-[(1H-pyrrol-2-yl)methlene]-2H-indol-2-one (NNN)

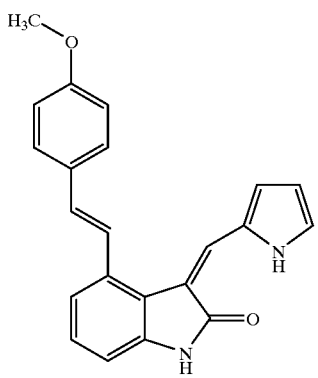

A. p-Methoxy-styrene

To a stirred solution of n-butyllithium (4 mL, 2,5 M solution in Hexane, 10 mmol) (Aldrich) in ether (30 mL) was added methyltriphenylphosphonium bromide (3.57 g, 10 mmol) (Aldrich) over a period of 5 min. The reaction mixture was stirred for 4 h at room temperature. To the resulting orange solution was added 4-methoxybenzaldehyde (1.34 mL, 10 mmol) (Aldrich) dropwise. The solution became colorless, and a white precipitate separated. The mixture was then heated to reflux and immediately allowed to cool to room temperature. The precipitate was removed by filtration. The precipitate was washed with ether and the combined ethereal filtrates were washed with water until neutral and then dried over anhydrous MgSO$_4$. The solvent was removed, and the residue was used in the next reaction without further purification.

B. 1,3-Dihydro-4-[(E)-2-(4-methoxyphenyl)-ethenyl]-(Z)-3-[(1H-pyrrol-2-yl)methlene]-2H-indol-2-one (NNN)

To a stirred solution of (Z)-1,3-dihydro-4-iodo-3-[(1H-pyrrol-2-yl)methylene]-2H-indol-2-one (from Example 71 above) (100 mg, 0.29 mmol) in DMF (3 mL) and TEA (2 mL) was added p-methoxy-styrene (79 mg, 0.58 mmol) (from Step A above), tri-o-tolylphosphine (107 mg, 0.35 mmol) (Aldrich) and Pd(OAc)$_2$ (20 mg, 0.089 mmol) (Aldrich). The reaction mixture was stirred at 85° C. overnight in a pressure tube. The solvent was removed in vacuo, and the residue was purified by silica gel chromatography (Hex:EtOAc=5:1) to provide 1,3-dihydro-4-[(E)-2-(4-methoxyphenyl)-ethenyl]-(Z)-3-[(1H-pyrrol-2-yl)methlene]-2H-indol-2-one as a yellow solid. (Yield 72 mg, 73%).

Example 76

Synthesis of 1,3-Dihydro-(Z)-3-[(3-methoxy-1H-pyrrol-2-yl)methylene]-4-[(E)-2-(4-methoxyphenyl)-ethenyl]-2H-indol-2-one (OOO)

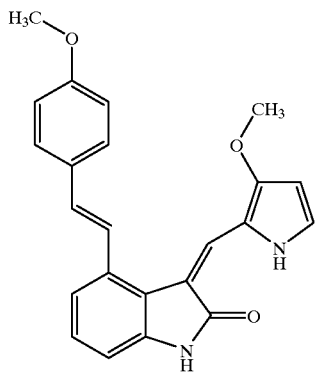

To a stirred solution of (Z)-1,3-dihydro-4-iodo-3-[(3-methoxy-1H-pyrrol-2-yl)methylene]-2H-indol-2-one (100 mg, 0.29 mmol) (Starting Material 2) in DMF (3 mL) and TEA (2 mL) was added p-methoxy-styrene (79 mg, 0.58 mmol) (from Example 75A, above), tri-o-tolylphosphine (107 mg, 0.35 mmol) (Aldrich) and Pd(OAc)$_2$ (20 mg, 0.089 mmol) (Aldrich). The reaction mixture was stirred at 85° C. overnight in a pressure tube. The solvent was removed in vacuo, and the residue was purified by silica gel chromatography (Hex:EtOAc=5:1) to provide 1,3-dihydro-(Z)-3-[(3-methoxy-1H-pyrrol-2-yl)methylene]-4-[(E)-2-(4-methoxy-phenyl)-ethenyl]-2H-indol-2-one as a yellow solid. (Yield 78 mg, 74%).

Example 77

Synthesis of 4-Ethenyl-benzoic acid methyl ester

To a stirred solution of n-butyllithium (4 mL, 2,5 M solution in hexane, 10 mmol) (Aldrich) in ether (30 mL) was added methyltriphenylphosphonium bromide (3.57 g, 10 mmol) (Aldrich) over a period of 5 min. The reaction mixture was stirred for 4 h at room temperature. To the resulting orange solution was added methyl 4-formylbenzoate (1.54 mL, 10 mmol) dropwise. The solution became colorless, and a white precipitate separated. The mixture was then heated to reflux and immediately allowed to cool to room temperature. The precipitate was removed by filtration. The resulting precipitate was washed with ether, and the combined ethereal filtrates were washed with water until neutral and then dried over anhydrous MgSO$_4$. The solvent was removed and the residue, 4-ethenyl-benzoic acid methyl ester, was used in the next reaction without further purification.

Example 78

Synthesis of 4-[(E)-2-[2,3-Dihydro-(Z)-3-[(3-methoxy-1H-pyrrol-2-yl)methylene]-2-oxo-1H-indol-4-yl]ethenyl]benzoic acid methyl ester (PPP)

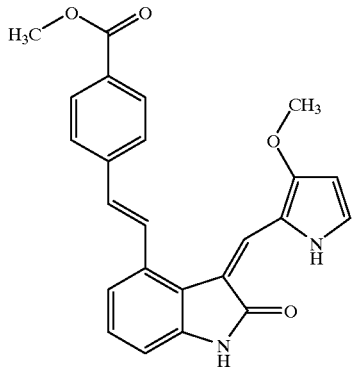

To a stirred solution of (Z)-1,3-dihydro-4-iodo-3-[(3-methoxy-1H-pyrrol-2-yl)methylene]-2H-indol-2-one (100 mg, 0.29 mmol) (Starting Material 2) in DMF (3 mL) and TEA (2 mL) was added 4-ethenyl-benzoic acid methyl ester (0.11 mL, 0.58 mmol)(from Example 77 above), tri-o-tolylphosphine (107 mg, 0.35 mmol) (Aldrich) and Pd(OAc)$_2$ (20 mg, 0.089 mmol) (Aldrich). The reaction mixture was stirred at 85° C. overnight in a pressure tube. The solvent was removed in vacuo, and the residue was purified by silica gel chromatography (Hex:EtOAc=5:1) to provide 4-[(E)-2-[2,3-dihydro-(Z)-3-[(3-methoxy-1H-pyrrol-2-yl)methylene]-2-oxo-1H-indol-4-yl]ethenyl] benzoic acid methyl ester as a yellow solid. (Yield 77 mg, 66%)

Example 79

Synthesis of 1,2-Dimethoxy-4-ethenyl-benzene

To a stirred solution of n-butyllithium (4 mL, 2,5 M solution in hexane, 10 mmol) (Aldrich) in ether (30 mL) was added methyltriphenylphosphonium bromide (3.57 g, 10 mmol) (Aldrich) over a period of 5 min. The reaction mixture was stirred for 4 h at room temperature. To the resulting orange solution was added 3,4-dimethoxybenzaldehyde (1.82 g, 11 mmol) (Aldrich) dropwise. The solution became colorless, and a white precipitate separated. The mixture was then heated to reflux and immediately allowed to cool to room temperature. The precipitate was removed by filtration. The precipitate was washed with ether and the combined ethereal filtrates were washed with water until neutral and then dried over anhydrous MgSO$_4$. The solvent was removed and the residue, 1,2-dimethoxy-4-ethenyl -benzene, was used in the next reaction without further purification.

Example 80

Synthesis of 1,3-Dihydro-4-[(E)-2-(3,4-dimethoxyphenyl)-ethenyl]-(Z)-3-[(3-methoxy-1H-pyrrol-2-yl)methylene]-2H-indol-2-one (QQQ)

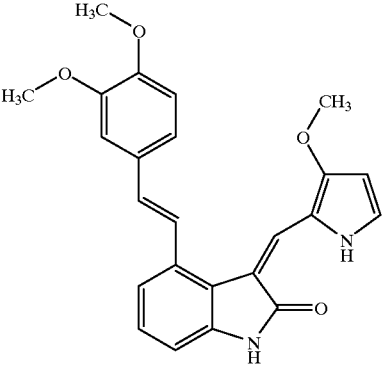

To a stirred solution of (Z)-1,3-dihydro-4-iodo-3-[(3-methoxy-1H-pyrrol-2-yl)methylene]-2H-indol-2-one (100 mg, 0.29 mmol) (Starting Material 2) in DMF (3 mL) and TEA (2 mL) was added 1,2-dimethoxy-4-vinyl-benzene (0.089 mg, 0.58 mmol) (from Example 79), tri-o-tolylphosphine (107 mg, 0.35 mmol) (Aldrich) and Pd(OAc)$_2$ (20 mg, 0.089 mmol) (Aldrich). The reaction mixture was stirred at 85° C. overnight in a pressure tube. The solvent was removed in vacuo, and the residue was purified by silica gel chromatography (Hex:EtOAc=5:1) to provide 1,3-dihydro-4-[(E)-2-(3,4-dimethoxyphenyl)-ethenyl]-(Z)-3-[(3-methoxy-1H-pyrrol-2-yl)methylene]-2H-indol-2-one as a yellow solid. (Yield 78 mg, 67%).

Example 81

Synthesis of (Z)-1,3-Dihydro-3-[(1H-pyrrol-2-yl)methylene]-5-(trimethylsilyl)ethynyl-2H-indol-2-one (RRR)

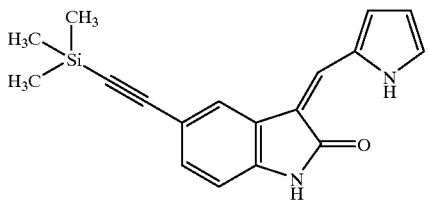

(Trimethylsilyl)acetylene (1.36 g,13.8 mmol) (Aldrich) and (Z)-5-bromo-1,3-dihydro-3-[(1H-pyrrol-2-yl) methylene]-2H-indol-2-one (2.0 g, 6.9 mmol) (Starting Material 7) were dissolved in 30 mL DMF and 40 mL triethylamine. The solution was degassed for 30 minutes by bubbling argon through the solution. At this time CuI (130 mg, 0.68 mmol) (Aldrich) and (Ph$_3$P)$_2$PdCl$_2$ (400 mg, 0.57 mmol) (Aldrich) were added, and the reaction was heated, under argon, at 70° C. for 22 hours. Water (20 mL) was then added and the precipitate was filtered off and dried. The product was purified via flash column chromatography (SiO$_2$, 230–400 mesh) with 1% MeOH/CHCl$_3$ to give (Z)-1,3-dihydro-3-[(1H-pyrrol-2-yl)methylene]-5-(trimethylsilyl)ethynyl-2H-indol-2-one as a yellow powder. (Yield 1.07 g, 51%).

Example 82

Synthesis of (Z)-1,3-Dihydro-5-ethynyl-3-[(1H-pyrrol-2-yl)methylene]-2H-indol-2-one (SSS)

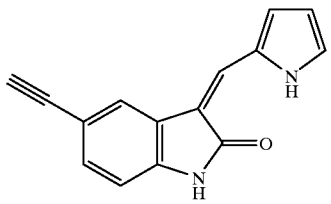

To a solution of (Z)-1,3-dihydro-3-[(1H-pyrrol-2-yl)methylene]-5-(trimethylsilyl)ethynyl-2H-indol-2-one (940 mg, 3.1 mmol) (from Example 81 above) in 50 mL ethanol and 15 mL tetrahydrofuran (Fisher Scientific) was added dropwise a solution of silver nitrate (1.17 g, 6.89 mmol) in 5 mL water and 15 mL ethanol, during which time a precipitate formed. The mixture was stirred at room temperature for 45 minutes, after which a solution of potassium cyanide (2.18 g, 33.47 mmol) in 8 mL of water was added and the precipitated dissolved. To the solution was then added 50 mL of a saturated aqueous sodium bicarbonate solution followed by 500 mL of water. The product was then filtered off and dried to give (Z)-1,3-dihydro-5-ethynyl-3-[(1H-pyrrol-2-yl)methylene]-2H-indol-2-one (yield 700 mg, 96%), which was recrystallized from EtOAc/Hex to yield 540 mg of the product as yellow crystals.

Example 83

Synthesis of (Z)-1,3-Dihydro-5-(4-hydroxyphenyl)ethynyl-3-[(1H-pyrrol-2-yl)methylene]-2H-indol-2-one (TTT)

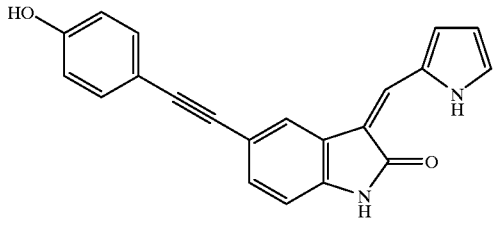

A solution of (Z)-1,3-dihydro-5-ethynyl-3-[(1H-pyrrol-2-yl)methylene]-2H-indol-2-one (100 mg, 0.43 mmol) (from Example 82) and 4-iodophenol (104 mg, 0.47 mmol) (Aldrich) in N,N-dimethylformamide (2 mL) and triethylamine (2 mL) was degassed by bubbling argon through the solution for 15 minutes. Copper(I) iodide (8 mg, 0.042 mmol) (Aldrich) and (Ph$_3$P)$_2$PdCl$_2$ (25 mg, 0.021 mmol) (Aldrich) were added, and the reaction was heated at 70° C. for 16 hours. Water (15 mL) was then added and the precipitate was filtered off and dried. The product was purified via flash column chromatography (SiO$_2$, 230–400 mesh) with ethyl acetate/hexane to give (Z)-1,3-dihydro-5-(4-hydroxyphenyl)ethynyl-3-[(1H-pyrrol-2-yl)methylene]-2H-indol-2-one as a yellow powder. (Yield 121 mg, 86%).

Example 84

Synthesis of (Z)-1,3-Dihydro-5-(3-nitrophenyl)ethynyl-3-[(1H-pyrrol-2-yl)methylene]-2H-indol-2-one (UUU)

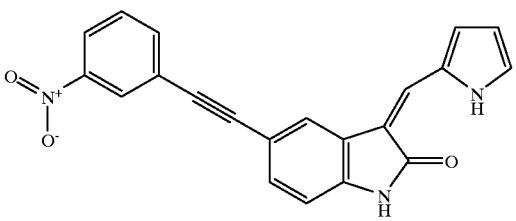

This compound was prepared in a manner analogous to the preparation of (Z)-1,3-dihydro-5-(4-hydroxyphenyl)ethynyl-3-[(1H-pyrrol-2-yl)methylene]-2H-indol-2-one (Compound TTT in Example 83 above). In this example, (Z)-1,3-dihydro-5-ethynyl-3-[(1H-pyrrol-2-yl)methylene]-2H-indol-2-one (150 mg, 0.64 mmol) (from Example 82) was coupled with 1-iodo-3-nitrobenzene (175 mg, 0.70 mmol) (Aldrich) using CuI (13 mg, 0.068 mmol) and (Ph$_3$P)$_2$PdCl$_2$ (22 mg, 0.031 mmol) (Aldrich) as catalyst in 3 mL DMF and 3 mL triethylamine at 70° C. for 13 hours to give (Z)-1,3-dihydro-5-(3-nitrophenyl)ethynyl-3-[(1H-pyrrol-2-yl)methylene]-2H-indol-2-one as a red powder. (Yield 148 mg, 65%)

Example 85

Synthesis of (Z)-1,3-Dihydro-5-phenylethynyl-3-[(1H-pyrrol-2-yl)methylene]-2H-indol-2-one (VVV)

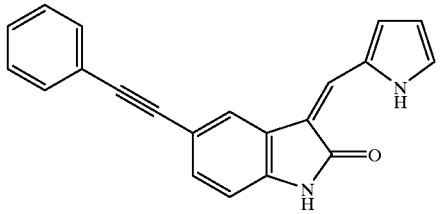

This compound was prepared in a manner analogous to the preparation of (Z)-1,3-dihydro-5-(4-hydroxyphenyl)ethynyl-3-[(1H-pyrrol-2-yl)methylene]-2H-indol-2-one in Example 83 above. In this example, (Z)-1,3-dihydro-5-ethynyl-3-[(1H-pyrrol-2-yl)methylene]-2H-indol-2-one (90 mg, 0.38 mmol) (from Example 82) was coupled with iodobenzene (219 mg, 1.07 mmol) (Aldrich) using CuI (8 mg, 0.042 mmol) (Aldrich) and (Ph$_3$P)$_2$PdCl$_2$ (14 mg, 0.020 mmol) (Aldrich) as catalyst in 1 mL DMF and 2 mL triethylamine at 70° C. for 15 hours to give (Z)-1,3-dihydro-5-phenylethynyl-3-[(1H-pyrrol-2-yl)methylene]-2H-indol-2-one as a yellow powder. (Yield 92 mg, 78%)

Example 86

Synthesis of (Z)-1,3-Dihydro-5-(3-hydroxyphenyl)ethynyl-3-[(1H-pyrrol-2-yl)methylene]-2H-indol-2-one (WWW)

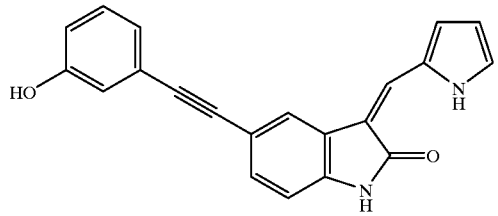

This compound was also prepared in a manner to analogous to the preparation of (Z)-I,3-dihydro-5-(4-hydroxyphenyl)ethynyl-3-[(1H-pyrrol-2-yl)methylene]-2H-indol-2-one in Example 83 above. In this example, (Z)-1,3-dihydro-5-ethynyl-3-[(1H-pyrrol-2-yl)methylene]-2H-indol-2-one (100 mg, 0.43 mmol) (from Example 82) was coupled with 3-iodophenol (110 mg, 0.50 mmol) (Aldrich) using CuI (8 mg, 0.042 mmol) (Aldrich) and $(Ph_3P)_2PdCl_2$ (15 mg, 0.021 mmol) (Aldrich) as catalyst in 1 mL DMF and 3 mL triethylamine at 70° C. for 13 hours to give (Z)-1,3-dihydro-5-(3-hydroxyphenyl)ethynyl-3-[(1H-pyrrol-2-yl)methylene]-2H-indol-2-one as a yellow powder. (Yield 100 mg, 71%).

Example 87

Synthesis of (Z)-1,3-Dihydro-5-(2-nitrophenyl)ethynyl-3-[(1H-pyrrol-2-yl)methylene]-2H-indol-2-one (XXX)

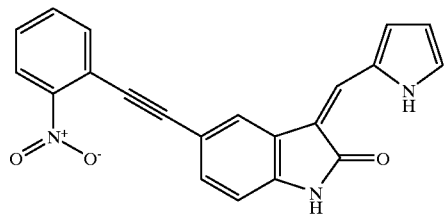

This compound was also prepared in a manner analogous to the preparation of (Z)-1,3-dihydro-5-(4-hydroxyphenyl)ethynyl-3-[(1H-pyrrol-2-yl)methylene]-2H-indol-2-one in Example 83 above. In this example, (Z)-1,3-dihydro-5-ethynyl-3-[(1H-pyrrol-2-yl)methylene]-2H-indol-2-one (150 mg, 0.64 mmol) (from Example 82) was coupled with 1-bromo-2-nitrobenzene (150 mg, 0.74 mmol) (Aldrich) using CuI (13 mg, 0.068 mmol) (Aldrich) and $(Ph_3P)_2PdCl_2$ (22 mg, 0.031 mmol) (Aldrich) as catalyst in 2 mL DMF and 4 mL triethylamine at 70° C. for 15 hours to give (Z)-1,3-dihydro-5-(2-nitrophenyl)ethynyl-3-[(1H-pyrrol-2-yl)methylene]-2H-indol-2-one as a red powder. (Yield 115 mg, 51%).

Example 88

Synthesis (Z)-5-[3-[2,3-dihydro-2-oxo-3-(1H-pyrrol-2-ylmethylene)-1H-indol-5-yl]-2-propynyl]-6(5H)-phenanthridinone (YYY)

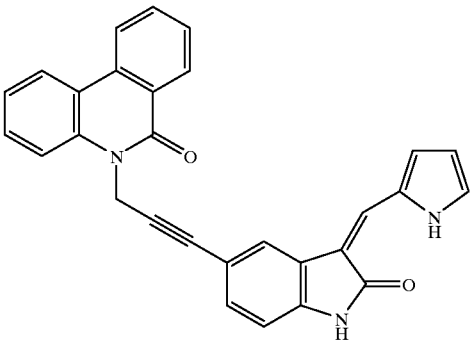

A solution of 5-(2-propynyl)-6(5H)-phenanthridinone (42 mg, 0.18 mmol) (prepared according to Walser et al., *J. Med. Chem.*, 34(3), 1209–1221 (1991)) and (Z)-1,3-dihydro-5-iodo-3-[(1H-pyrrol-2-yl)methylene]-2H-indol-2-one (2.0 g, 0.12 mmol) (Starting Material 8) were dissolved in 3 mL DMF and 0.04 mL triethylamine.

The solution was degassed for 30 minutes by bubbling argon through the solution. At this time, CuI (1 mg) (Aldrich), triphenylphosphine (5 mg) (Aldrich), and palladium(II) acetate (2 mg) (Aldrich) were added, and the reaction was stirred, under argon, at 27° C. for 37 hours. Water (20 mL) was then added and the precipitate was filtered off and dried. The product was purified via flash column chromatography ($SiO_2$, 230–400 mesh) with 5% MeOH in $CHCl_3$ to give (Z)-5-[3-[2,3-dihydro-2-oxo-3-(1H-pyrrol-2-ylmethylene)-1H-indol-5-yl]-2-propynyl]-6(5H)-phenanthridinone as a yellow powder. (Yield 13 mg, 25%)

Example 89

Synthesis of (Z)-1,3-Dihydro-5-(4-nitrophenyl)ethynyl-3-[(1H-pyrrol-2-yl)methylene]-2H-indol-2-one (ZZZ)

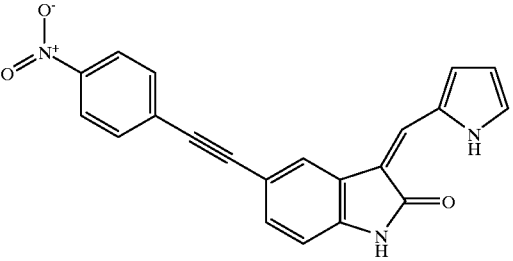

A solution of (Z)-1,3-dihydro-5-ethynyl-3-[(1H-pyrrol-2-yl)methylene]-2H-indol-2-one (150 mg, 0.64 mmol) (from Example 82) and 1-iodo-4-nitrobenzene (175 mg, 0.70 mmol) (Aldrich) in N,N-dimethylformamide (3 mL) (Fisher Scientific) and triethylamine (3 mL) was degassed by bubbling argon through the solution for 15 minutes. Copper(I) iodide (13 mg, 0.068 mmol) (Aldrich) and $(Ph_3P)_2PdCl_2$ (22 mg, 0.031 mmol) (Aldrich) were added, and the reaction mixture was heated at 70° C. for 13 hours. Water (15 mL)

was then added and the precipitate was filtered off and dried. The product was purified via flash column chromatography (SiO$_2$, 230–400 mesh) with ethyl acetate/hexane to give (Z)-1,3-dihydro-5-(4-nitrophenyl)ethynyl-3-[(1H-pyrrol-2-yl)methylene]-2H-indol-2-one as a red powder. (Yield 111 mg, 49%).

Example 90

Synthesis of (Z)-5-(4-Aminophenyl)ethynyl-1,3-dihydro-3-[(1H-pyrrol-2-yl)methylene]-2H-indol-2-one (AAAA)

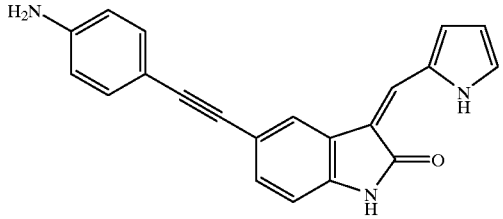

To a solution of (Z)-1,3-dihydro-5-(4-nitrophenyl)ethynyl-3-[(1H-pyrrol-2-yl)methylene]-2H-indol-2-one (45 mg, 0.13 mmol) (from Example 89) in 1 mL of a 10% water in methanol solution and 0.5 mL THF was added zinc dust (145 mg, 2.21 0 mmol) followed by ammonium chloride (25 mg, 0.47 mmol). The reaction was heated at gentle reflux for 4 hours, at which time the reaction mixture was filtered through a pad of Celite® (Fisher Scientific) and rinsed thoroughly with ethyl acetate. The resulting solution was diluted with 5 mL water and the product was extracted with ethyl acetate. The combined organic extracts were dried over magnesium sulfate and concentrated. The resulting powder was recrystallized from EtOAc/hex to give (Z)-5-(4-aminophenyl)ethynyl-1,3-dihydro-3-[(1H-pyrrol-2-yl)methylene]-2H-indol-2-one as a red powder. (Yield 24 mg, 56%).

Example 91

Synthesis of (Z)-5-Bromo-1,3-dihydro-3-[(3-methoxy-1H-pyrrol-2-yl)methylene]-2H-indol-2-one (BBBB)

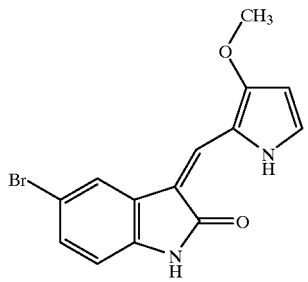

A mixture of 5-bromo-1,3-dihydro-2H-indol-2-one (0.94 g, 4.4 mmol) (Starting Material 6) and 3-methoxy-2-pyrrole-carboxyaldehyde (0.5 g, 4.0 mmol) (see Bellany et al., supra) in 1% piperidine in 2-propanol (10 mL) was heated at 65° C. for 16 h. Hot water (10 mL) was added. On cooling, the crystallized product was filtered off, washed with aqueous 2-propanol and dried. (Yield 1.13 g, 89%).

Example 92

Synthesis of (Z)-1,3-Dihydro-3-[(3-methoxy-1H-pyrrol-2-yl)methylene]-5-(trimethylsilyl)ethynyl-2H-indol-2-one (CCCC)

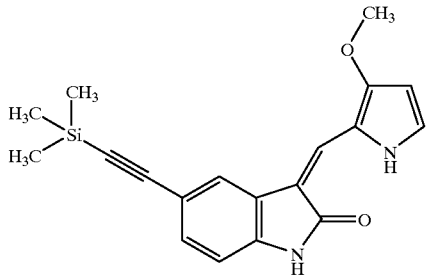

This compound was prepared in a manner analogous to the preparation of (Z)-1,3-dihydro-3-[(1H-pyrrol-2-yl)methylene]-5-(trimethylsilyl)-ethynyl-2H-indol-2-one in Example 81 above. In this example, (Z)-5-bromo-1,3-dihydro-3-[(3-methoxy-1H-pyrrol-2-yl)methylene]-2H-indol-2-one (740 mg, 2.32 mmol) (from Example 91) was coupled with (trimethylsilyl)acetylene (640 mg, 6.52 mmol) (Aldrich) using CuI (40 mg, 0.21 mmol) (Aldrich) and (Ph$_3$P)$_2$PdCl$_2$ (90 mg, 0.13 mmol) (Aldrich) as catalyst in 10 mL DMF and 10 mL triethylamine at 70° C. for 22 hours to give (Z)-1,3-dihydro-3-[(3-methoxy-1H-pyrrol-2-yl)methylene]-5-(trimethylsilyl)ethynyl-2H-indol-2-one. (Yield 410 mg, 52%).

Example 93

Synthesis of (Z)-1,3-Dihydro-5-ethynyl-3-[(3-methoxy-1H-pyrrol-2-yl)methylene]-2H-indol-2-one (DDDD)

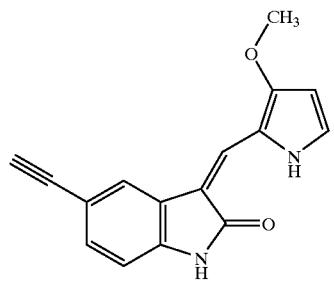

This compound was also prepared in a manner analogous to the preparation of (Z)-1,3-dihydro-5-ethynyl-3-[(1H-pyrrol-2-yl)methylene]-2H-indol-2-one in Example 82 above. In this example, (Z)-1,3-dihydro-3-[(3-methoxy-1H-pyrrol-2-yl)methylene]-5-(trimethylsilyl)ethynyl-2H-indol-2-one (100 mg, 0.3 mmol) (Example 92) in 5 mL ethanol and 1.5 mL tetrahydrofuran was treated with silver nitrate (0.112 g, 0.6 mmol) in 1.5 mL ethanol and 0.5 mL water, followed by potassium cyanide (218 mg, 3.35 mmol) in 1 mL water to give 70 mg (89%) of (Z)-1,3-dihydro-5-ethynyl-3-[(3-methoxy-1H-pyrrol-2-yl)methylene]-2H-indol-2-one (61 mg after recrystallization).

Example 94

Synthesis of (Z)-1,3-Dihydro-5-(3-pyridinyl) ethynyl-3-[(1H-pyrrol-2-yl)methylene]-2H-indol-2-one (EEEE)

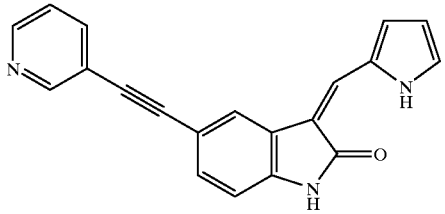

This compound was also prepared in a manner analogous to the preparation of (Z)-1,3-dihydro-5-(4-hydroxyphenyl) ethynyl-3-[(1H-pyrrol-2-yl)methylene]-2H-indol-2-one in Example 83 above. In this example, (Z)-1,3-dihydro-5-ethynyl-3-[(1H-pyrrol-2-yl)methylene]-2H-indol-2-one (47 mg, 0.21 mmol) (Example 82) was coupled with 3-bromopyridine (33 mg, 0.30 mmol) (Aldrich) using CuI (8 mg, 0.042 mmol) (Aldrich) and $(Ph_3P)_2PdCl_2$ (15 mg, 0.021 mmol) (Aldrich) as catalyst in 1 mL DMF and 1 mL triethylamine at 70° C. for 15 hours to give (Z)-1,3-dihydro-5-(3-pyridinyl)ethynyl-3-[(1H-pyrrol-2-yl)methylene]-2H-indol-2-one as a red powder. (Yield 30 mg, 47%).

Example 95

Synthesis of (Z)-1,3-Dihydro-5-(2-pyridinyl) ethynyl-3-[(1H-pyrrol-2-yl)methylene]-2H-indol-2-one (FFFF)

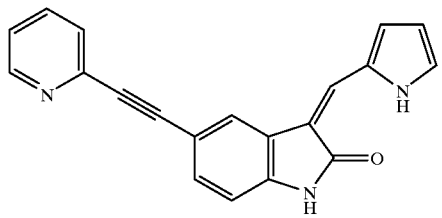

This compound was also prepared in a manner analogous to the preparation of (Z)-1,3-dihydro-5-(4-hydroxyphenyl) ethynyl-3-[(1H-pyrrol-2-yl)methylene]-2H-indol-2-one in Example 83 above. In this example, (Z)-1,3-dihydro-5-ethynyl-3-[(1H-pyrrol-2-yl)methylene]-2H-indol-2-one (40 mg, 0.17 mmol) (Example 82) was coupled with 2-bromopyridine (25 mg, 0.17 mmol) (Aldrich) using CuI (8 mg, 0.042 mmol) (Aldrich) and $(Ph_3P)_2PdCl_2$ (14 mg, 0.020 mmol) (Aldrich) as catalyst in 1 mL DMF and 1 mL triethylamine at 70° C. for 14 hours to give (Z)-1,3-dihydro-5-(2-pyridinyl)ethynyl-3-[(1H-pyrrol-2-yl)methylene]-2H-indol-2-one as a red powder. (Yield 42 mg, 80%).

Example 96

Synthesis of (Z)-1,3-Dihydro-5-(4-hydroxyphenyl) ethynyl-3-[(3-methoxy-1H-pyrrol-2-yl)-methylene]-2H-indol-2-one (GGGG)

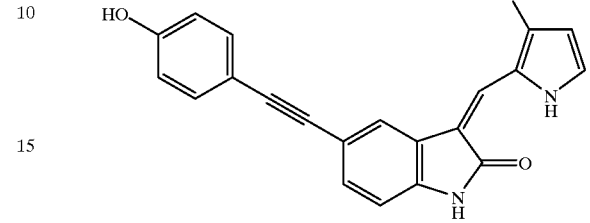

This compound was also prepared in a manner analogous to the preparation of (Z)-1,3-dihydro-5-(4-hydroxyphenyl) ethynyl-3-[(1H-pyrrol-2-yl)methylene]-2H-indol-2-one in Example 83 above. In this example, (Z)-1,3-dihydro-5-ethynyl-3-[(3-methoxy-1H-pyrrol-2-yl)methylene]-2H-indol-2-one (75 mg, 0.28 mmol) (from Example 93) was coupled with 4-iodophenol (75 mg, 0.34 mmol) (Aldrich) using CuI (8 mg, 0.042 mmol) (Aldrich) and $(Ph_3P)_2PdCl_2$ (14 mg, 0.020 mmol) (Aldrich) as catalyst in 1 mL DMF and 1 mL triethylamine at 70° C. for 14 hours to give (Z)-1,3-dihydro-5-(4-hydroxyphenyl) ethynyl-3-[(3-methoxy-1H-pyrrol-2-yl)-methylene]-2H-indol-2-one as a yellow powder. (Yield 62 mg, 62%).

Example 97

Synthesis of (Z)-1,3-Dihydro-5-(4-methoxyphenyl) ethynyl-3-[(1H-pyrrol-2-yl)-methylene]-2H-indol-2-one (HHHH)

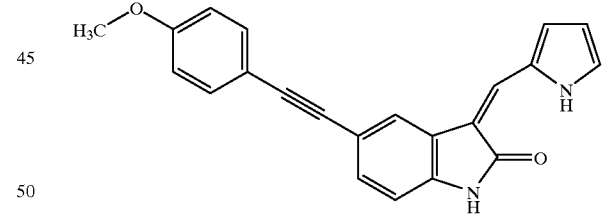

This compound was also prepared in a manner analogous to the preparation of (Z)-1,3-dihydro-5-(4-hydroxyphenyl) ethynyl-3-[(1H-pyrrol-2-yl)methylene]-2H-indol-2-one in Example 83 above. In this example, (Z)-1,3-dihydro-5-ethynyl-3-[(1H-pyrrol-2-yl)methylene]-2H-indol-2-one (60 mg, 0.26 mmol) (Example 82) was coupled with 4-iodoanisole (30 mg, 0.34 mmol) (Aldrich) using CuI (6 mg, 0.031 mmol) (Aldrich) and $(Ph_3P)_2PdCl_2$ (14 mg, 0.020 mmol) (Aldrich) as catalyst in 1 mL DMF and 2 mL triethylamine at 70° C. for 16 hours to give (Z)-1,3-dihydro-5-(4-methoxyphenyl)ethynyl-3-[(1H-pyrrol-2-yl)-methylene]-2H-indol-2-one as a yellow powder. (Yield 63 mg, 71%).

Example 98

Synthesis of (Z)-1,3-Dihydro-3-[(1H-pyrrol-2-yl)-methylene]-5-(2-thiophenyl)ethynyl-2H-indol-2-one (IIII)

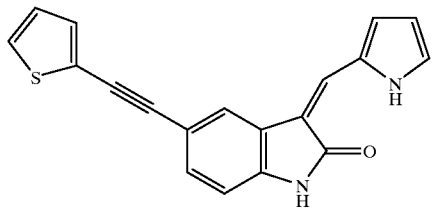

This compound was also prepared in a manner analogous to the preparation of (Z)-1,3-dihydro-5-(4-hydroxyphenyl)ethynyl-3-[(1H-pyrrol-2-yl)methylene]-2H-indol-2-one in Example 83 above. In this example, (Z)-1,3-dihydro-5-ethynyl-3-[(1H-pyrrol-2-yl)methylene]-2H-indol-2-one (42 mg, 0.18 mmol) (from Example 82) was coupled with 2-bromothiophene (30 mg, 0.18 mmol) (Aldrich) using CuI (8 mg, 0.042 mmol) (Aldrich) and (Ph$_3$P)$_2$PdCl$_2$ (14 mg, 0.020 mmol) (Aldrich) as catalyst in 1 mL DMF and 1 mL triethylamine at 70° C. for 14 hours to give (Z)-1,3-dihydro-3-[(1H-pyrrol-2-yl)-methylene]-5-(2-thiophenyl)ethynyl-2H-indol-2-one as a yellow powder. (Yield 25 mg, 44%).

Example 99

Synthesis of (Z)-5-Bromo-1,3-dihydro-3-[(4-methyl-1H-imidazol-5-yl)methylene]-2H-indol-2-one (JJJJ)

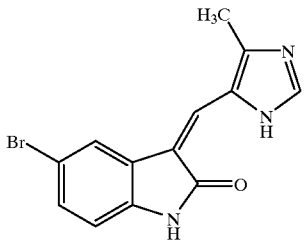

A mixture of 5-bromo-1,3-dihydro-2H-indol-2-one (0.3 g, 1.41 mmol) (Starting Material 6), and excess 4-methyl-5-imidazolecarboxaldehyde (0.25 g, 2.27 mmol) (Aldrich) in 1% piperidine in 2-propanol (6 mL) was heated at 90° C. for 4 h. Hot water (6 mL) was added. On cooling, the crystallized product was filtered off, washed with aqueous 2-propanol and dried. (Yield 0.44 g, 100%)

Example 100

Synthesis of (Z)-1,3-Dihydro-3-[(4-methyl-1H-imidazol-5-yl)methylene]-5-(trimethylsilyl)ethynyl-2H-indol-2-one (KKKK)

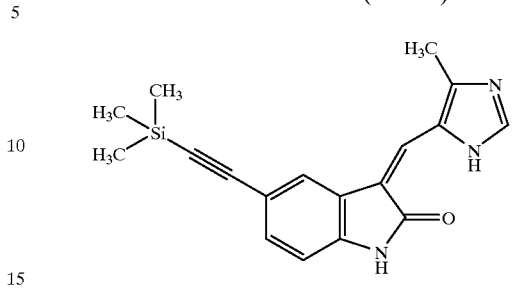

(Z)-5-Bromo-1,3-dihydro-3-[(4-methyl-1H-imidazol-5-yl)methylene]-2H-indol-2-one (0.17 g, 0.56 mmol) (from Example 99) was dissolved in 3 mL DMF and 3 mL triethylamine. The solution was degassed for 30 minutes by bubbling argon through the solution. At this time (trimethylsilyl)acetylene (0.3 mL, 2.1 mmol) (Aldrich), CuI (34 mg) (Aldrich) and (Ph$_3$P)$_2$PdCl$_2$ (34 mg) (Aldrich) were added and the reaction flask sealed. The reaction was heated, under argon, at 90° C. for 18 hours. After cooling, the mixture was filtered through Celite® (Fisher Scientific) and residue washed extensively with hot EtOAc and CH$_3$CN. Combined filtrate and washing was concentrated under reduced pressure and the product was purified via flash column chromatography (SiO$_2$, 230–400 mesh) with 5% MeOH in CH$_2$Cl$_2$. (Yield 0.1 g, 56%).

Example 101

Synthesis of (Z)-1,3-Dihydro-5-ethynyl-3-[(4-methyl-1H-imidazol-5-yl)methylene]-2H-indol-2-one, trifluoroacetate salt (LLLL)

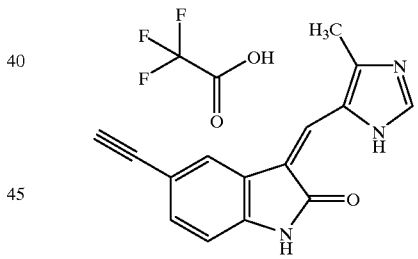

To a solution of (Z)-1,3-dihydro-3-[(4-methyl-1H-imidazol-5-yl)methylene]-5-(trimethylsilyl)ethynyl-2H-indol-2-one (0.1 g, 0.31 mmol) (from Example 100) in 8 mL ethanol was added dropwise a solution of silver nitrate (0.12 g, 0.68 mmol) in 1.5 mL water and 0.5 mL ethanol during which time a precipitate formed. The mixture was stirred at room temperature for 1 h, after which a solution of potassium cyanide (0.22 g, 3.37 mmol) in 1 mL of water was added and the precipitated dissolved. After stirring for an additional 20 min, 30 mL of water was added and the mixture extracted with EtOAc (3×30 mL). The product was purified by reverse phase HPLC using water/acetonitrile/trifluoroacetic acid as solvent. (Yield 20 mg, 18%).

Example 102

SAPK Inhibitory Activity

The SAPK inhibitory activity of the compounds of the invention is demonstrated below. These effects indicate that the compounds of the present invention are useful in treating inflammatory diseases such as, for example, rheumatoid arthritis.

SAPK FlashPlate Assay

Human JNK is highly homologous to rat SAPK. To measure the inhibitory activity of test compounds, the compounds were tested in the rat SAPK assay.

For the SAPK assay, purified GST-cJun (a chimeric protein containing cjun, a natural substrate of JNK) was coated on 96 well FlashPlates (New England Nuclear, Boston, Mass.). Purified rat SAPK (isoform β, Kyriakis et al. supra) was preincubated with preparations containing MEKK-1 and MKK4 for 30 minutes at 37° C. in assay buffer containing 25 mM HEPES, pH 7.5, 150 mM NaCl, 20 mM MgCl$_2$, 2 mM DTT, 0.001% Tween 20, 1 μM ATP freshly added. In the preincubation step, MEKK-1 phosphorylates and activates MKK-4, which in turn phosphorylates and activates SAPK. The activated SAPK was then added to the cJun coated FlashPlates along with $^{33}$P-ATP (0.32 μCi per reaction) and test compounds. The plates were incubated for 30 minutes at 37° C., then washed with PBS, 0.01% Tween 20, and counted in the Topcount scintillation counter (Packard Instrument Co., Downers Grove, Ill.). Dilutions of compounds were tested in duplicate in each assay. The percent inhibition of cJun phosphorylation (a measure of inhibition of SAPK activity) was determined by the following formula:

$$100 \times \left[ 1 - \frac{\text{test compound} - \text{nonspecific}}{\text{total} - \text{nonspecific}} \right]$$

where "test compound" refers to the average counts per minute of the test duplicates, "nonspecific" refers to the average counts per minute when no SAPK was added, and "total" refers to the average counts per minute when no compound was added.

The results of the SAPK assay with various test compounds is summarized below in Table I A and I B.

Table I A

| Compound | IC$_{50}$ (pM) SAPK |
|---|---|
| D | <1.0 |
| G | <1.0 |
| H | <1.0 |
| M | <1.0 |
| N | <1.0 |
| Q | <1.0 |
| R | <1.0 |
| T | 0.253<1.0 |
| V | 0.034<1.0 |
| Y | <1.0 |
| BB | <1.0 |
| DD | <1.0 |
| EE | <1.0 |
| QQQ | <1.0 |
| FF | <1.0 |
| HH | <1.0 |
| MM | <1.0 |
| NN | <1.0 |
| OO | <1.0 |
| PP | <1.0 |
| RR | <1.0 |
| SS | <1.0 |
| TT | <1.0 |
| UU | <1.0 |
| VV | <1.0 |
| XX | <1.0 |
| YY | <1.0 |

Table I A-continued

| Compound | IC$_{50}$ (pM) SAPK |
|---|---|
| BBB | <1.0 |
| CCC | <1.0 |
| DDD | <1.0 |
| EEE | <1.0 |
| FFF | <1.0 |
| GGG | <1.0 |
| HHH | <1.0 |

TABLE I B

| | SAPK | |
|---|---|---|
| Compound | % Inhibition | Concentration (μM) |
| O | >50 | <1.0 |
| AA | >50 | <1.0 |
| III | <50 | <0.10 |

MG-63 Cell-Based Assay

The MG63 cell line, a human osteosarcoma cell line, was purchased from American Type Culture Collection (ATCC; Rockville, Md.) and grown in the medium recommended by ATCC. When stimulated with human IL-1β, MG63 cells release matrix metalloproteinase 3 (MMP-3), an AP-1 dependent inflammatory mediator and IL-6, a NF-κB-dependent mediator. In this assay the ability of a test compound to block MMP-3 expression and not block IL-6 expression is an indication that the compound is a selective inhibitor of the AP-1 transcription pathway.

On day 1 the cells were plated at 2.5×10$^4$ cells/well in 96 well plates. After 24 hours, dexamethasone (the assay control) (Sigma, St. Louis, Mo.) and the test compounds were diluted to appropriate concentrations and added to the MG63 cells. The cells were incubated with the compounds for 24 hours after which the supernatants were removed and analyzed by ELISA.

In the ELISA, 96 well plates were coated with antibody to MMP-3 or IL-6. Supernatants were added to the coated plates and any antigen (MMP-3 or IL-6) in the supernatant bound to the antibody coated on the plates. The plates were then washed with PBS containing 0.05% Tween 20 (Sigma, St. Louis, Mo.) and the biotinylated secondary antibody was added. This secondary antibody binds to the already bound antigen creating a "sandwich effect". Plates were washed as described above and horseradish peroxidase (HRP)-streptavidin conjugate (Sigma, St. Louis, Mo.) was added to the plates. HRP-streptavidin bound to the biotin-antibody conjugate. The plates were washed and TMB substrate (Kirkegaard and Perry Labs, Gaithersburg, Md.) was added to the wells. This substrate changes color in the presence of HRP-streptavidin. The intensity of the color (measured at 450 nm) is proportional to the amount of MMP-3 or IL-6 produced by the MG63 cells upon exposure to IL-1β and the test compounds. Optical density values were converted to concentration (pg/ml or Units/ml) based on a standard curve included in the assay. IC$_{50}$ values for each test compound were determined from the linear regression of a plot of the logarithm of the concentration of compound versus amount of MMP-3 or IL-6 secreted. (The MMP-3 antibodies were prepared in-house using standard hybridoma technology and the IL-6 antibodies were obtained from either Genzyme, Cambridge, Mass. or Pharmingen, San Diego, Calif.).

The results of this assay on various test compounds is summarized below in Table II.

TABLE II

| Compound | IC$_{50}$ ($\mu$M) in MG63 Cells | |
|---|---|---|
| | MMP3 | IL6 |
| D | <12.5 | 20.0 |
| G | <12.5 | <20 |
| H | <12.5 | <20 |
| N | <12.5 | <20 |
| O | <12.5 | <20 |
| P | <12.5 | <20 |
| R | <12.5 | <20 |
| Y | <12.5 | <20 |
| Z | <12.5 | <20 |
| BB | <12.5 | <20 |
| CC | <12.5 | <20 |
| EE | <12.5 | <20 |
| QQQ | <12.5 | 20.0 |
| GG | <12.5 | <20 |
| FFF | <12.5 | <20 |
| III | <12.5 | 20.0 |

U937 Cell-Based Assay

The U937 cells, a human monocyte/macrophage cell line, was obtained from the ATTC and grown in the recommended medium. These cells when stimulated with lipopolysaccharide (LPS) release TNF, another inflammatory mediator implicated in the JNK pathway (Swantek et al., supra) and IL-6. In this assay the ability of a test compound to block TNF expression is evaluated.

The assay is very similar to the MG63 cell based assay except for the following modifications. The U937 cells were suspension cells but when stimulated with phorbol myristate acetate (PMA) (Sigma, St. Louis, Mo.) they become adherent. After PMA stimulation the cells were washed in cell culture medium and plated at 1×10$^5$ cells/well in 96 well plates. The following day the test compounds and dexamethasone control (Sigma, St. Louis, Mo.) were added to the cells for 1 hour of preincubation. Then the cells were stimulated with LPS (Sigma, St. Louis, Mo.). After an additional 24 hours of incubation the supernatants were removed and assayed for TNF-α and IL-6 by ELISA. The IL-6 ELISA was run as described previously for the MG63 assay. The TNF ELISA was run using a kit supplied by Genzyme (Cambridge, Mass.).

The results of this assay with various test compounds is summarized below in Table III.

TABLE III

| Compound | IC$_{50}$ ($\mu$M) in U937 Cells | |
|---|---|---|
| | TNF | IL6 |
| N | <8 | <20 |
| O | <8 | <20 |
| R | <8 | 20.0 |
| BB | <8 | <20 |

Example 103

Tablet Formulation

| Item | Ingredients | mg/Tablet | | | | | |
|---|---|---|---|---|---|---|---|
| 1 | Compound 1* | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total weight | 120 | 120 | 150 | 300 | 600 | 900 |

*Compound 1 represents a compound of the invention.

Manufacturing Procedure:

Mix Items 1, 2 and 3 in a suitable mixer for 15 minutes.
Granulate the powder mix from Step 1 with 20% Povidone K30 Solution (Item 4).
Dry the granulation from Step 2 at 50° C.
Pass the granulation from Step 3 through a suitable milling equipment.
Add the Item 5 to the milled granulation Step 4 and mix for 3 minutes.
Compress the granulation from Step 5 on a suitable press.

Example 104

Capsule Formulation

| Item | Ingredients | mg/capsule | | | | |
|---|---|---|---|---|---|---|
| 1 | Compound 1* | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

*Compound 1 represents a compound of the invention.

Manufacturing Procedure:
1. Mix Items 1, 2 and 3 in a suitable mixer for 15 minutes.
2. Add Items 4 & 5 and mix for 3 minutes.
3. Fill into a suitable capsule.

Example 105

Injection Solution/Emulsion Preparation

| Item | Ingredient | mg/mL |
|---|---|---|
| 1 | Compound 1* | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water q.s. | 1 mL |

*Compound 1 represents a compound of the invention.

Manufacturing Procedure:
1. Dissolve item 1 in item 2
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 um filter and fill into vials.

Example 106

Injection Solution/Emulsion Preparation

| Item | Ingredient | mg/mL |
|------|------------|-------|
| 1 | Compound 1* | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

*Compound 1 represents a compound of the invention.

Manufacturing Procedure:
1. Dissolve item 1 in item 2
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 um filter and fill into vials.

While the invention has been illustrated by reference to specific and preferred embodiments, those skilled in the art will understand that variations and modifications may be made through routine experimentation and practice of the invention. Thus, the invention is intended not to be limited by the foregoing description, but to be defined by the appended claims and their equivalents.

What is claimed is:
1. A compound having the formula

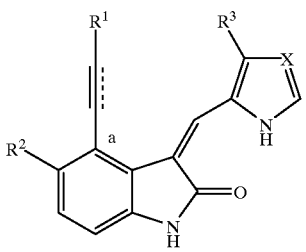

I or prodrugs or of compounds of formula I, or the pharmaceutically acceptable salts of all of the foregoing compounds, wherein:

$R^1$ is selected from the group consisting of
lower alkyl that is substituted by the group consisting of aryl, aryloxy, heteroaryl, heteroaryloxy, substituted aryl, substituted aryloxy, substituted heteroaryl, substituted heteroaryloxy, lower alkyl that is substituted by the group consisting of aryl, aryloxy, heteroaryl, heteroaryloxy, substituted aryl, substituted aryloxy, substituted heteroaryl, and substituted heteroaryloxy, and also by the group consisting of $R^{13}$, perfluoroalkyl, cycloalkyl which is unsubstituted or substituted by the group consisting of lower alkyl and $R^{13}$, and heterocycle which is unsubstituted or substituted by the group consisting of lower alkyl and $R^{13}$,
and wherein the substitutents on the substituted aryl, substituted aryloxy, substituted heteroaryl, and substituted heteroaryloxy are selected from the group consisting of
$R^{13}$,
lower alkyl which is unsubstituted or substituted by $R^{13}$,
cycloalkyl which is unsubstituted or substituted by $R^{13}$, and
heterocycle which is unsubstituted or substituted by $R^{13}$;
aryl which is unsubstituted or substituted by the group consisting of
$R^{13}$,
perfluoroalkyl,
lower alkyl which is unsubstituted or substituted by $R^{13}$,
cycloalkyl which is unsubstituted or substituted by $R^{13}$, and
heterocycle which is unsubstituted or substituted by $R^{13}$; and
heteroaryl which is unsubstituted or substituted by the group consisting of
$R^{13}$,
perfluoroalkyl,
lower alkyl which is unsubstituted or substituted by $R^{13}$,
cycloalkyl which is unsubstituted or substituted by $R^{13}$, and
heterocycle which is unsubstituted or substituted by $R^{13}$;
$R^2$ is selected from the group consisting of
—H,
—$OR^4$,
—$OCOR^4$,
—$COR^4$,
—$COOR^4$,
—$CONR^6R^7$,
—$NR^6R^7$,
halogen,
—$NO_2$,
—CN,
—$SO_2R^4$,
—$SO_2NR^6R^7$,
—perfluoroalkyl, and
—lower alkyl which is unsubstituted or substituted by —$OR^8$ or —$NR^6R^7$;
$R^3$ is selected from the group consisting of
—H,
—$OR^4$,
—$COR^4$,
—$COOR^4$,
—$CONR^6R^7$,
halogen,
—CN
—$NR^6R^7$,
—perfluoroalkyl, and
lower alkyl which is unsubstituted or substituted by —$OR^8$ or —$NR^6R^7$;
$R^4$ is selected from the group consisting of
—H,
lower alkyl which is unsubstituted or substituted by the group consisting of —$OR^5$, —$COOR^8$, —$COR^8$, —$CONR^8R^9$, —$NR^6R^7$, cycloalkyl, heterocycle, —CN, —$NO_2$, —$SO_2R^8$, and —$SO_2NR^8R^9$,
cycloalkyl which is unsubstituted or substituted by the group consisting of —$OR^5$, —$COOR^8$, —$COR^8$, —$CONR^8R^9$, —$NR^6R^7$, lower alkyl, heterocycle, —CN, —$NO_2$, —$SO_2R^8$, and —$SO_2NR^8R^9$,
heterocycle which is unsubstituted or substituted by the group consisting of —$OR^5$, —$COOR^8$, —$COR^8$, —$CONR^8R^9$, —$NR^6R^7$, lower alkyl, cycloalkyl, —CN, —$NO_2$, —$SO_2R^8$, and —$SO_2NR^8R^9$,
aryl which is unsubstituted or substituted by the group consisting of —$OR^5$, —$COOR^8$, —$COR^8$, —CONR$^8$R$^9$, —NR$^6$R$^7$, cycloalkyl, heterocycle, —CN, —NO$_2$, —SO$_2$R$^8$, —SO$_2$NR$^8$R$^9$, and halogen,
heteroaryl which is unsubstituted or substituted by the group consisting of —OR$^5$, —COOR$^8$, —COR$^8$, —CONR$^8$R$^9$, —NR$^6$R$^7$, cycloalkyl, heterocycle, —CN, —NO$_2$, —SO$_2$R$^8$—SO$_2$NR$^8$R$^9$, and halogen;

R$^5$ is selected from the group consisting of
—H,
—COR$^8$,
—CONR$^8$R$^9$, and
—lower alkyl which is unsubstituted or substituted by the group consisting of —OR$^9$, —NR$^9$R$^{10}$, —N(COR$^9$)R$^{10}$, —COR$^9$, —CONR$^9$R$^{10}$, —SR$^9$ and —COOR$^9$;

R$^6$ and R$^7$ are each independently selected from the group consisting of
—H,
—COR$^8$,
—COOR$^8$,
—CONR$^8$R$^9$,
—SO$_2$R$^8$,
—SO$_2$NR$^8$R$^9$,
lower alkyl which is unsubstituted or substituted by the group consisting of —OR$^5$, —NR$^8$R$^9$, —COOR$^8$, —COR$^8$, —CONR$^8$R$^9$, —CN, —NO$_2$, —SO$_2$R$^8$, —SO$_2$NR$^8$R$^9$,
cycloalkyl which is unsubstituted or substituted by the group consisting of —OR$^5$, —COOR$^8$, —COR$^8$, —CONR$^8$R$^9$, —NR$^8$R$^9$, lower alkyl, heterocycle, —CN, —NO$_2$, —SO$_2$R$^8$, and —SO$_2$NR$^8$R$^9$,
heterocycle which is unsubstituted or substituted by the group consisting of —OR$^5$, —COOR$^8$, —COR$^8$, —CONR$^8$R$^9$, —NR$^8$R$^9$, lower alkyl, cycloalkyl, —CN, —NO$_2$, —SO$_2$R$^8$, and —SO$_2$NR$^8$R$^9$,
aryl which is unsubstituted or substituted by the group consisting of —OR$^5$, —COOR$^8$, —COR$^8$, —CONR$^8$R$^9$, —NR$^8$R$^9$, lower alkyl, cycloalkyl, heterocycle, —CN, —NO$_2$, —SO$_2$R$^8$, and —SO$_2$NR$^8$R$^9$, and
heteroaryl which is unsubstituted or substituted by the group consisting of —OR$^5$, —COOR$^8$, —COR$^8$, —CONR$^8$R$^9$, —NR$^8$R$^9$, lower alkyl, cycloalkyl, heterocycle, —CN, —NO$_2$, —SO$_2$R$^8$, and —SO$_2$NR$^8$R$^9$,
cycloalkyl which is unsubstituted or substituted by the group consisting of —OR$^5$, —COOR$^8$, —COR$^8$, —CONR$^8$R$^9$, —NR$^8$R$^9$, lower alkyl, heterocycle, —CN, —NO$_2$, —SO$_2$R$^8$, and —SO$_2$NR$^8$R$^9$,
heterocycle which is unsubstituted or substituted by the group consisting of —OR$^5$, —COOR$^8$, —COR$^8$, —CONR$^8$R$^9$, —NR$^8$R$^9$, lower alkyl, cycloalkyl, —CN, —NO$_2$, —SO$_2$R$^8$, and —SO$_2$NR$^8$R$^9$,
aryl which is unsubstituted or substituted by the group consisting of —OR$^5$, —COOR$^8$, —COR$^8$, —CONR$^8$R$^9$, —NR$^8$R$^9$, lower alkyl, cycloalkyl, heterocycle, —CN, —NO$_2$, —SO$_2$R$^8$, and —SO$_2$NR$^8$R$^9$,
heteroaryl which is unsubstituted or substituted by the group consisting of —OR$^5$, —COOR$^8$, —COR$^8$, —CONR$^8$R$^9$, —NR$^8$R$^9$, lower alkyl, cycloalkyl, heterocycle, —CN, —NO$_2$, —SO$_2$R$^8$, and —SO$_2$NR$^8$R$^9$, and
—NR$^6$R$^7$ can form a ring having 3 to 7 atoms, said ring not including any additional hetero atoms or including one or more additional hetero atoms and being unsubstituted or substituted by the group consisting of lower alkyl, —OR$^5$, —COR$^8$, —COOR$^8$, —CONR$^8$R$^9$, and —NR$^5$R$^9$;

R$^8$ is selected from the group consisting of
—H,
lower alkyl which is unsubstituted or substituted by the group consisting of cycloalkyl, heterocycle, aryl, heteroaryl, —OR$^9$, —NR$^9$R$^{10}$, and —N(COR$^9$)R$^{10}$,
aryl which is unsubstituted or substituted by the group consisting of —OR$^9$, —COOR$^9$, —COR$^9$, —CONR$^{10}$R$^9$, —NR$^{10}$R$^9$, lower alkyl, cycloalkyl, heterocycle, —CN, —NO$_2$, —SO$_2$R$^9$, and —SO$_2$NR$^{10}$R$^9$,
heteroaryl which is unsubstituted or substituted by the group consisting of —OR$^9$, —COOR$^9$, —COR$^9$, —CONR$^{10}$R$^9$, —NR$^{10}$R$^9$, lower alkyl, cycloalkyl, heterocycle, —CN, —NO$_2$, —SO$_2$R$^9$, and —SO$_2$NR$^{10}$R$^9$,
cycloalkyl which is unsubstituted or substituted by the group consisting of —OR$^9$, —COOR$^9$, —COR$^9$, —CONR$^{10}$R$^9$, —NR$^{10}$R$^9$, lower alkyl, heterocycle, —CN, —NO$_2$, —SO$_2$R$^9$, and —SO$_2$NR$^{10}$R$^9$,
heterocycle which is unsubstituted or substituted by the group consisting of —OR$^9$, —COOR$^9$, —COR$^9$, —CONR$^{10}$R$^9$, —NR$^{10}$R$^9$, lower alkyl, cycloalkyl, —CN, —NO$_2$, —SO$_2$R$^9$, and —SO$_2$NR$^{10}$R$^9$;

R$^9$ and R$^{10}$ are each independently selected from the group consisting of
—H and lower alkyl;

R$^{13}$ is selected from the group consisting of
halogen,
—OCOR$^4$,
—COR$^4$,
—COOR$^4$,
—CONR$^6$R$^7$,
—NO$_2$,
—NR$^6$R$^7$
—CN,
—SO$_2$R$^4$, and
—SO$_2$NR$^6$R$^7$;

X is selected from the group consisting of
—N— and —C—; and a is or is not a bond.

2. A compound having the formula

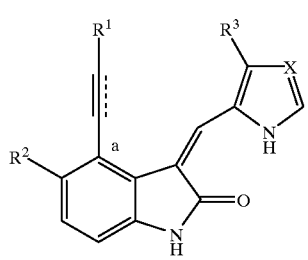

I or the pharmaceutically acceptable salts of the foregoing compounds, wherein:
R$^1$ is selected from the group consisting of
lower alkyl that is substituted by the group consisting of aryl, aryloxy, heteroaryl, heteroaryloxy, substituted aryl, substituted aryloxy, substituted heteroaryl, and substituted heteroaryloxy, lower alkyl that is substituted by the group consisting of aryl, aryloxy, heteroaryl, heteroaryloxy, substituted aryl, substituted aryloxy, substituted heteroaryl, and substituted heteroaryloxy and also substituted by the group consisting of $R^{13}$, perfluoroalkyl, cycloalkyl which is unsubstituted or substituted by the group consisting of lower alkyl and $R^{13}$, and heterocycle which is unsubstituted or substituted by the group consisting of lower alkyl and $R^{13}$, and wherein the substitutents on the substituted aryl, substituted aryloxy, substituted heteroaryl, and substituted heteroaryloxy are selected from the group consisting of
$R^{13}$,
lower alkyl which is unsubstituted or substituted by $R^{13}$,
cycloalkyl which is unsubstituted or substituted by $R^{13}$, and
heterocycle which is unsubstituted or substituted by $R^{13}$;

aryl which is unsubstituted or may be substituted by the group consisting of
$R^{13}$,
perfluoroalkyl,
lower alkyl which is unsubstituted or substituted by $R^{13}$,
cycloalkyl which is unsubstituted or substituted by $R^{13}$, and
heterocycle which is unsubstituted or substituted by $R^{13}$; and heteroaryl which optionally may be substituted by the group consisting of
$R^{13}$,
perfluoroalkyl,
lower alkyl which is unsubstituted or substituted by $R^{13}$,
cycloalkyl which is unsubstituted or substituted by $R^{13}$, and
heterocycle which is unsubstituted or substituted by $R^{13}$;

$R^2$ is selected from the group consisting of
—H,
—$OR^4$,
—$OCOR^4$,
—$COR^4$,
—$COOR^4$,
—$CONR^6R^7$,
—$NR^6R^7$,
halogen,
—$NO_2$,
—CN,
—$SO_2R^4$,
—$SO_2NR^6R^7$,
—perfluoroalkyl, and
—lower alkyl which is unsubstituted or substituted by —$OR^8$ or —$NR^6R^7$;

$R^3$ is selected from the group consisting of
—H,
—$OR^4$,
—$COR^4$,
—$COOR^4$,
—$CONR^6R^7$,
halogen,
—CN
—$NR^6R^7$,
—perfluoroalkyl, and
lower alkyl which is unsubstituted or substituted by —$OR^8$ or —$NR^6R^7$;

$R^4$ is selected from the group consisting of
—H, lower alkyl which is unsubstituted or substituted by the group consisting of —$OR^5$, —$COOR^8$, —$COR^8$, —$CONR^8R^9$, —$NR^6R^7$, cycloalkyl, heterocycle, —CN, —$NO_2$, —$SO_2R^8$, and —$SO_2NR^8R^9$, cycloalkyl which is unsubstituted or substituted by the group consisting of —$OR^5$, —$COOR^8$, —$COR^8$, —$CONR^8R^9$, —$NR^6R^7$, lower alkyl, heterocycle, —CN, —$NO_2$, —$SO_2R^8$, and —$SO_2NR^8R^9$, heterocycle which is unsubstituted or substituted by the group consisting of —$OR^5$, —$COOR^8$, —$COR^8$, —$CONR^8R^9$, —$NR^6R^7$, lower alkyl, cycloalkyl, —CN, —$NO_2$, —$SO_2R^8$, and —$SO_2NR^8R^9$, aryl which is unsubstituted or substituted by the group consisting of —$OR^5$, —$COOR^8$, —$COR^8$, —$CONR^8R^9$, —$NR^6R^7$, cycloalkyl, heterocycle, —CN, —$NO_2$, —$SO_2R^8$, —$SO_2NR^8R^9$, and halogen, heteroaryl which is unsubstituted or substituted by the group consisting of —$OR^5$, —$COOR^8$, —$COR^8$, —$CONR^8R^9$, —$NR^6R^7$, cycloalkyl, heterocycle, —CN, —$NO_2$, —$SO_2R^8$, —$SO_2NR^8R^9$, and halogen;

$R^5$ is selected from the group consisting of
—H,
—$COR^8$,
—$CONR^8R^9$, and
—lower alkyl which is unsubstituted or substituted by the group consisting of —$OR^9$, —$NR^9R^{10}$, —$N(COR^9)R^{10}$, —$COR^9$, —$CONR^9R^{10}$, —$SR^9$ and —$COOR^9$;

$R^6$ and $R^7$ are each independently selected from the group consisting of
—H,
—$COR^8$,
—$COOR^8$,
—$CONR^8R^9$,
—$SO_2R^8$,
—$SO_2NR^8R^9$, lower alkyl which is unsubstituted or substituted by the group consisting of —$OR^5$, —$NR^8R^9$, —$COOR^8$, —$COR^8$, —$CONR^8R^9$, —CN, —$NO_2$, —$SO_2R^8$, —$SO_2NR^8R^9$, cycloalkyl which is unsubstituted or substituted by the group consisting of —$OR^5$, —$COOR^8$, —$COR^8$, —$CONR^8R^9$, —$NR^8R^9$, lower alkyl, heterocycle, —CN, —$NO_2$, —$SO_2R^8$, and —$SO_2NR^8R^9$, heterocycle which is unsubstituted or substituted by the group consisting of —$OR^5$—$COOR^8$, —$COR^8$, —$CONR^8R^9$, —$NR^8R^9$, lower alkyl, cycloalkyl, —CN, —$NO_2$, —$SO_2R^8$, and —$SO_2NR^8R^9$, aryl which is unsubstituted or substituted by the group consisting of —$OR^5$, —$COOR^8$, —$COR^8$, —$CONR^8R^9$, —$NR^8R^9$, lower alkyl, cycloalkyl, heterocycle, —CN, —$NO_2$, —$SO_2R^8$, and —$SO_2NR^8R^9$, and heteroaryl which is unsubstituted or substituted by the group consisting of —$OR^5$, —$COOR^8$, —$COR^8$, —$CONR^8R^9$, —$NR^8R^9$, lower alkyl, cycloalkyl, heterocycle, —CN, —$NO_2$, —$SO_2R^8$, and —$SO_2NR^8R^9$, cycloalkyl which is unsubstituted or substituted by the group consisting of —$OR^5$, —$COOR^8$, —$COR^8$, —$CONR^8R^9$, —$NR^8R^9$, lower alkyl, heterocycle, —CN, —$NO_2$, —$SO_2R^8$, and —$SO_2NR^8R^9$, heterocycle which is unsubstituted or substituted by the group consisting of —$OR^5$, —$COOR^8$, —$COR^8$, —$CONR^8R^9$, —$NR^8R^9$, lower alkyl, cycloalkyl, —CN, —$NO_2$, —$SO_2R^8$, and —$SO_2NR^8R^9$, aryl which is unsubstituted or substituted by the group consisting of —OR$^5$, —COOR$^8$, —COR$^8$, —CONR$^8$R$^9$, —NR$^8$R$^9$, lower alkyl, cycloalkyl, heterocycle, —CN, —NO$_2$, —SO$_2$R$^8$, and —SO$_2$NR$^8$R$^9$, heteroaryl which is unsubstituted or substituted by the group consisting of —OR$^5$, —COOR$^8$, —COR$^8$, —CONR$^8$R$^9$, —NR$^8$R$^9$, lower alkyl, cycloalkyl, heterocycle, —CN, —NO$_2$, —SO$_2$R$^8$, and/or, —NR$^6$R$^7$ can y form a ring having 3 to 7 atoms, said ring not including any additional hetero atoms or including one or more additional hetero atoms and being unsubstituted or substituted by the group consisting of lower alkyl, —OR$^5$, —COR$^8$, —COOR$^8$, —CONR$^8$R$^9$, and —NR$^5$R$^9$;

R$^8$ is selected from the group consisting of
—H,
lower alkyl which is unsubstituted or substituted by the group consisting of cycloalkyl, heterocycle, aryl, heteroaryl, —OR$^9$, —NR$^9$R$^{10}$, and —N(COR$^9$)R$^{10}$,
aryl which is unsubstituted or substituted by the group consisting of —OR$^9$, —COOR$^9$, —COR$^9$, —CONR$^{10}$R$^9$, —NR$^{10}$R$^9$, lower alkyl, cycloalkyl, heterocycle, —CN, —NO$_2$, —SO$_2$R$^9$, and —SO$_2$NR$^{10}$R$^9$, and
heteroaryl which is unsubstituted or substituted by the group consisting of —OR$^9$, —COOR$^9$, —COR$^9$, —CONR$^{10}$R$^9$, —NR$^{10}$R$^9$, lower alkyl, cycloalkyl, heterocycle, —CN, —NO$_2$, —SO$_2$R$^9$, and —SO$_2$NR$^{10}$R$^9$;
cycloalkyl which is unsubstituted or substituted by the group consisting of —OR$^9$, —COOR$^9$, —COR$^9$, —CONR$^{10}$R$^9$, —NR$^{10}$R$^9$, lower alkyl, heterocycle, —CN, —NO$_2$, —SO$_2$R$^9$, and —SO$_2$NR$^{10}$R$^9$;
heterocycle which is unsubstituted or substituted by the group consisting of —OR$^9$, —COOR$^9$, —COR$^9$, —CONR$^{10}$R$^9$, —NR$^{10}$R$^9$, lower alkyl, cycloalkyl, —CN, —NO$_2$, —SO$_2$R$^9$, and —SO$_2$NR$^{10}$R$^9$;

R$^9$ and R$^{10}$ are each independently selected from the group consisting of
—H and lower alkyl;

R$^{13}$ is selected from the group consisting of
halogen,
—OR$^4$,
—OCOR$^4$,
—COR$^4$
—COOR$^4$,
—CONR$^6$R$^7$,
—NO$_2$,
—NR$^6$R$^7$,
—CN,
—SO$_2$R$^4$, and
—SO$_2$NR$^6$R$^7$;

X is selected from the group consisting of
—N— and —C—; and a is or is not a bond.

3. The compound of claim 2 wherein R$^1$ is selected from the group consisting of lower alkyl that is substituted by the group consisting of aryl and substituted aryl, and lower alkyl that is substituted by the group consisting of aryl and substituted aryl and also substituted by the group consisting of halogen, —OR$^4$, —COR$^4$, —COOR$^4$, —CONR$^6$R$^7$, cycloalkyl, heterocycle, —COOR$^4$, CONR$^6$R$^7$, cycloalkyl which is substituted by the group consisting of OR$^5$ and —NR$^6$R$^7$, COOR$^4$, CONR$^6$R$^7$, and heterocycle which is substituted by the group consisting of —OR$^5$ and —NR$^6$R$^7$, —COOR$^4$, —CONR$^6$R$^7$; and wherein the substituents on the substituted aryl are selected from the group consisting of halogen, —OR$^4$, —COR$^4$, —COOR$^4$, —CONR$^6$R$^7$, —NO$_2$, —NR$^6$R$^7$, —SO$_2$R$^4$, —SO$_2$NR$^6$R$^7$, —CN, perfluoroalkyl, lower alkyl, cycloalkyl, heterocycle, lower alkyl which is substituted by the group consisting of —OR$^5$ and —NR$^6$R$^7$, —COOR$^4$, —CONR$^6$R$^7$, cycloalkyl which is substituted by the group consisting of —OR$^5$ and —NR$^6$R$^7$, —COOR$^4$, —CONR$^6$R$^7$, and heterocycle which is substituted by the group consisting of —OR$^5$ and —NR$^6$R$^7$, —COOR$^4$, and —CONR$^6$R$^7$;

lower alkyl that is substituted by the group consisting of heteroaryl and substituted heteroaryl, and lower alkyl that is substituted by the group consisting of heteroaryl and substituted heteroaryl and is also substituted by the group consisting of halogen, —OR$^4$, —COR$^4$, —COOR$^4$, —CONR$^6$R$^7$, cycloalkyl, heterocycle, cycloalkyl which is substituted by the group consisting of OR$^5$, COOR$^4$, CONR$^6$R$^7$, and —NR$^6$R$^7$, and heterocycle which is substituted by the group consisting of —OR$^5$, COOR$^4$, CONR$^6$R$^7$, and —NR$^6$R$^7$; and wherein the substituents on the substituted heteroaryl are selected from the group consisting of halogen, —OR$^4$, —COR$^4$, —COOR$^4$, NR$^6$R$^7$, —SO$_2$R$^4$, —SO$_2$NR$^6$R$^7$, —NO$_2$, —CN, —CONR$^6$R$^7$, lower alkyl, cycloalkyl, heterocycle, lower alkyl which is substituted by the group consisting of —OR$^5$ and —NR$^6$R$^7$, —COOR$^4$, —CONR$^6$R$^7$, cycloalkyl which is substituted by the group consisting of —OR$^5$ and —NR$^6$R$^7$, —COOR$^4$, —CONR$^6$R$^7$, and heterocycle which is substituted by the group consisting of —OR$^5$ —NR$^6$R$^7$, —COOR$^4$, and —CONR$^6$R$^7$;

aryl which is unsubstituted or substituted by the group consisting of halogen, —OR$^4$, —COR$^4$, —COOR$^4$, —CONR$^6$R$^7$, lower alkyl, cycloalkyl, heterocycle, lower alkyl which is substituted by the group consisting of —OR$^5$, —NR$^6$R$^7$, —COOR$^4$, and —CONR$^6$R$^7$, cycloalkyl which is substituted by the group consisting of —OR$^5$, —COOR$^4$, —CONR$^6$R$^7$, and —NR$^6$R$^7$, and heterocycle which is substituted by the group consisting of —OR$^5$, —COOR$^4$, —CONR$^6$R$^7$, and —NR$^6$R$^7$; and heteroaryl which is unsubstituted or substituted by the group consisting of halogen, —OR$^4$, —COR$^4$, —COOR$^4$, —CONR$^6$R$^7$, lower alkyl, cycloalkyl, heterocycle, lower alkyl which is substituted by the group consisting of —OR$^5$, —COOR$^4$, —CONR$^6$R$^7$, and —NR$^6$R$^7$, cycloalkyl which is substituted by the group consisting of —OR$^5$, —COOR$^4$, —CONR$^6$R$^7$, and —NR$^6$R$^7$, and heterocycle which is substituted by the group consisting of —OR$^5$, —COOR$^4$, —CONR$^6$R$^7$, and —NR$^6$R$^7$.

4. The compound of claim 2 wherein R$^1$ is

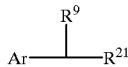

wherein Ar is aryl which is unsubstituted or substituted by one or more substituent independently selected from the group consisting of
—H,
—OR$^4$, —COR⁴,
—COOR⁴,
—CONR⁶R⁷,
halogen,
—CN
—NR⁶R⁷, and
lower alkyl which is unsubstituted or substituted by —OR⁴, —COOR⁴, —CONR⁶R⁷, or —NR⁶R⁷;

R⁹ is selected from the group consisting of
—H and lower alkyl; and

R²¹ is selected from the group consisting of
—OR⁴, and
—NR⁶R⁷.

5. The compound of claim 2 wherein R¹ is

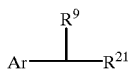

wherein Ar is heteroaryl which is unsubstituted or substituted by one or more substituents independently selected from the group consisting of
—H,
—OR⁴,
—COR⁴,
—COOR⁴,
—CONR⁶R⁷,
halogen,
—CN,
—NR⁶R⁷, and
lower alkyl which is unsubstituted or substituted by —OR⁴, —COOR⁴, —CONR⁶R⁷, or —NR⁶R⁷.

6. The compound of claim 2 wherein R¹ is Ar'
wherein Ar' is selected from the group consisting of aryl and heteroaryl, each of which independently is unsubstituted or substituted by the group consisting of
—H,
—OR⁴,
—COR⁴,
—COOR⁴,
—CONR⁶R⁷,
halogen,
—CN
—NR⁶R⁷, and
lower alkyl which is unsubstituted or substituted by —OR⁴ or —NR⁶R⁷.

7. The compound of claim 2 wherein, R² is selected from the group consisting of
—H,
—OR⁴,
—COOR⁴,
—CONR⁶R⁷,
—NR⁶R⁷,
halogen,
—NO₂, and
—CN.

8. The compound of claim 2 wherein R³ is selected from the group consisting of
—H,
—OR⁴,
—NR⁶R⁷, and
lower alkyl which is unsubstituted or substituted by the group consisting of —OR⁸ and —NR⁶R⁷.

9. The compound of claim 7 wherein R³ is selected from the group consisting of
—H,
—OR⁴,
—NR⁶R⁷, and
lower alkyl which is unsubstituted or substituted by the group consisting of —OR⁸ and —NR⁶R⁷.

10. The compound of claim 2 wherein R⁴ is selected from the group consisting of
—H,
lower alkyl which is unsubstituted or substituted by one or more —OR⁵, —COOR⁸, —COR⁸ and —CONR⁸R⁹,
cycloalkyl which is unsubstituted or substituted by one or more —OR⁵, —COOR⁸, —COR⁸ and —CONR⁸R⁹, and
heterocycle which is unsubstituted or substituted by one or more —OR⁵, —COOR⁸, —COR⁸ and —CONR⁸R⁹.

11. The compound of claim 9 wherein R⁴ is selected from the group consisting of
—H,
lower alkyl which is unsubstituted or substituted by one or more —OR⁵, —COOR⁸, —COR⁸ and —CONR⁸R⁹,
cycloalkyl which is unsubstituted or substituted by one or more —OR⁵, —COOR⁸, —COR⁸ and —CONR⁸R⁹, and
heterocycle which is unsubstituted or substituted by one or more —OR⁵, —COOR⁸, —COR⁸ and —CONR⁸R⁹.

12. The compound of claim 2 wherein R⁵ is selected from the group consisting of
—H,
—COR⁸,
—CONR⁸R⁹, and
lower alkyl.

13. The compound of claim 11 wherein R⁵ is selected from the group consisting of
—H,
—COR⁸,
—CONR⁸R⁹, and
lower alkyl.

14. The compound of claim 2 wherein R⁶ and R⁷ are each independently selected from the group consisting of
—H,
—COR⁸,
—COOR⁸,
—CONR⁸R⁹,
lower alkyl which is unsubstituted or substituted by the group consisting of —OR⁹ and —NR⁸R⁹, —COOR⁸, —CONR⁸R⁹, and
—NR⁶R⁷ can form a ring having 3 to 7 atoms, said ring not including any additional hetero atoms or including one or more additional hetero atoms and being unsubstituted or substituted by the group consisting of lower alkyl, —OR⁵, —COR⁸, —COOR⁸, —CONR⁸R⁹, and —NR⁵R⁹.

15. The compound of claim 13 wherein R⁶ and R⁷ are each independently selected from the group consisting of
—H,
—COR⁸,
—COOR⁸,
—CONR⁸R⁹,
lower alkyl which is unsubstituted or substituted by the group consisting of —OR⁹ and —NR⁸R⁹, COOR⁸, CONR⁸R⁹, and —NR$^6$R$^7$ can form a ring having 3 to 7 atoms, said ring not including any additional hetero atoms or including one or more additional hetero atoms and being unsubstituted or substituted by the group consisting of lower alkyl, —OR$^5$, —COR$^8$, —COOR$^8$, —CONR$^8$R$^9$, and —NR$^5$R$^9$.

16. The compound of claim 2 wherein R$^8$ is selected from the group consisting of
    —H and lower alkyl which is unsubstituted or substituted by the group consisting of aryl, heteroaryl, —OR$^9$, —COOR$^9$, —CONR$^9$R$^{10}$, and —NR$^9$R$^{10}$.

17. The compound of claim 15 wherein R$^8$ is selected from the group consisting of
    —H and lower alkyl which is unsubstituted or substituted by the group consisting of aryl, heteroaryl, —OR$^9$, —COOR$^9$, —CONR$^9$R$^{10}$, and —NR$^9$R$^{10}$.

18. The compound of claim 2 wherein "a" is a bond.
19. The compound of claim 17 wherein "a" is a bond.
20. A compound having the formula:

II and the pharmaceutically acceptable salts of the foregoing compounds, wherein:
R$^3$ is selected from the group consisting of
    —H,
    —OR$^4$,
    —COR$^4$,
    —COOR$^4$,
    —CONR$^6$R$^7$,
    halogen,
    —CN
    —NR$^6$R$^7$,
    —perfluoroalkyl, and
    lower alkyl which is unsubstituted or substituted by —OR$^8$ or —NR$^6$R$^7$;
R$^4$ is selected from the group consisting of
    —H,
    lower alkyl which is unsubstituted or substituted by the group consisting of —OR$^5$, —COOR$^8$, —COR$^8$, —CONR$^8$R$^9$, —NR$^6$R$^7$, cycloalkyl, heterocycle, —CN, —NO$_2$, —SO$_2$R$^8$, and —SO$_2$NR$^8$R$^9$,
    cycloalkyl which is unsubstituted or substituted by the group consisting of —OR$^5$, —COOR$^8$, —COR$^8$, —CONR$^8$R$^9$, —NR$^6$R$^7$, lower alkyl, heterocycle, —CN, —NO$_2$, —SO$_2$R$^8$, and —SO$_2$NR$^8$R$^9$,
    heterocycle which is unsubstituted or substituted by the group consisting of —OR$^5$, —COOR$^8$, —COR$^8$, —CONR$^8$R$^9$, —NR$^6$R$^7$, lower alkyl, cycloalkyl, —CN, —NO$_2$, —SO$_2$R$^8$, and —SO$_2$NR$^8$R$^9$,
    aryl which is unsubstituted or substituted by the group consisting of —OR$^5$, —COOR$^8$, —COR$^8$, —CONR$^8$R$^9$, —NR$^6$R$^7$, cycloalkyl, heterocycle, —CN, —NO$_2$, —SO$_2$R$^8$, —SO$_2$NR$^8$R$^9$, and halogen,
    heteroaryl which is unsubstituted or substituted by the group consisting of —OR$^5$, —COOR$^8$, —COR$^8$, —CONR$^8$R$^9$, —NR$^6$R$^7$, cycloalkyl, heterocycle, —CN, —NO$_2$, —SO$_2$R$^8$, —SO$_2$NR$^8$R$^9$, and halogen;

R$^5$ is selected from the group consisting of
    —H,
    —COR$^8$,
    —CONR$^8$R$^9$, and
    —lower alkyl which is unsubstituted or substituted by the group consisting of —OR$^9$, —NR$^9$R$^{10}$, —N(COR$^9$)R$^{10}$, —COR$^9$, —CONR$^9$R$^{10}$, —SR$^9$ and —COOR$^9$;

R$^6$ and R$^7$ are each independently selected from the group consisting of
    —H,
    —COR$^8$,
    —COOR$^8$,
    —CONR$^8$R$^9$,
    —SO$_2$R$^8$,
    —SO$_2$NR$^8$R$^9$,
    lower alkyl which is unsubstituted or substituted by the group consisting of —OR$^5$, —NR$^8$R$^9$, —COOR$^8$, —COR$^8$, —CONR$^8$R$^9$, —CN, —NO$_2$, —SO$_2$R$^8$, —SO$_2$NR$^8$R$^9$,
    cycloalkyl which is unsubstituted or substituted by the group consisting of —OR$^5$, —COOR$^8$, —COR$^8$, —CONR$^8$R$^9$, —NR$^8$R$^9$, lower alkyl, heterocycle, —CN, —NO$_2$, —SO$_2$R$^8$, and —SO$_2$NR$^8$R$^9$,
    heterocycle which is unsubstituted or substituted by the group consisting of —OR$^6$, —COOR$^8$, —COR$^8$, —CONR$^8$R$^9$, —NR$^8$R$^9$, lower alkyl, cycloalkyl, —CN, —NO$_2$, —SO$_2$R$^8$, and —SO$_2$NR$^8$R$^9$,
    aryl which is unsubstituted or substituted by the group consisting of —OR$^5$, —COOR$^8$, —COR$^8$, —CONR$^8$R$^9$, —NR$^8$R$^9$, lower alkyl, cycloalkyl, heterocycle, —CN, —NO$_2$, —SO$_2$R$^8$, and —SO$_2$NR$^8$R$^9$, and
    heteroaryl which is unsubstituted or substituted by the group consisting of —OR$^5$, —COOR$^8$, —COR$^8$, —CONR$^8$R$^9$, —NR$^8$R$^9$, lower alkyl, cycloalkyl, heterocycle, —CN, —NO$_2$, —SO$_2$R$^8$, and —SO$_2$NR$^8$R$^9$,
    cycloalkyl which is unsubstituted or substituted by the group consisting of —OR$^5$, —COOR$^8$, —COR$^8$, —CONR$^8$R$^9$, —NR$^8$R$^9$, lower alkyl, heterocycle, —CN, —NO$_2$, —SO$_2$R$^8$, and —SO$_2$NR$^8$R$^9$,
    heterocycle which is unsubstituted or substituted by the group consisting of —OR$^5$, —COOR$^8$, —COR$^8$, —CONR$^8$R$^9$, —NR$^8$R$^9$, lower alkyl, cycloalkyl, —CN, —NO$_2$, —SO$_2$R$^8$, and —SO$_2$NR$^8$R$^9$,
    aryl which is unsubstituted or substituted by the group consisting of —OR$^5$, —COOR$^8$, —COR$^8$, —CONR$^8$R$^9$, —NR$^8$R$^9$, lower alkyl, cycloalkyl, heterocycle, —CN, —NO$_2$, —SO$_2$R$^8$, and —SO$_2$NR$^8$R$^9$,
    heteroaryl which is unsubstituted or substituted by the group consisting of —OR$^5$, —COOR$^8$, —COR$^8$, —CONR$^8$R$^9$, —NR$^8$R$^9$, lower alkyl, cycloalkyl, heterocycle, —CN, —NO$_2$, —SO$_2$R$^8$, and —SO$_2$NR$^8$R$^9$, and
    —NR$^6$R$^7$ can form a ring having 3 to 7 atoms, said ring not including any additional hetero atoms or including one or more additional hetero atoms and being unsubstituted or substituted by the group consisting of lower alkyl, —OR$^5$, —COR$^8$, —COOR$^8$, —CONR$^8$R$^9$, and —NR$^5$R$^9$;

R$^8$ is selected from the group consisting of
    —H,
    lower alkyl which is unsubstituted or substituted by the group consisting of cycloalkyl, heterocycle, aryl, heteroaryl, —OR$^9$, —NR$^9$R$^{10}$, and —N(COR$^9$)R$^{10}$, aryl which is unsubstituted or substituted by the group consisting of —OR$^9$, —COOR$^9$, —COR$^9$, —CONR$^{10}$R$^9$, —NR$^{10}$R$^9$, lower alkyl, cycloalkyl, heterocycle, —CN, —NO$_2$, —SO$_2$R$^9$, and —SO$_2$NR$^{10}$R$^9$, and heteroaryl which is unsubstituted or substituted by the group consisting of —OR$^9$, —COOR$^9$, —COR$^9$, —CONR$^{10}$R$^9$, —NR$^{10}$R$^9$, lower alkyl, cycloalkyl, heterocycle, —CN, —NO$_2$, —SO$_2$R$^9$, and —SO$_2$NR$^{10}$R$^9$;

cycloalkyl which is unsubstituted or substituted by the group consisting of —OR$^9$, —COOR$^9$, —COR$^9$, —CONR$^{10}$R$^9$, —NR$^{10}$R$^9$, lower alkyl, heterocycle, —CN, —NO$_2$, —SO$_2$R$^9$, and —SO$_2$NR$^{10}$R$^9$;

heterocycle which is unsubstituted or substituted by the group consisting of —OR$^9$, —COOR$^9$, —COR$^9$, —CONR$^{10}$R$^9$, —NR$^{10}$R$^9$, lower alkyl, cycloalkyl, —CN, —NO$_2$, —SO$_2$R$^9$, and —SO$_2$NR$^{10}$R$^9$;

R$^9$ and R$^{10}$ are each independently selected from the group consisting of
—H and lower alkyl;

R$^{11}$ is selected from the group consisting of
—H,
—COR$^4$,
—COOR$^4$,
—CONR$^6$R$^7$,
lower alkyl which is unsubstituted or substituted by the group consisting of —OR$^5$, —NR$^6$R$^7$, halogen, —NO$_2$, —SO$_2$R$^4$, —SO$_2$NR$^6$R$^7$, —CN, —COR$^4$, —COOR$^4$, —CONR$^6$R$^7$, cycloalkyl, heterocycle, aryl, and heteroaryl,
cycloalkyl, which is unsubstituted or substituted by the group consisting of —OR$^5$, —NR$^6$R$^7$, halogen, —NO$_2$, —SO$_2$R$^4$, —SO$_2$NR$^6$R$^7$, —CN, —COR$^4$, —COOR$^4$, —CONR$^6$R$^7$, lower alkyl, heterocycle, aryl, and heteroaryl,
heterocycle, which is unsubstituted or substituted by the group consisting of —OR$^5$, —NR$^6$R$^7$, halogen, —NO$_2$, —SO$_2$R$^4$, —SO$_2$NR$^6$R$^7$, —CN, —COR$^4$, —COOR$^4$, —CONR$^6$R$^7$, lower alkyl, cycloalkyl, aryl, and heteroaryl,
aryl, which is unsubstituted or substituted by the group consisting of —OR$^5$, —NR$^6$R$^7$, halogen, —NO$_2$, —SO$_2$R$^4$, —SO$_2$NR$^6$R$^7$, —CN, —COR$^4$, —COOR$^4$, —CONR$^6$R$^7$, lower alkyl, and perfluoroalkyl, and
heteroaryl, which is unsubstituted or substituted by the group consisting of —OR$^5$, —NR$^6$R$^7$, halogen, —NO$_2$, —SO$_2$R$^4$, —SO$_2$NR$^6$R$^7$, —CN, —COR$^4$, —COOR$^4$, —CONR$^6$R$^7$, lower alkyl, and perfluoroalkyl; and R$^{12}$ is selected from the group consisting of
—H,
—OR$^4$,
—OCOR$^4$,
—COR$^4$,
—COOR$^4$,
—CONR$^6$R$^7$,
—NR$^6$R$^7$,
—halogen,
—NO$_2$,
—CN,
—SO$_2$R$^4$,
—SO$_2$NR$^6$R$^7$,
—perfluoroalkyl,
lower alkyl which is unsubstituted or substituted from the group consisting of —OR$^4$, —NR$^6$R$^7$, cycloalkyl, heterocycle, —COR$^4$, —COOR$^4$, —CONR$^6$R$^7$, —CN, —NO$_2$, —SO$_2$R$^4$, —SO$_2$NR$^6$R$^7$ and halogen, cycloalkyl which is unsubstituted or substituted from the group consisting of —OR$^4$, —NR$^6$R$^7$, lower alkyl, heterocycle, —COR$^4$, —COOR$^4$, —CONR$^6$R$^7$, —CN, —NO$_2$, —SO$_2$R$^4$, —SO$_2$NR$^6$R$^7$ and halogen, and heterocycle which is unsubstituted or substituted from the group consisting of —OR$^4$, —NR$^6$R$^7$, lower alkyl, cycloalkyl, —COR$^4$, —COOR$^4$, —CONR$^6$R$^7$, —CN, —NO$_2$, —SO$_2$R$^4$, —SO$_2$NR$^6$R$^7$ and halogen;

X is selected from the group consisting of
—N— and —C—; and a is an optional bond.

21. The compound of claim 20 wherein R$^3$ is selected from the group consisting of
—H,
—OR$^4$,
—NR$^6$R$^7$, and
lower alkyl which is unsubstituted or substituted by the group consisting of —OR$^8$ and —NR$^6$R$^7$.

22. The compound of claim 20 wherein R$^4$ is selected from the group consisting of
—H,
lower alkyl which is unsubstituted or substituted by one or more —OR$^5$, —COOR$^8$, —COR$^8$ and —CONR$^8$R$^9$,
cycloalkyl which is unsubstituted or substituted by one or more —OR$^5$, —COOR$^8$, —COR$^8$ and —CONR$^8$R$^9$, and
heterocycle which is unsubstituted or substituted by one or more —OR$^5$, —COOR$^8$, —COR$^8$ and —CONR$^8$R$^9$.

23. The compound of claim 21 wherein R$^4$ is selected from the group consisting of
—H,
lower alkyl which is unsubstituted or substituted by one or more —OR$^5$, —COOR$^8$, —COR$^8$ and —CONR$^8$R$^9$,
cycloalkyl which is unsubstituted or substituted by one or more —OR$^5$, —COOR$^8$, —COR$^8$ and —CONR$^8$R$^9$, and
heterocycle which is unsubstituted or substituted by one or more —OR$^5$, —COOR$^8$, —COR$^8$ and —CONR$^8$R$^9$.

24. The compound of claim 20 wherein R$^5$ is selected from the group consisting of
—H,
—COR$^8$,
—CONR$^8$R$^9$, and
lower alkyl.

25. The compound of claim 23 wherein R$^5$ is selected from the group consisting of
—H,
—COR$^8$,
—CONR$^8$R$^9$, and
lower alkyl.

26. The compound of claim 20 wherein R$^6$ and R$^7$ are each independently selected from the group consisting of
—H,
—COR$^8$,
—COOR$^8$,
—CONR$^8$R$^9$,
lower alkyl which is unsubstituted or substituted by the group consisting of —OR$^9$ and —NR$^8$R$^9$, COOR$^8$, CONR$^8$R$^9$, and —NR⁶R⁷ can form a ring having 3 to 7 atoms, said ring not including any additional hetero atoms or including one or more additional hetero atoms and being unsubstituted or substituted by the group consisting of lower alkyl, —OR⁵, —COR⁸, —COOR⁸, —CONR⁸R⁹, and —NR⁵R⁹.

27. The compound of claim 25 wherein R⁶ and R⁷ are each independently selected from the group consisting of
—H,
—COR⁸,
—COOR⁸,
—CONR⁸R⁹,
lower alkyl which is unsubstituted or substituted by the group consisting of —OR⁵ and —NR⁸R⁹, —COOR⁸, —CONR⁸R⁹, and
—NR⁶R⁷ can form a ring having 3 to 7 atoms, said ring not including any additional hetero atoms or including one or more additional hetero atoms and being optionally substituted by the group consisting of lower alkyl, —OR⁵, COR⁸ COOR⁸, —CONR⁸R⁹, and —NR⁵R⁹.

28. The compound of claim 20 wherein R⁸ is selected from the group consisting of
—H and lower alkyl which is unsubstituted or substituted by the group consisting of aryl, heteroaryl, —OR⁹, —COOR⁹, —CONR⁹R¹⁰, and —NR⁹R¹⁰.

29. The compound of claim 27 wherein R⁸ is selected from the group consisting of
—H and lower alkyl which is unsubstituted or substituted by the group consisting of aryl, heteroaryl, —OR⁹, —COOR⁹, —CONR⁹R¹⁰, and —NR⁹R¹⁰.

30. The compound of claim 20 wherein R¹¹ is aryl which is unsubstituted or substituted by the group consisting of —OR⁵ and —NR⁶R⁷.

31. The compound of claim 29 wherein R¹¹ is aryl which is unsubstituted or substituted by the group consisting of —OR⁵ and —NR⁶R⁷.

32. The compound of claim 20 wherein R¹¹ is selected from the group consisting of
—H,
—COR⁴,
—COOR⁴,
—CONR⁶R⁷,
lower alkyl which is unsubstituted or substituted from the group consisting of —OR⁴, —NR⁶R⁷, cycloalkyl, heterocycle, —COR⁴, —COOR⁴, —CONR⁶R⁷, —CN, —NO₂, —SO₂R⁴, —SO₂NR⁶R⁷ and halogen,
cycloalkyl which is unsubstituted or substituted from the group consisting of —OR⁴, —NR⁶R⁷, lower alkyl, heterocycle, —COR⁴, —COOR⁴, —CONR⁶R⁷, —CN, —NO₂, —SO₂R⁴, —SO₂NR⁶R⁷ and halogen, and
heterocycle which is unsubstituted or substituted from the group consisting of —OR⁴, —NR⁶R⁷, lower alkyl, cycloalkyl, —COR⁴, —COOR⁴, —CONR⁶R⁷, —CN, —NO₂, —SO₂R⁴, —SO₂NR⁶R⁷ and halogen.

33. The compound of claim 20 wherein wherein "a" is a bond.

34. The compound of claim 32 wherein "a" is a bond.

35. A compound selected from the group consisting of
1,3-Dihydro-5-fluoro-4-iodo-2H-indol-2-one,
(Z)-1,3-Dihydro-3-[(1H-pyrrol-2-yl)methylene]-5-(trimethylsilyl)ethynyl-2H-indol-2-one,
(Z)-5-Bromo-1,3-dihydro-3-[(3-methoxy-1H-pyrrol-2-yl)methylene]-2H-indol-2-one,
(Z)-1,3-Dihydro-3-[(3-methoxy-1H-pyrrol-2-yl)methylene]-5-(trimethylsilyl)ethynyl-2H-indol-2-one, (Z)-5-Bromo-1,3-dihydro-3-[(4-methyl-1H-imidazol-5-yl)methylene]-2H-indol-2-one,
(Z)-1,3-Dihydro-3-[(4-methyl-1H-imidazol-5-yl)methylene]-5-(trimethylsilyl)ethynyl-2H-indol-2-one.

36. A compound selected from the group consisting of
(Z)-1,3-Dihydro-4-(phenylethynyl)-3-[(3-methoxy-1H-pyrrol-2-yl)methylene]-2H-indol-2-one (D),
(Z)-1,3-Dihydro-4-[(4-methoxyphenyl)ethynyl]-3-[(3-methoxy-1H-pyrrol-2-yl)methylene]-2H-indol-2-one (G).

37. A compound selected from the group consisting of
rac-(Z)-1,3-Dihydro-4-[3-hydroxy-3-(4-methoxyphenyl)-1-propynyl]-3-[(3-methoxy-1H-pyrrol-2-yl)methylene]-2H-indol-2-one (H),
rac-(Z)-1,3-Dihydro-4-[3-hydroxy-3-(3-hydroxyphenyl)-1-propynyl]-3-[(3-methoxy-1H-pyrrol-2-yl)methylene]-2H-indol-2-one (I),
rac-(Z)-1,3-Dihydro-4-[3-hydroxy-3-(3-methoxyphenyl)-1-propynyl]-3-[(3-methoxy-1H-pyrrol-2-yl)methylene]-2H-indol-2-one (J),
rac-(Z)-4-[3-[2,3-Dihydro-3-[(3-methoxy-1H-pyrrol-2-yl) methylene]-2-oxo-1H-indol-4-yl]-1-hydroxy-2-propynyl]benzoic acid methyl ester (K),
rac-(Z)-4-[3-[2,3-Dihydro-3-[(3-methoxy-1H-pyrrol-2-yl)methylene]-2-oxo-1H-indol-4-yl]-1-hydroxy-2-propynyl]benzoic acid (L),
rac-(Z)-1,3-Dihydro-4-[3-hydroxy-3-(2-methoxyphenyl)-1-propynyl]-3-[(3-methoxy-1H-pyrrol-2-yl)methylene]-2H-indol-2-one (M),
rac-(Z)-4-[3-(1,3-benzodioxol-5-yl)-3-hydroxy-1-propynyl]-1,3-dihydro-3-[(3-methoxy-1H-pyrrol-2-yl)methylene]-2H-indol-2-one (N),
rac-(Z)-1,3-Dihydro-4-[3-hydroxy-3-(4-hydroxy-3-methoxyphenyl)-1-propynyl]-3-[(3-methoxy-1H-pyrrol-2-yl)methylene]-2H-indol-2-one (O),
rac-(Z)-1,3-Dihydro-4-[3-hydroxy-3-(4-hydroxyphenyl)-1-propynyl]-3-[(3-methoxy-1H-pyrrol-2-yl)methylene]-2H-indol-2-one (Q),
rac-(Z)-1,3-Dihydro-4-[3-(4-dimethylaminophenyl)-3-hydroxy-1-propynyl]-3-[(3-methoxy-1H-pyrrol-2-yl)methylene]-2H-indol-2-one (R),
rac-(Z)-1,3-Dihydro-4-[3-hydroxy-3-(4-phenoxyphenyl)-1-propynyl]-3-[(3-methoxy-1H-pyrrol-2-yl)methylene]-2H-indol-2-one (S),
rac-(Z)-1,3-Dihydro-4-[3-hydroxy-3-phenyl-1-butynyl]-3-[(3-methoxy-1H-pyrrol-2-yl)methylene]-2H-indol-2-one (T),
rac-(Z)-1,3-Dihydro-4-[3-[4-(3-dimethylaminopropoxy)-phenyl]-3-hydroxy-1-propynyl]-3-[(3-methoxy-1H-pyrrol-2-yl)methylene]-2H-indol-2-one (V),
rac-(Z)-1,3-Dihydro-4-[3-(2,3-dimethoxyphenyl)-3-hydroxy-1-propynyl]-3-[(3-methoxy-1H-pyrrol-2-yl)methylene]-2H-indol-2-one (EE),
rac-(Z)-1,3-Dihydro-4-[3-(3,4-dimethoxyphenyl)-3-hydroxy-1-propynyl]-3-[(3-methoxy-1H-pyrrol-2-yl)methylene]-2H-indol-2-one (FF),
rac-(Z)-1,3-Dihydro-4-[3-hydroxy-3-(3-hydroxy-4-methoxyphenyl)-1-propynyl]-3-[(3-methoxy-1H-pyrrol-2-yl)methylene]-2H-indol-2-one (HH),
rac-(Z)-1,3-Dihydro-4-[3-hydroxy-3-[3-methoxy-4-[2-(4-morpholinyl)-ethoxy]-phenyl]-1-propynyl]-3-[(3-methoxy-1H-pyrrol-2-yl)methylene]-2H-indol-2-one (MM), rac-(Z)-1,3-Dihydro-4-[3-hydroxy-3-[3-methoxy-4-[2-(4-morpholinyl)-ethoxy]-phenyl]-1-propynyl]-3-[(3-methoxy-1H-pyrrol-2-yl)methylene]-2H-indol-2-one hydrochloride salt (NN), rac-(Z)-1,3-Dihydro-4-[3-hydroxy-3-(2,4,5-trimethoxyphenyl)-1-propynyl]-3-[(3-methoxy-1H-pyrrol-2-yl)methylene]-2H-indol-2-one (PP), rac-(Z)-[4-[3-[2,3-Dihydro-3-[(3-methoxy-1H-pyrrol-2-yl)methylene]-2-oxo-1H-indol-4-yl]-1-hydroxy-2-propynyl]-2-methoxyphenoxy]acetic acid methyl ester (QQ), rac-(Z)-[4-[3-[2,3-Dihydro-3-[(3-methoxy-1H-pyrrol-2-yl)methylene]-2-oxo-1H-indol-4-yl]-1-hydroxy-2-propynyl]-2-methoxyphenoxy]acetic acid (RR), rac-(Z)-4-[3-hydroxy-3-(4-methoxy-1,3-benzodioxol-6-yl)-1-propynyl]-1,3-dihydro-3-[(3-methoxy-1H-pyrrol-2-yl)methylene]-2H-indol-2-one (SS), rac-(Z)-1,3-Dihydro-4-[3-hydroxy-3-[4-[2-(4-morpholinyl)-ethoxy]-phenyl]-1-propynyl]-3-[(3-methoxy-1H-pyrrol-2-yl)methylene]-2H-indol-2-one (TT), rac-(Z)-4-[3-(4-Chloro-2-methylsulfanylmethoxyphenyl)-3-hydroxy-1-propynyl]-1,3-dihydro-3-[(3-methoxy-1H-pyrrol-2-yl)methylene]-2H-indol-2-one (UU), rac-(Z)-4-[3-(3-Chlorophenyl)-3-hydroxy-1-propynyl]-1,3-dihydro-3-[(3-methoxy-1H-pyrrol-2-yl)methylene]-2H-indol-2-one (WW), rac-(Z)-[4-[3-[2,3-dihydro-3-[(3-methoxy-1H-pyrrol-2-yl)methylene]-2-oxo-1H-indol-4-yl]-1-hydroxy-2-propynyl]phenoxy]acetic acid 1,1-dimethylethyl ester (XX), rac-(Z)-[4-[3-[2,3-dihydro-3-[(3-methoxy-1H-pyrrol-2-yl)methylene]-2-oxo-1H-indol-4-yl]-1-hydroxy-2-propynyl]phenoxy]acetic acid (YY), rac-(Z)-1,3-Dihydro-4-[3-hydroxy-3-(3-nitrophenyl)-1-propynyl]-3-[(3-methoxy-1H-pyrrol-2-yl)methylene]-2H-indol-2-one (ZZ), rac-(Z)-4-[3-(3-Aminophenyl)-3-hydroxy-1-propynyl]-1,3-dihydro-3-[(3-methoxy-1H-pyrrol-2-yl)methylene]-2H-indol-2-one (AA), rac-(Z)-4-[3-(4-Acetamidophenyl)-3-hydroxy-1-propynyl]-1,3-dihydro-3-[(3-methoxy-1H-pyrrol-2-yl)methylene]-2H-indol-2-one (BBB), rac-(Z)-1,3-Dihydro-4-(3-hydroxy-3-phenyl-1-propynyl)-3-[(3-methoxy-1H-pyrrol-2-yl)methylene]-2H-indol-2-one (FFF).

38. A compound selected from the group consisting of rac-(Z)-1,3-Dihydro-4-[3-hydroxy-3-(3-pyridinyl)-1-propynyl]-3-[(3-methoxy-1H-pyrrol-2-yl)methylene]-2H-indol-2-one (X), Synthesis of rac-(Z)-1,3-Dihydro-4-[3-hydroxy-3-(1-methyl-pyrrol-2-yl)-1-propynyl]-3-[(3-methoxy-1H-pyrrol-2-yl)methylene]-2H-indol-2-one (AA), rac-(Z)-1,3-Dihydro-4-[3-hydroxy-3-(thiophen-3-yl)-1-propynyl]-3-[(3-methoxy-1H-pyrrol-2-yl)methylene]-2H-indol-2-one (BB), rac-(Z)-1,3-Dihydro-4-[3-hydroxy-3-(1H-pyrrol-2-yl)-1-propynyl]-3-[(3-methoxy-1H-pyrrol-2-yl)methylene]-2H-indol-2-one (DD), rac-(Z)-1,3-Dihydro-4-[3-hydroxy-3-(2-pyridinyl)-1-propynyl]-3-[(3-methoxy-1H-pyrrol-2-yl)methylene]-2H-indol-2-one (JJ), rac-(Z)-1,3-Dihydro-4-[3-hydroxy-3-(2-thiophenyl)-1-propynyl]-3-[(3-methoxy-1H-pyrrol-2-yl)methylene]-2H-indol-2-one (KK), rac-(Z)-1,3-Dihydro-4-[3-hydroxy-3-(3-methoxy-2-thiophenyl)-1-propynyl]-3-[(3-methoxy-1H-pyrrol-2-yl)methylene]-2H-indol-2-one (OO), rac-(Z)-1,3-Dihydro-4-[3-(2-furanyl)-3-hydroxy-1-propynyl]-3-[(3-methoxy-1H-pyrrol-2-yl)methylene]-2H-indol-2-one (VV).

39. The compound
(Z)-1,3-Dihydro-3-[(3-methoxy-1H-pyrrol-2-yl)methylene]-4-(3-phenoxy-1-propynyl)-2H-indol-2-one (Y).

40. A compound selected from the group consisting of (Z)-1,3-Dihydro-3-[(3-methoxy-1H-pyrrol-2-yl)methylene]-4-[(3-pyridinyl)ethynyl]-2H-indol-2-one (CCC), (Z)-1,3-Dihydro-3-[(3-methoxy-1H-pyrrol-2-yl)methylene]-4-[(2-pyridinyl)ethynyl]-2H-indol-2-one (DDD), (Z)-1,3-Dihydro-3-[(3-methoxy-1H-pyrrol-2-yl)methylene]-4-[(4-pyridinyl)ethynyl]-2H-indol-2-one (EEE), (Z)-1,3-Dihydro-3-[(3-methoxy-1H-pyrrol-2-yl)methylene]-5-nitro-4-[(3-pyridinyl)ethynyl]-2H-indol-2-one (GGG), (Z)-5-Amino-1,3-dihydro-3-[(3-methoxy-1H-pyrrol-2-yl)methylene]-4-[(3-pyridinyl)ethynyl]-2H-indol-2-one (HHH), and (Z)-N-[2,3-Dihydro-3-[(3-methoxy-1H-pyrrol-2-yl)methylene]-2-oxo-4-[(3-pyridinyl)ethynyl]-1H-indol-5-yl]-2-thiopheneacetamide (III).

41. A compound selected from the group consisting of

4-[(E)-2-(2-Chlorophenyl)-ethenyl]-1,3-dihydro-(Z)-3-[(1H-pyrrol-2-yl)methylene]-2H-indol-2-one (KKK), 1,3-Dihydro-(Z)-3-[(1H-pyrrol-2yl)methylene]-[(E)-2-phenylethenyl]-2H-indol-2-one (LLL), 1,3-Dihydro-(Z)-3-[(3-methoxy-1H-pyrrol-2yl)methylene]-[(E)-2-phenylethenyl]-2H-indol-2-one (MMM), 1,3-Dihydro-4-[(E)-2-(4-methoxyphenyl)-ethenyl]-(Z)-3-[(1H-pyrrol-2-yl)methlene]-2H-indol-2-one (NNN), 1,3-Dihydro-(Z)-3-[(3-methoxy-1H-pyrrol-2-yl)methylene]-4-[(E)-2-(4-methoxy-phenyl)-ethenyl]-2H-indol-2-one (OOO), 4-[(E)-2-[2,3-Dihydro-(Z)-3-[(3-methoxy-1H-pyrrol-2-yl)methylene]-2-oxo-1H-indol-4-yl]ethenyl]benzoic acid methyl ester (PPP), and 1,3-Dihydro-4-[(E)-2-(3,4-dimethoxyphenyl)-ethenyl]-(Z)-3-[(3-methoxy-1H-pyrrol-2-yl)methylene]-2H-indol-2-one (QQQ).

42. A compound selected from the group consisting of (Z)-1,3-Dihydro-5-ethynyl-3-[(1H-pyrrol-2-yl)methylene]-2H-indol-2-one (SSS), (Z)-1,3-Dihydro-5-(4-hydroxyphenyl)ethynyl-3-[(1H-pyrrol-2-yl)methylene]-2H-indol-2-one (TTT), (Z)-1,3-Dihydro-5-(3-nitrophenyl)ethynyl-3-[(1H-pyrrol-2-yl)methylene]-2H-indol-2-one (UUU), (Z)-1,3-Dihydro-5-phenylethynyl-3-[(1H-pyrrol-2-yl)methylene]-2H-indol-2-one (VVV), (Z)-1,3-Dihydro-5-(3-hydroxyphenyl)ethynyl-3-[(1H-pyrrol-2-yl)methylene]-2H-indol-2-one (WWW), (Z)-1,3-Dihydro-5-(2-nitrophenyl)ethynyl-3-[(1H-pyrrol-2-yl)methylene]-2H-indol-2-one (XXX), (Z)-1,3-Dihydro-5-(4-nitrophenyl)ethynyl-3-[(1H-pyrrol-2-yl)methylene]-2H-indol-2-one (ZZZ), (Z)-5-(4-Aminophenyl)ethynyl-1,3-dihydro-3-[(1H-pyrrol-2-yl)methylene]-2H-indol-2-one (AAAA), (Z)-1,3-Dihydro-5-ethynyl-3-[(3-methoxy-1H-pyrrol-2-yl)methylene]-2H-indol-2-one (DDDD), (Z)-1,3-Dihydro-5-(3-pyridinyl)ethynyl-3-[(1H-pyrrol-2-yl)methylene]-2H-indol-2-one (EEEE), (Z)-1,3-Dihydro-5-(2-pyridinyl)ethynyl-3-[(1H-pyrrol-2-yl)methylene]-2H-indol-2-one (FFFF), (Z)-1,3-Dihydro-5-(4-hydroxyphenyl)ethynyl-3-[(3-methoxy-1H-pyrrol-2-yl)-methylene]-2H-indol-2-one (GGGG), (Z)-1,3-Dihydro-5-(4-methoxyphenyl)ethynyl-3-[(1H-pyrrol-2-yl)-methylene]-2H-indol-2-one (HHHH), (Z)-1,3-Dihydro-3-[(1H-pyrrol-2-yl)-methylene]-5-(2-thiophenyl)ethynyl-2H-indol-2-one (IIII), and (Z)-1,3-Dihydro-5-ethynyl-3-[(4-methyl-1H-imidazol-5-yl)methylene]-2H-indol-2-one, trifluoroacetate salt (LLLL).

43. A pharmaceutical composition comprising as an active ingredient an effective amount of a compound of claim 2 and a pharmaceutically acceptable carrier or excipient.

44. A pharmaceutical composition comprising as an active ingredient an effective amount of a compound of claim 20 and a pharmaceutically acceptable carrier or excipient.

45. The pharmaceutical composition of claim 43 which is suitable for parenteral administration.

46. The pharmaceutical composition of claim 44 which is suitable for parenteral administration.

47. A method for treating a neuro-degenerative disease comprising administering to a subject in need thereof a threrapeutically effective amount of a compound according to claim 2.

48. A method for treating a neuro-degenerative disease comprising administering to a subject in need thereof a threrapeutically effective amount of a compound according to claim 20.

49. A method for treating rheumatoid arthritis comprising administering to a subject in need thereof a therapeutically effective amount of a compound according to claim 2.

50. A method for treating rheumatoid arthritis comprising administering to a subject in need thereof a therapeutically effective amount of a compound according to claim 20.

51. A compound having the formula:

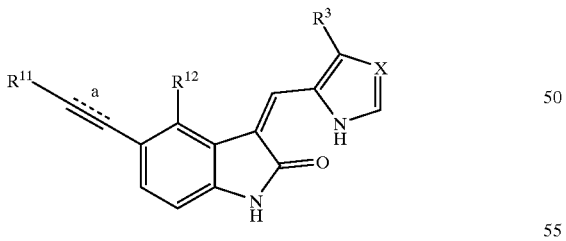

II or prodrugs or pharmaceutically active metabolites of compounds of formula II, or the pharmaceutically acceptable salts of all of the foregoing compounds, wherein:

$R^3$ is selected from the group consisting of
—H,
—$OR^4$,
—$COR^4$,
—$COOR^4$,
—$CONR^6R^7$,
halogen,
—CN
—$NR^6R^7$,
—perfluoroalkyl, and
lower alkyl which is unsubstituted or substituted by —$OR^8$ or —$NR^6R^7$;

$R^4$ is selected from the group consisting of
—H,
lower alkyl which is unsubstituted or substituted by the group consisting of —$OR^5$, —$COOR^8$, —$COR^8$, —$CONR^8R^9$, —$NR^6R^7$, cycloalkyl, heterocycle, —CN, —$NO_2$, —$SO_2R^8$, and —$SO_2NR^8R^9$,
cycloalkyl which is unsubstituted or substituted by the group consisting of —$OR^5$, —$COOR^8$, —$COR^8$, —$CONR^8R^9$, —$NR^6R^7$, lower alkyl, heterocycle, —CN, —$NO_2$, —$SO_2R^8$, and —$SO_2NR^8R^9$,
heterocycle which is unsubstituted or substituted by the group consisting of —$OR^5$, —$COOR^8$, —$COR^8$, —$CONR^8R^9$, —$NR^6R^7$, lower alkyl, cycloalkyl, —CN, —$NO_2$, —$SO_2R^8$, and —$SO_2NR^8R^9$,
aryl which is unsubstituted or substituted by the group consisting of —$OR^5$, —$COOR^8$, —$COR^8$, —$CONR^8R^9$, —$NR^6R^7$, cycloalkyl, heterocycle, —CN, —$NO_2$, —$SO_2R^8$, —$SO_2NR^8R^9$, and halogen,
heteroaryl which is unsubstituted or substituted by the group consisting of —$OR^5$, —$COOR^8$, —$COR^8$, —$CONR^8R^9$, —$NR^6R^7$, cycloalkyl, heterocycle, —CN, —$NO_2$, —$SO_2R^8$, —$SO_2NR^8R^9$, and halogen;

$R^5$ is selected from the group consisting of
—H,
—$COR^8$,
—$CONR^8R^9$, and
—lower alkyl which is unsubstituted or substituted by the group consisting of —$OR^9$, —$NR^9R^{10}$, —$N(COR^9)R^{10}$, —$COR^9$, —$CONR^9R^{10}$, —$SR^9$ and —$COOR^9$;

$R^6$ and $R^7$ are each independently selected from the group consisting of
—H,
—$COR^8$,
—$COOR^8$,
—$CONR^8R^9$,
—$SO_2R^8$,
—$SO_2NR^8R^9$,
lower alkyl which is unsubstituted or substituted by the group consisting of —$OR^5$, —$NR^8R^9$, —$COOR^8$, —$COR^8$, —$CONR^8R^9$, —CN, —$NO_2$, —$SO_2R^8$, —$SO_2NR^8R^9$,
cycloalkyl which is unsubstituted or substituted by the group consisting of —$OR^5$, —$COOR^8$, —$COR^8$, —$CONR^8R^9$, —$NR^8R^9$, lower alkyl, heterocycle, —CN, —$NO_2$, —$SO_2R^8$, and —$SO_2NR^8R^9$,
heterocycle which is unsubstituted or substituted by the group consisting of —$OR^5$, —$COOR^8$, —$COR^8$, —$CONR^8R^9$, —$NR^8R^9$, lower alkyl, cycloalkyl, —CN, —$NO_2$, —$SO_2R^8$, and —$SO_2NR^8R^9$,
aryl which is unsubstituted or substituted by the group consisting of —$OR^5$, —$COOR^8$, —$COR^8$, —$CONR^8R^9$, —$NR^8R^9$, lower alkyl, cycloalkyl, heterocycle, —CN, —$NO_2$, —$SO_2R^8$, and —$SO_2NR^8R^9$, and
heteroaryl which is unsubstituted or substituted by the group consisting of —$OR^5$, —$COOR^8$, —$COR^8$, —$CONR^8R^9$, —$NR^8R^9$, lower alkyl, cycloalkyl, heterocycle, —CN, —$NO_2$, —$SO_2R^8$, and —$SO_2NR^8R^9$,
cycloalkyl which is unsubstituted or substituted by the group consisting of —$OR^5$, —$COOR^8$, —$COR^8$, —CONR$^8$R$^9$, —NR$^8$R$^9$, lower alkyl, heterocycle, —CN, —NO$_2$, —SO$_2$R$^8$, and —SO$_2$NR$^8$R$^9$, heterocycle which is unsubstituted or substituted by the group consisting of —OR$^5$, —COOR$^8$, —COR$^8$, —CONR$^8$R$^9$, —NR$^8$R$^9$, lower alkyl, cycloalkyl, —CN, —NO$_2$, —SO$_2$R$^8$, and —SO$_2$NR$^8$R$^9$, aryl which is unsubstituted or substituted by the group consisting of —OR$^5$, —COOR$^8$, —COR$^8$, —CONR$^8$R$^9$, —NR$^8$R$^9$, lower alkyl, cycloalkyl, heterocycle, —CN, —NO$_2$, —SO$_2$R$^8$, and —SO$_2$NR$^8$R$^9$, heteroaryl which is unsubstituted or substituted by the group consisting of —OR$^5$, —COOR$^8$, —COR$^8$, —CONR$^8$R$^9$, —NR$^8$R$^9$, lower alkyl, cycloalkyl, heterocycle, —CN, —NO$_2$, —SO$_2$R$^8$, and —SO$_2$NR$^8$R$^9$, and —NR$^6$R$^7$ can a ring having 3 to 7 atoms, said ring not including any additional hetero atoms or including one or more additional hetero atoms and being unsubstituted or substituted by the group consisting of lower alkyl, —OR$^5$, —COR$^8$, —COOR$^8$, —CONR$^8$R$^9$, and —NR$^5$R$^9$;

R$^8$ is selected from the group consisting of
—H,
lower alkyl which is unsubstituted or substituted by the group consisting of cycloalkyl, heterocycle, aryl, heteroaryl, —OR$^9$, —NR$^9$R$^{10}$, and —N(COR$^9$)R$^{10}$,
aryl which is unsubstituted or substituted by the group consisting of —OR$^9$, —COOR$^9$, —COR$^9$, —CONR$^{10}$R$^9$, —NR$^{10}$R$^9$, lower alkyl, cycloalkyl, heterocycle, —CN, —NO$_2$, —SO$_2$R$^9$, and —SO$_2$NR$^{10}$R$^9$, and
heteroaryl which is unsubstituted or substituted by the group consisting of —OR$^9$, —COOR$^9$, —COR$^9$, —CONR$^{10}$R$^9$, —NR$^{10}$R$^9$, lower alkyl, cycloalkyl, heterocycle, —CN, —NO$_2$, —SO$_2$R$^9$, and —SO$_2$NR$^{10}$R$^9$;
cycloalkyl which is unsubstituted or substituted by the group consisting of —OR$^9$, —COOR$^9$, —COR$^9$, —CONR$^{10}$R$^9$, —NR$^{10}$R$^9$, lower alkyl, heterocycle, —CN, —NO$_2$, —SO$_2$R$^9$, and —SO$_2$NR$^{10}$R$^9$; and
heterocycle which is unsubstituted or substituted by the group consisting of —OR$^9$, —COOR$^9$, —COR$^9$, —CONR$^{10}$R$^9$, —NR$^{10}$R$^9$, lower alkyl, cycloalkyl, —CN, —NO$_2$, —SO$_2$R$^9$, and —SO$_2$NR$^{10}$R$^9$;

R$^9$ and R$^{10}$ are each independently selected from the group consisting of
—H and lower alkyl;

R$^{11}$ is selected from the group consisting of
—H,
—COR$^4$,
—COOR$^4$,
—CONR$^6$R$^7$,
lower alkyl which is unsubstituted or substituted by the group consisting of —OR$^5$, —NR$^6$R$^7$, halogen, —NO$_2$, —SO$_2$R$^4$, —SO$_2$NR$^6$R$^7$, —CN, —COR$^4$, —COOR$^4$, —CONR$^6$R$^7$, cycloalkyl, heterocycle, aryl, and heteroaryl, cycloalkyl, which is unsubstituted or substituted by the group consisting of —OR$^5$, —NR$^6$R$^7$, halogen, —NO$_2$, —SO$_2$R$^4$, —SO$_2$NR$^6$R$^7$, —CN, —COR$^4$, —COOR$^4$, —CONR$^6$R$^7$, lower alkyl, heterocycle, aryl, and heteroaryl, heterocycle, which is unsubstituted or substituted by the group consisting of —OR$^5$, —NR$^6$R$^7$, halogen, —NO$_2$, —SO$_2$R$^4$, —SO$_2$NR$^6$R$^7$, —CN, —COR$^4$, —COOR$^4$, —CONR$^6$R$^7$, lower alkyl, cycloalkyl, aryl, and heteroaryl, aryl, which is unsubstituted or substituted by the group consisting of —OR$^5$, —NR$^6$R$^7$, halogen, —NO$_2$, —SO$_2$R$^4$, —SO$_2$NR$^6$R$^7$, —CN, —COR$^4$, —COOR$^4$, —CONR$^6$R$^7$, lower alkyl, and perfluoroalkyl, and heteroaryl, which is unsubstituted or substituted by the group consisting of —OR$^5$, —NR$^6$R$^7$, halogen, —NO$_2$, —SO$_2$R$^4$, —SO$_2$NR$^6$R$^7$, —CN, —COR$^4$, —COOR$^4$, —CONR$^6$R$^7$, lower alkyl, and perfluoroalkyl; and R$^{12}$ is selected from the group consisting of
—H,
—OR$^4$,
—OCOR$^4$,
—COR$^4$,
—COOR$^4$,
—CONR$^6$R$^7$,
—NR$^6$R$^7$,
—halogen,
—NO$_2$,
—CN,
—SO$_2$R$^4$,
—SO$_2$NR$^6$R$^7$,
—perfluoroalkyl,
lower alkyl which is unsubstituted or substituted from the group consisting of —OR$^4$, —NR$^6$R$^7$, cycloalkyl, heterocycle, —COR$^4$, —COOR$^4$, —CONR$^6$R$^7$, —CN, —NO$_2$, —SO$_2$R$^4$, —SO$_2$NR$^6$R$^7$ and halogen, cycloalkyl which is unsubstituted or substituted from the group consisting of —OR$^4$, —NR$^6$R$^7$, lower alkyl, heterocycle, —COR$^4$, —COOR$^4$, —CONR$^6$R$^7$, —CN, —NO$_2$, —SO$_2$R$^4$, —SO$_2$NR$^6$R$^7$ and halogen, and heterocycle which is unsubstituted or substituted from the group consisting of —OR$^4$, —NR$^6$R$^7$, lower alkyl, cycloalkyl, —COR$^4$, —COOR$^4$, —CONR$^6$R$^7$, —CN, —NO$_2$, —SO$_2$R$^4$, —SO$_2$NR$^6$R$^7$ and halogen;

X is selected from the group consisting of
—N— and —C—; and a is or is not a bond.

* * * * *

UNITED STATES PATENT AND TRADEMARK OFFICE
CERTIFICATE OF CORRECTION

PATENT NO. : 6,313,310 B1
DATED : November 6, 2001
INVENTOR(S) : Kin-Chun Luk, Paige E. Mahaney and Steven Gregory Mischke It is certified that error appears in the above-identified patent and that said Letters Patent is hereby corrected as shown below:

Title page,
The Related U.S. Application Data is not listed on the cover page, and should read as follows:
-- Related U.S. Application Data:
Provisional Application No. 60/112,589, filed on December 17, 1998; and
Provisional Application No. 60/141,482, filed on June 29, 1999 --.

Column 86, claim 1,
Lines 31-32, Please add "-$OR^4$," after halogen and before "-$OCOR^4$,".

Column 89, claim 2,
Line 10, "-$NR^6R^7$ can y form" should read -- $NR^6R^7$ can form --.

Signed and Sealed this

Sixteenth Day of April, 2002

Attest:

*Attesting Officer*

JAMES E. ROGAN
*Director of the United States Patent and Trademark Office*